US012653829B2

(12) United States Patent
Stover et al.

(10) Patent No.: US 12,653,829 B2
(45) Date of Patent: Jun. 16, 2026

(54) FORMULATED AND/OR CO-FORMULATED COMPOSITIONS CONTAINING A2aR ANTAGONIST PRODRUGS USEFUL IN THE TREATMENT OF CANCER AND METHODS THEREOF

(71) Applicant: Nammi Therapeutics, Inc., Los Angeles, CA (US)

(72) Inventors: David Stover, Encino, CA (US); Dhruba Bharali, Sherman Oaks, CA (US); Bruce A Hay, Niskayuna, NY (US); Tahmineh Safaie, Los Angeles, CA (US)

(73) Assignee: Nammi Therapeutics, Inc., Los Angeles, CA (US)

( * ) Notice: Subject to any disclaimer, the term of this patent is extended or adjusted under 35 U.S.C. 154(b) by 1037 days.

(21) Appl. No.: 17/803,220

(22) Filed: Mar. 18, 2022

(65) Prior Publication Data

US 2022/0401451 A1 Dec. 22, 2022

Related U.S. Application Data

(60) Provisional application No. 63/207,749, filed on Mar. 18, 2021.

(51) Int. Cl.
| | |
|---|---|
| *A61K 31/53* | (2006.01) |
| *A61K 47/54* | (2017.01) |
| *A61K 47/69* | (2017.01) |
| *B82Y 5/00* | (2011.01) |

(52) U.S. Cl.
CPC ............ *A61K 31/53* (2013.01); *A61K 47/543* (2017.08); *A61K 47/6911* (2017.08); *B82Y 5/00* (2013.01)

(58) Field of Classification Search
CPC .. A61K 31/53; A61K 47/6911; A61K 47/543; B82Y 5/00
See application file for complete search history.

(56) References Cited

U.S. PATENT DOCUMENTS

| | | | |
|---|---|---|---|
| 5,726,164 | A | 3/1998 | Wder et al. |
| 6,664,252 | B2 | 12/2003 | Castelhano et al. |
| 6,673,802 | B2 | 1/2004 | Castelhano et al. |
| 7,429,574 | B2 | 9/2008 | Castelhano et al. |
| 7,504,407 | B2 | 3/2009 | Castelhano et al. |
| 8,232,313 | B2 | 7/2012 | Munn et al. |
| 8,883,177 | B2 | 11/2014 | Wu |
| 8,912,162 | B2 | 12/2014 | Ahrabi et al. |
| 9,017,974 | B2 | 4/2015 | Zheng et al. |
| 9,526,787 | B2 | 12/2016 | Ko et al. |
| 9,598,422 | B2 | 3/2017 | Beck et al. |
| 9,732,035 | B2 | 8/2017 | Mautino et al. |
| 10,004,694 | B2 | 6/2018 | Park et al. |
| 10,022,365 | B2 | 7/2018 | Tong et al. |
| 10,028,913 | B2 | 7/2018 | Li et al. |

| | | | |
|---|---|---|---|
| 10,287,606 | B2 | 5/2019 | Valamehr et al. |
| 10,392,405 | B2 | 8/2019 | Malathong et al. |
| 10,399,962 | B2 | 9/2019 | Beatty et al. |
| 10,428,083 | B2 | 10/2019 | Harter et al. |
| 10,568,868 | B2 | 2/2020 | Slusher et al. |
| 10,702,526 | B2 | 7/2020 | Webster et al. |
| 10,781,189 | B2 | 9/2020 | Sasikkumar et al. |
| 10,995,101 | B2 | 5/2021 | Crosignani et al. |
| 11,034,708 | B2 | 6/2021 | Asai et al. |
| 11,045,472 | B2 | 6/2021 | Leleti et al. |
| 11,096,964 | B2 | 8/2021 | Rosen et al. |
| 11,246,906 | B2 | 2/2022 | Losey et al. |
| 11,376,255 | B2 | 7/2022 | Crosignani et al. |
| 11,400,155 | B2 | 8/2022 | Coric |
| 11,413,244 | B2 | 8/2022 | Kasagi et al. |
| 11,433,143 | B2 | 9/2022 | Nel et al. |
| 2003/0165568 | A1 | 9/2003 | Colombo et al. |
| 2008/0070936 | A1 | 3/2008 | Castelhano et al. |
| 2010/0178299 | A1 | 7/2010 | Sitkovsky et al. |
| 2011/0178164 | A1 | 7/2011 | Cunha Dias Real Oliveira et al. |
| 2015/0071990 | A1 | 3/2015 | Longnecker |
| 2018/0044304 | A1 | 2/2018 | Sasikumar et al. |
| 2018/0303949 | A1 | 10/2018 | Zhang |

(Continued)

FOREIGN PATENT DOCUMENTS

| | | | |
|---|---|---|---|
| WO | WO 2017/147407 A1 | 8/2017 | |
| WO | WO-2018175473 A1 * | 9/2018 | ........... A61K 31/519 |

(Continued)

OTHER PUBLICATIONS

Jorg et al.; Novel adenosine A2A receptor ligands: A synthetic, functional and computational investigation of selected literature adenosine A2A receptor antagonists for extending into extracellular space; Elsevier; Bioorganic & Medicinal Chemistry Letters 23 (2013) 3427-3433 (Year: 2013).*

Jacobson et al; Adenosine analogs with covalently attached lipids have enhanced potency at AI-adenosine receptors; Elsevier; vol. 225, No. 1,2, 97-102 FEBS Letters 1987 (Year: 1987).*

Langmead et al.; Identification of Novel Adenosine A2A Receptor Antagonists by Virtual Screening; ACS Publications; J. Med. Chem. 2012, 55, 1904-1909 (Year: 2012).*

Vecchio, et al., Ligand-Independent Adenosine A2B Receptor Constitutive Activity as a Promotor of Prostate Cancer . . . , J. Pharmacol Exp. Ther. 357:36-44 (Apr. 2016).

Jaakola, et al., The 2.6 A Crystal Strcuture of a Human A2a Adenosine Receptor Bound to an Antagonist, Science, 322(5905): pp. 1211-1217 (Nov. 21, 2008).

(Continued)

*Primary Examiner* — Robert A Wax
*Assistant Examiner* — John W Lippert, III
(74) *Attorney, Agent, or Firm* — LOSMP; Shane M. Popp, LL.M.

(57) ABSTRACT

Formulated and/or co-formulated nanocarriers (e.g., LNPs and/or SLNPs) comprising AR Prodrugs and methods of making the nanocarriers are disclosed herein. The AR prodrug compositions comprise a drug moiety, a lipid moiety, and linkage unit that inhibit A2aR. The AR Prodrugs can be formulated and/or co-formulated into a nanocarrier to provide a method of treating cancer, immunological disorders, and other disease by utilizing a targeted drug delivery vehicle.

7 Claims, 24 Drawing Sheets

(56) References Cited

U.S. PATENT DOCUMENTS

| | | | |
|---|---|---|---|
| 2018/0339044 A1* | 11/2018 | Gutierrez ......... | C07K 14/70532 |
| 2019/0099413 A1 | 4/2019 | Tanaka et al. | |
| 2019/0358343 A1 | 11/2019 | Wang et al. | |
| 2020/0102319 A1 | 4/2020 | Crosignani | |
| 2020/0197534 A1 | 6/2020 | Mei et al. | |
| 2021/0137930 A1 | 5/2021 | Fardis | |
| 2021/0161898 A1 | 6/2021 | Leleti et al. | |
| 2021/0163418 A1 | 6/2021 | Stover et al. | |
| 2021/0251995 A1 | 8/2021 | Bell et al. | |
| 2021/0315912 A1 | 10/2021 | Karp et al. | |
| 2021/0332055 A1 | 10/2021 | Sun et al. | |
| 2022/0025015 A1 | 1/2022 | Wang | |
| 2022/0211701 A1 | 7/2022 | Anderson et al. | |
| 2022/0267350 A1 | 8/2022 | Yu et al. | |
| 2022/0339160 A1 | 10/2022 | Yu et al. | |

FOREIGN PATENT DOCUMENTS

| | | | |
|---|---|---|---|
| WO | WO 2018/213631 A1 | 11/2018 | |
| WO | WO 2022/119531 A1 | 6/2022 | |

OTHER PUBLICATIONS

Carpenter, et al., Structure of the Adeonsine A2a Receptor Bound to an Engineered G Protein, Nature 536(7614): 104-107 (Aug. 4, 2016).

Jacobson, et al., Adenosine Analogs with Covalently Attached Lipids have Enhanced Potency at A1-Adeonosine Receptors, FEBS Letters (1987), 225(1-2), pp. 97-102.

Jacobson, et al., Adenosine Analogs with Covalently Attached Lipids have Enhanced Potency at A1-Adeonosine Receptors, FEBS Lett. 225(0): pp. 97-102 (Dec. 10, 1987).

Jorg, et al., Novel Adenosine A2a Receptor Ligands: A Synthetic, Functional and Computational Investigation of Selected . . . , Bioorg. Med. Chem. Lett. 23 (2013) pp. 3427-3433.

Maillard, et al., Adenosine Receptor Prodrugs: Synthesis and Biological Activity of Derivatives of Potent A1- . . . , J. Pharm. Sci., vol. 83, nb. 1, pp. 46-53 (1994)—Abstract.

Maillard, et al., Adenosine Receptor Prodrugs: Synthesis and Biological Activity of Derivatives of Potent A1- . . . , J. Pharm. Sci., vol. 83, nb. 1, pp. 46-53 (1994).

Ohta, et al., The Role of G-Coupled Adenosine Receptors in Downregulation of Inflammation and Protection From Tissue Damage, Nature, vol. 414, pp. 916-920 (Dec. 2001).

Helms, et al., Rethinking the Adenosine-A2aR Checkpoint: Implications for Enhancing Anti-Tumor Immunotherapy, Curr. Opin. in Pharmac. 53: pp. 77-83 (2020).

Willingham, et al., Targeting the A2aR in Cancer; Early Lessons from the Clinic, Curr. Opin. in Pharmac., 53: pp. 126-133 (2020).

Schiffman, et al., Adenosine A2a Receptors and Basal Ganglia Physiology, Prog. Neurobiol.; 83(5) pp. 277-292 (Dec. 2007).

Ongini, et al., Selective Adenosine A2aR Receptors Antagonists, II Farmaco, 56(2001) pp. 87-90.

Dore, et al., Structure of the Adenosine A2a Receptor in Complex with ZM241385 and the Xanthines XAC and Caffeine, Structure; 19(9) pp. 1283-1293 (Sep. 7, 2011).

* cited by examiner

Figure1. Chemical Synthesis for AR5-Prodrug

Figure 2. A2aR Inhibitor Prodrug Synthesis Schema with Carboxylic Acid Functionality
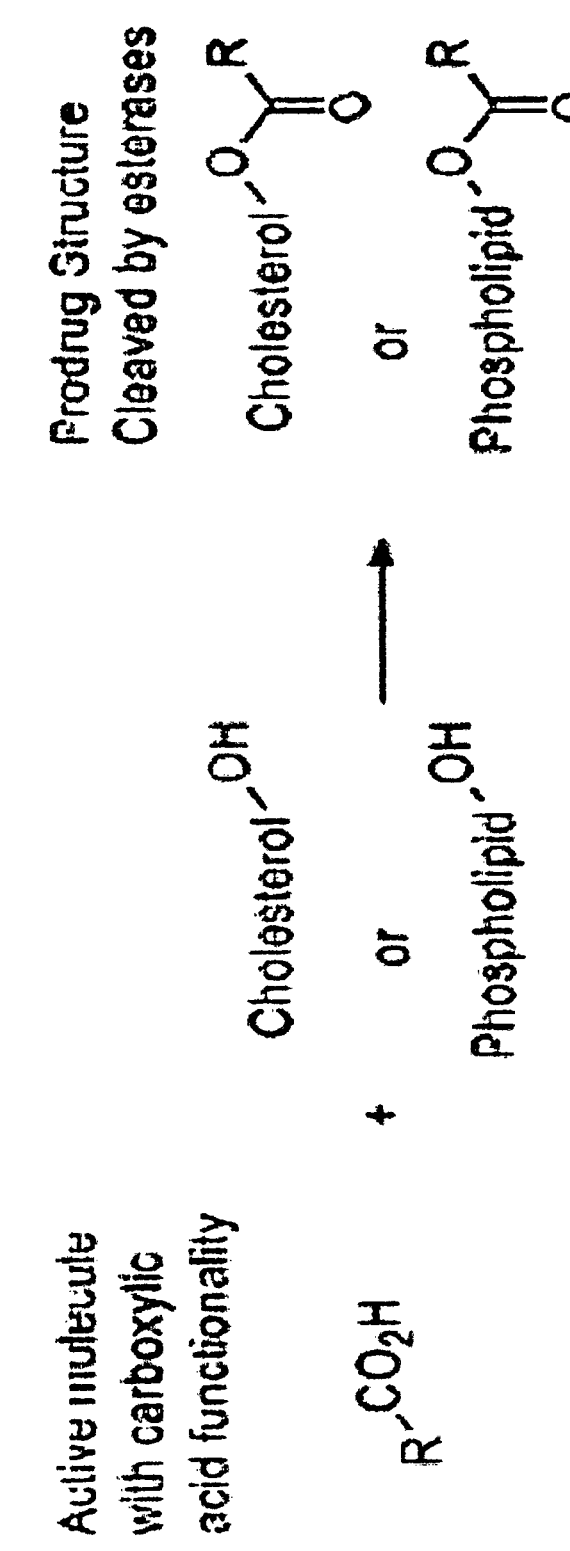

Figure 3. A2aR Inhibitor Prodrug Synthesis Schema with Alcohol Functionality

Figure 4. A2aR Inhibitor Prodrug Synthesis Schema with Secondary Amine, Amide, or Aniline Functionality

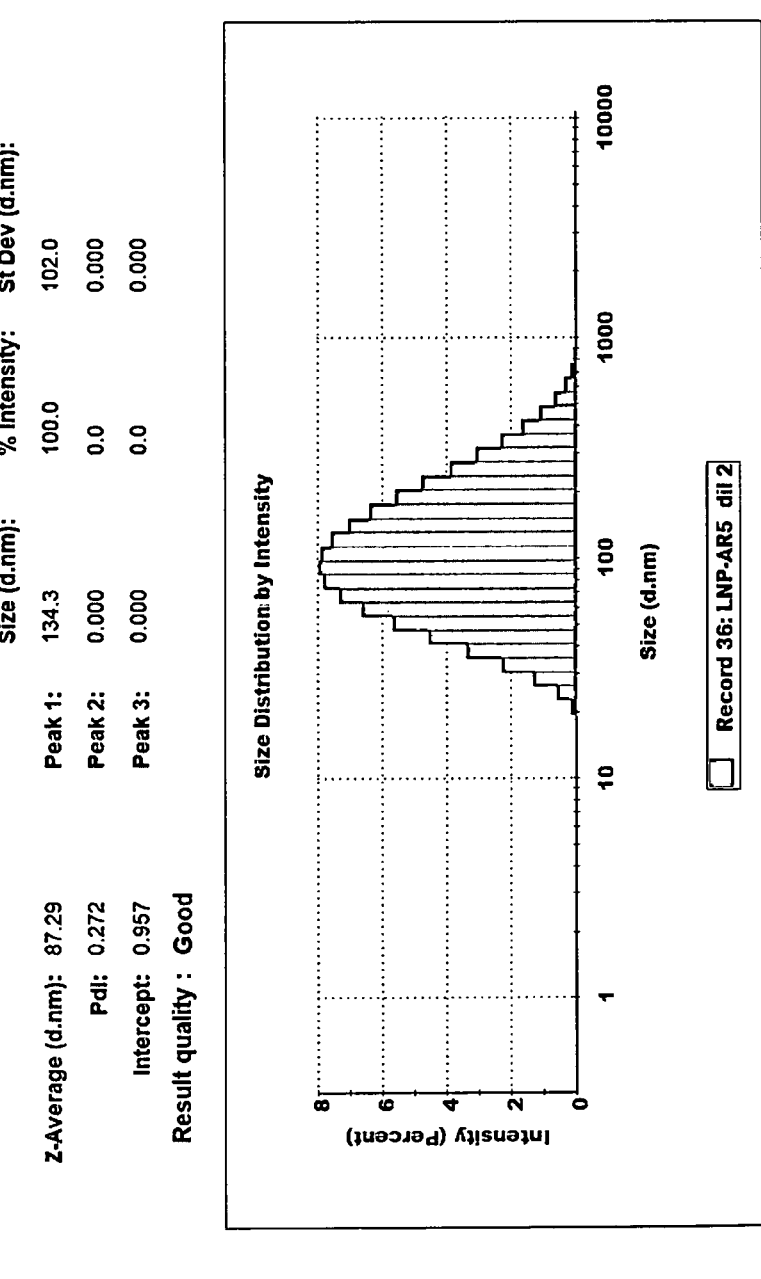
Figure 5. Characterization of LNP-AR5 Liposome

Figure 6. Characterization of LNP-AR5 Liposome (Zeta Potential)
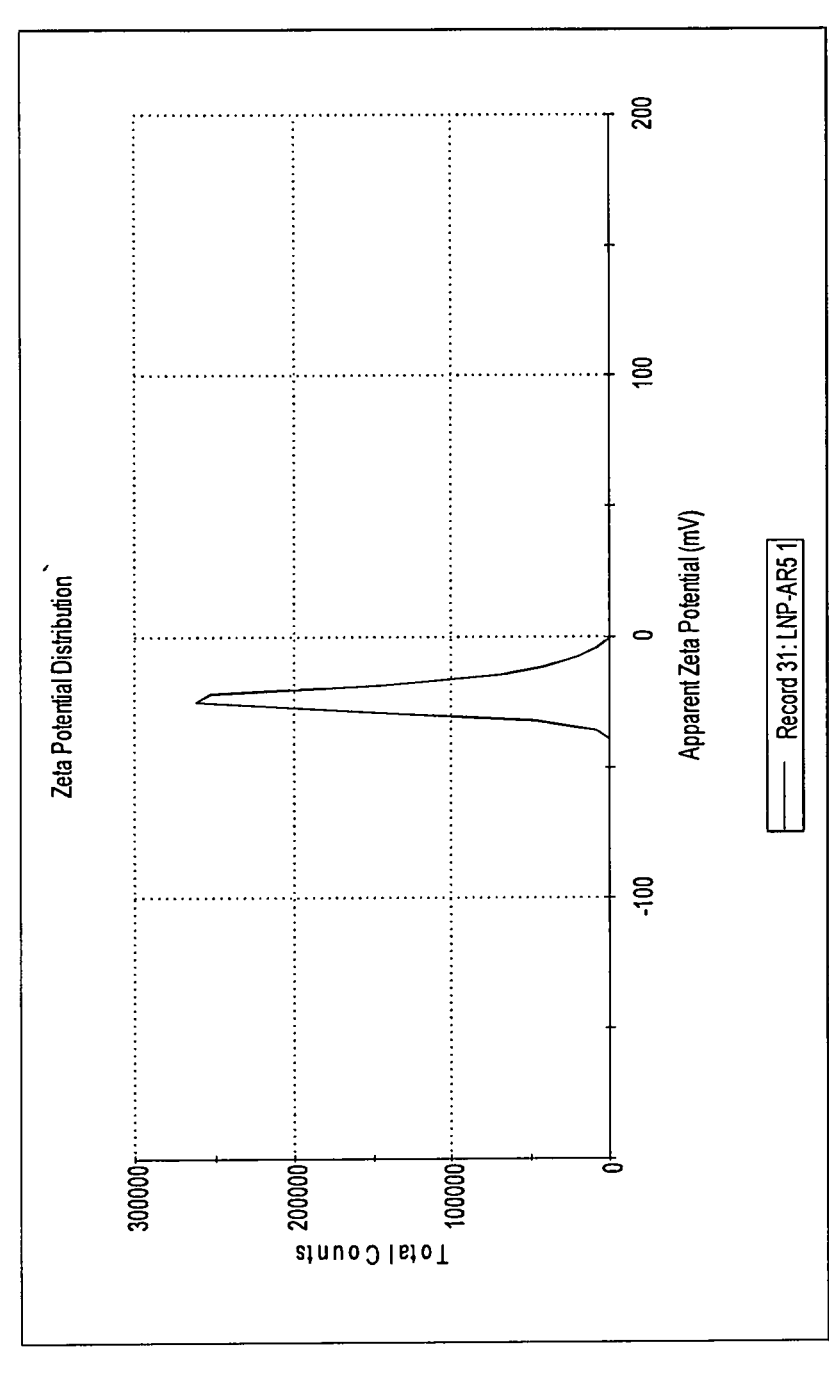

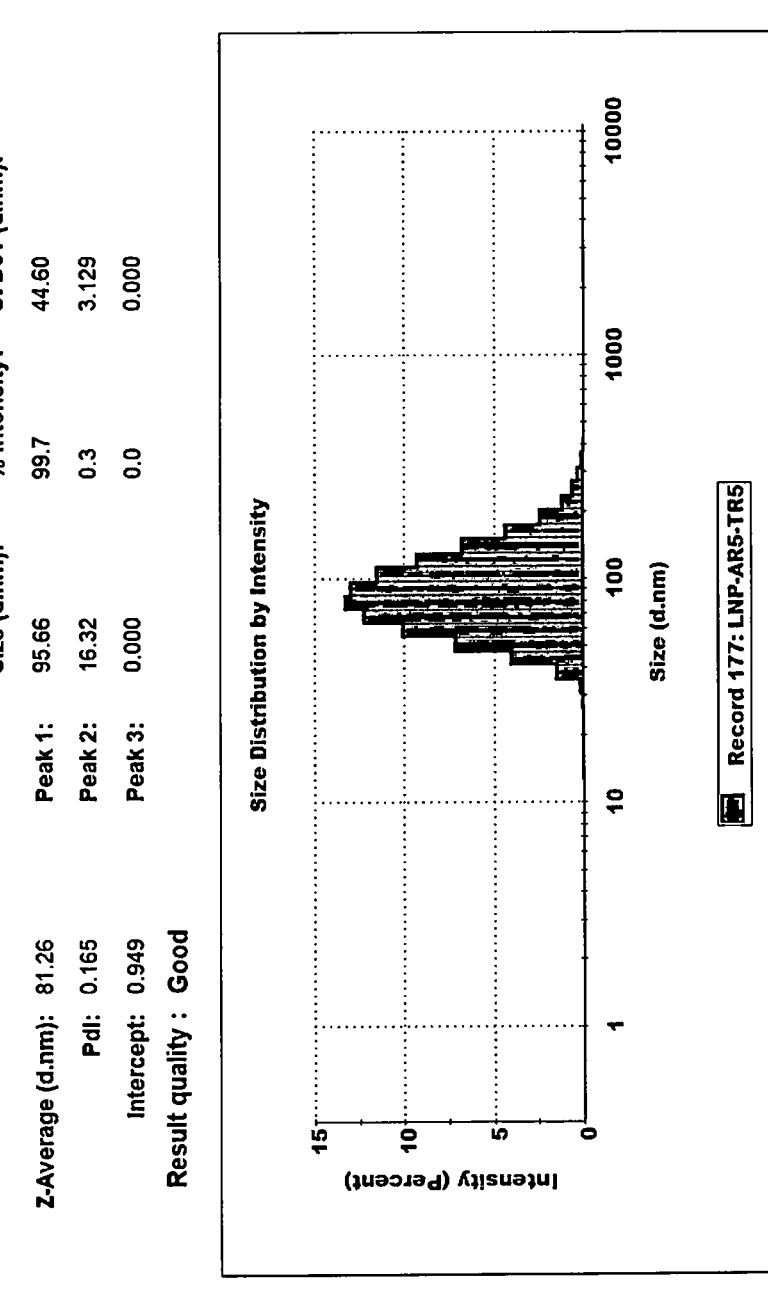
Figure 7. Characterization of LNP-AR5-TR5 Liposome

Figure 8. Characterization of LNP-AR5-TR5 Liposome (Zeta Potential)
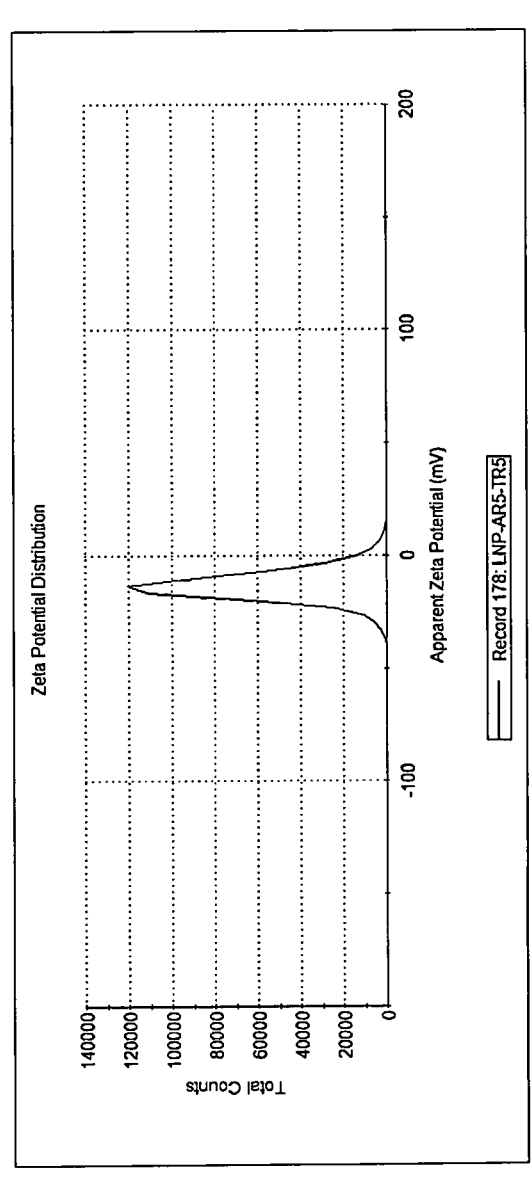
| | Mean (mV) | Area (%) | St Dev (mV) |
|---|---|---|---|
| Peak 1: | -13.3 | 100.0 | 6.73 |
| Peak 2: | 0.00 | 0.0 | 0.00 |
| Peak 3: | 0.00 | 0.0 | 0.00 |
Zeta Potential (mV): -13.2
Zeta Deviation (mV): 6.59
Conductivity (mS/cm): 0.394
Result quality : Good Figure 9. Characterization of LNP-AR5-ID3 Liposome
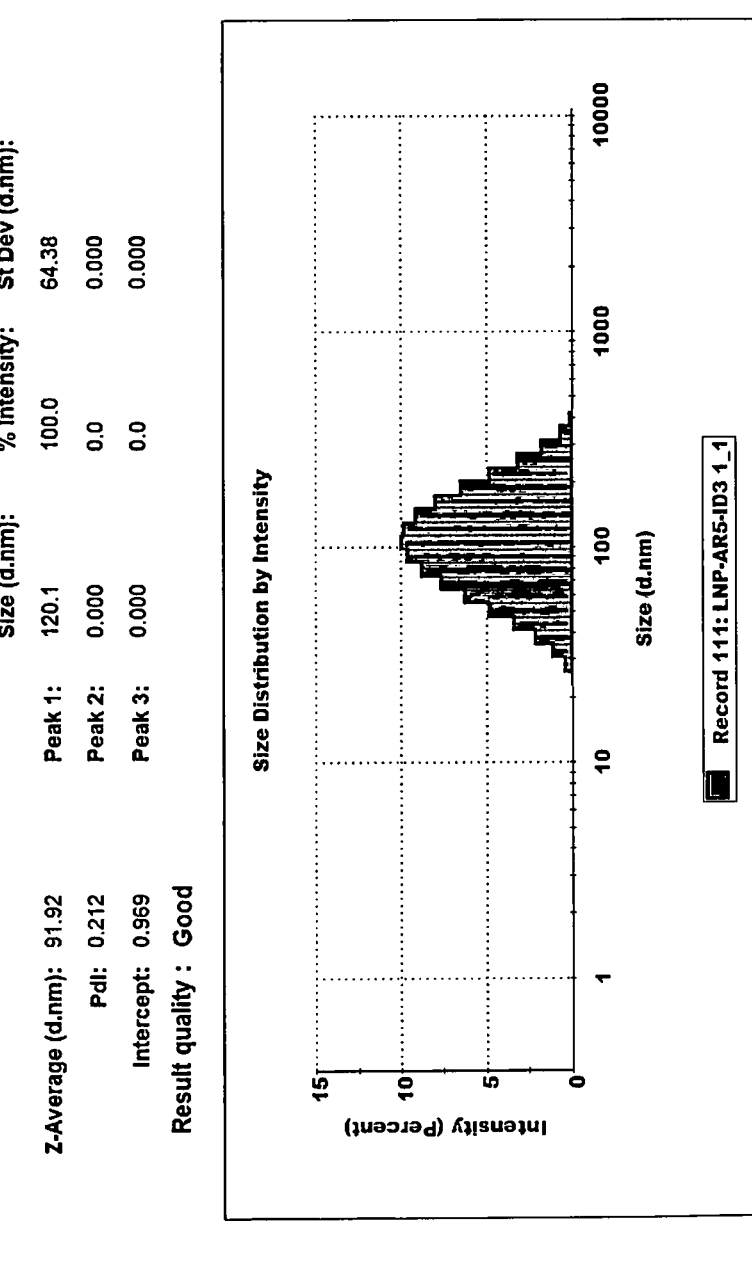

Figure 10. Characterization of LNP-AR5-ID3 Liposome (Zeta Potential)
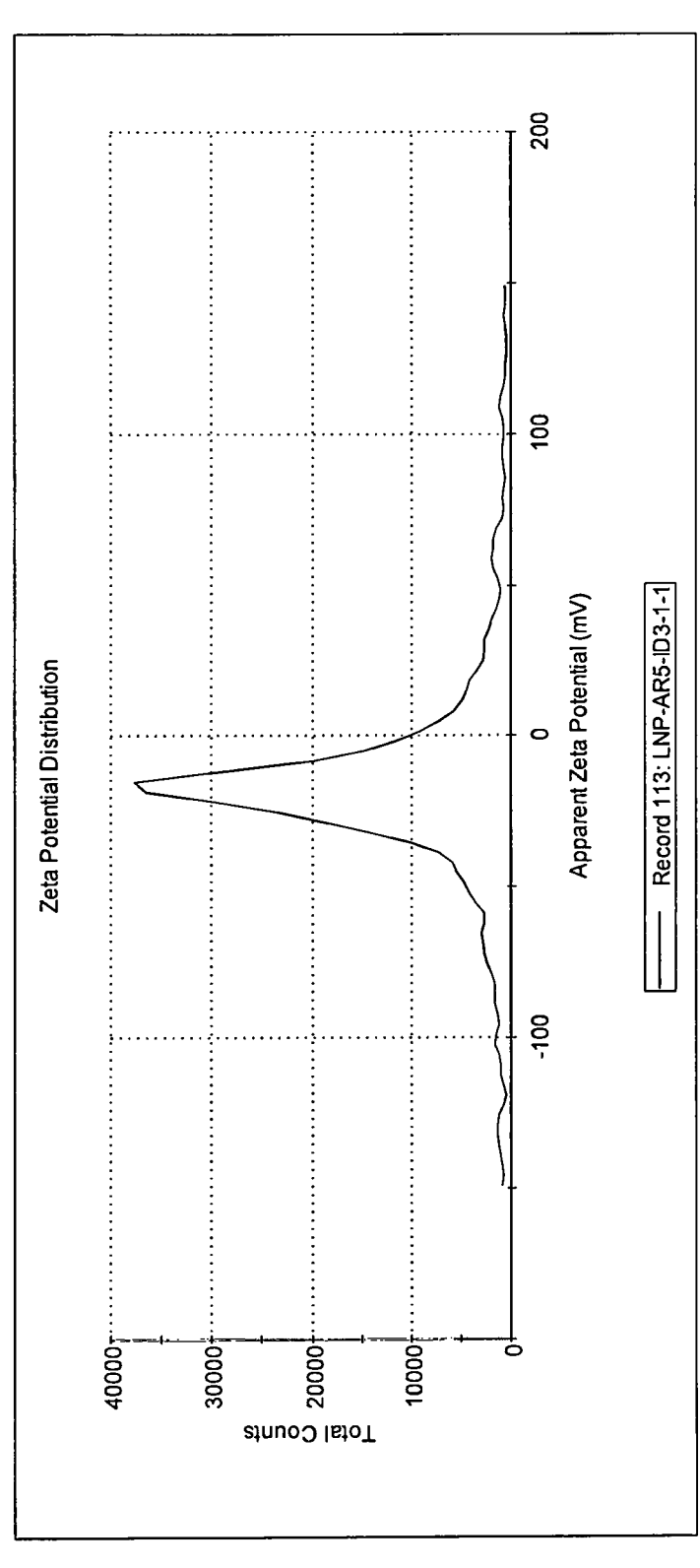

Figure 11. Characterization of LNP-AR5-TR5-ID3 Liposome
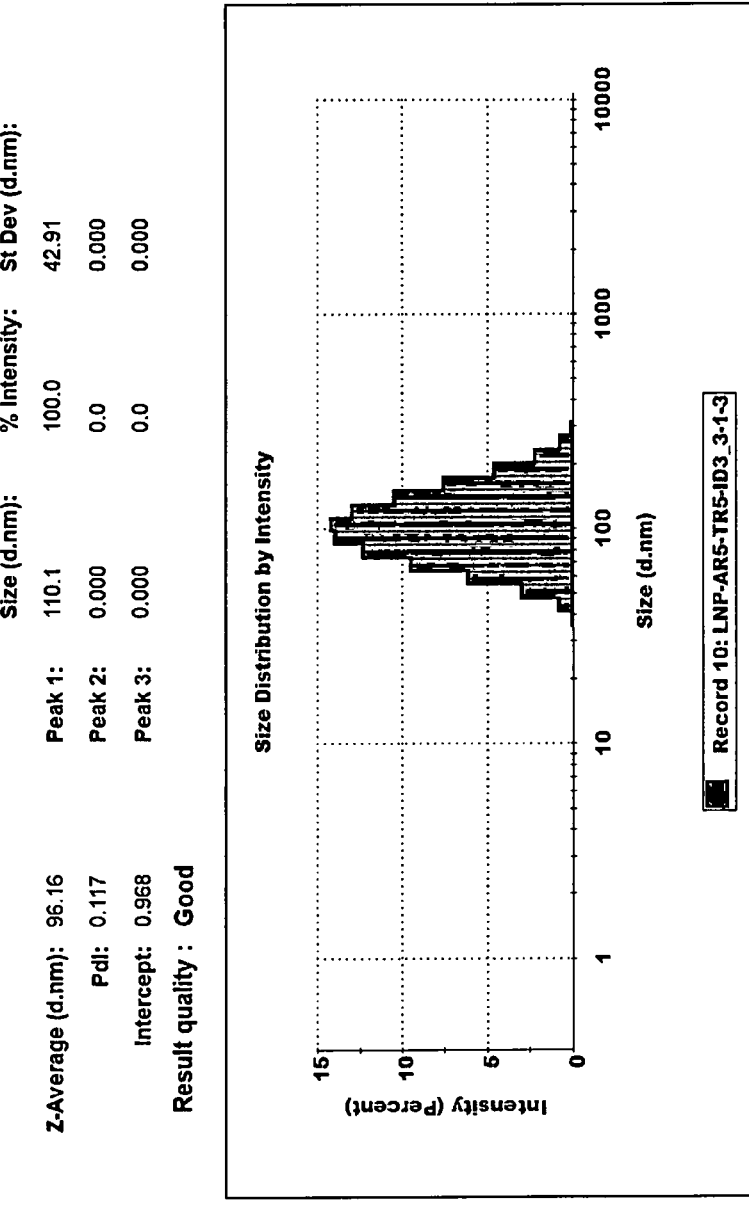

Figure 12. Characterization of LNP-AR5-TR5-ID3 Liposome (Zeta Potential)
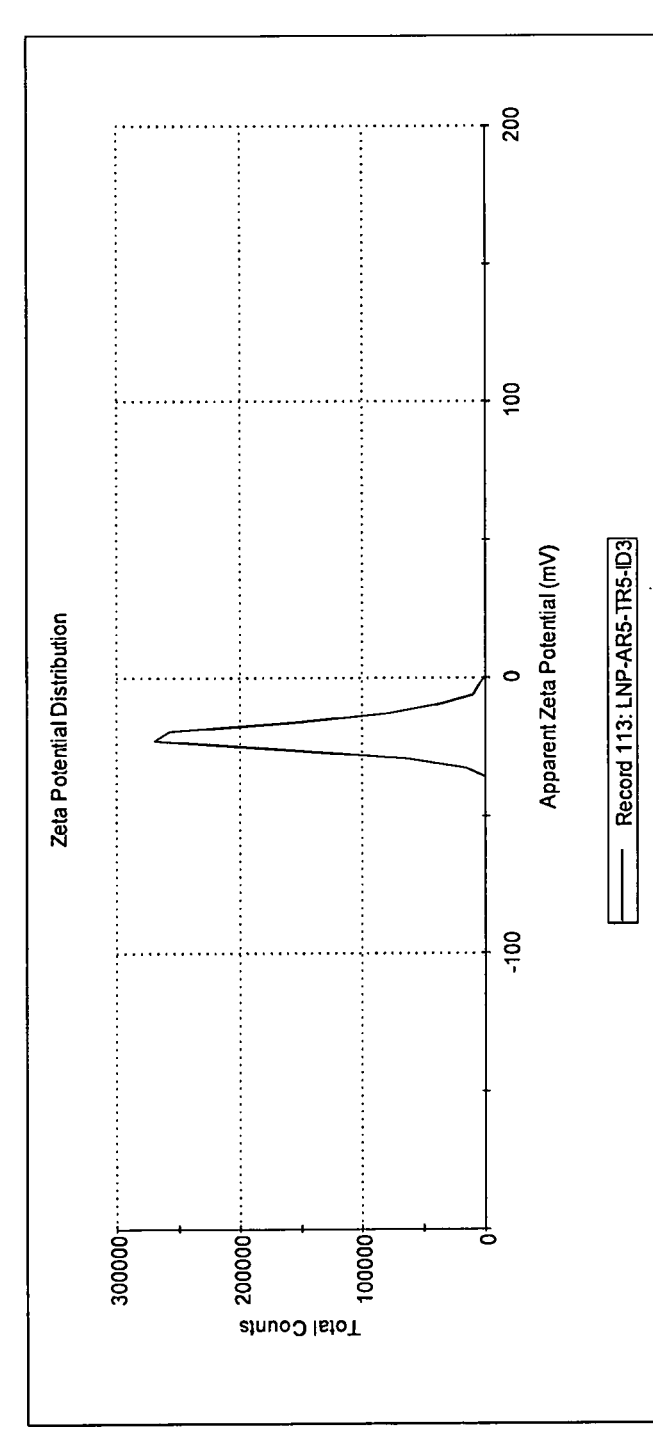

Figure 13. Characterization of SLNP-AR5 Solid-Lipid Nanocarrier
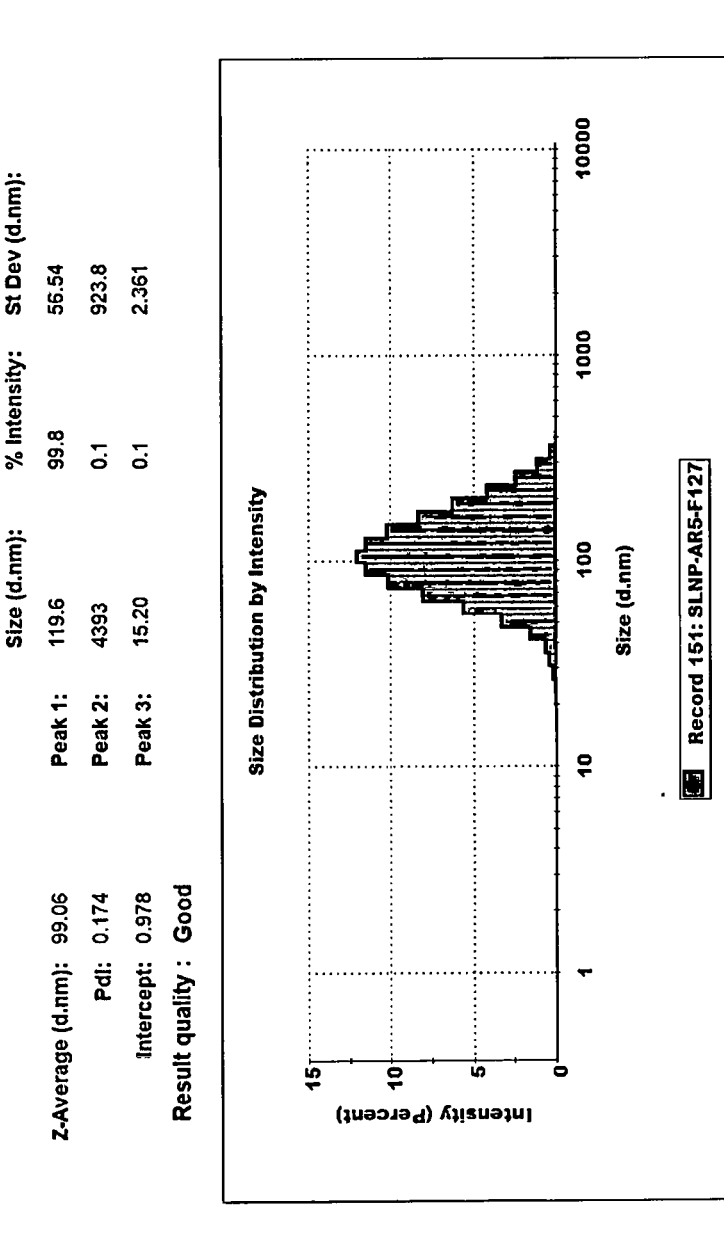

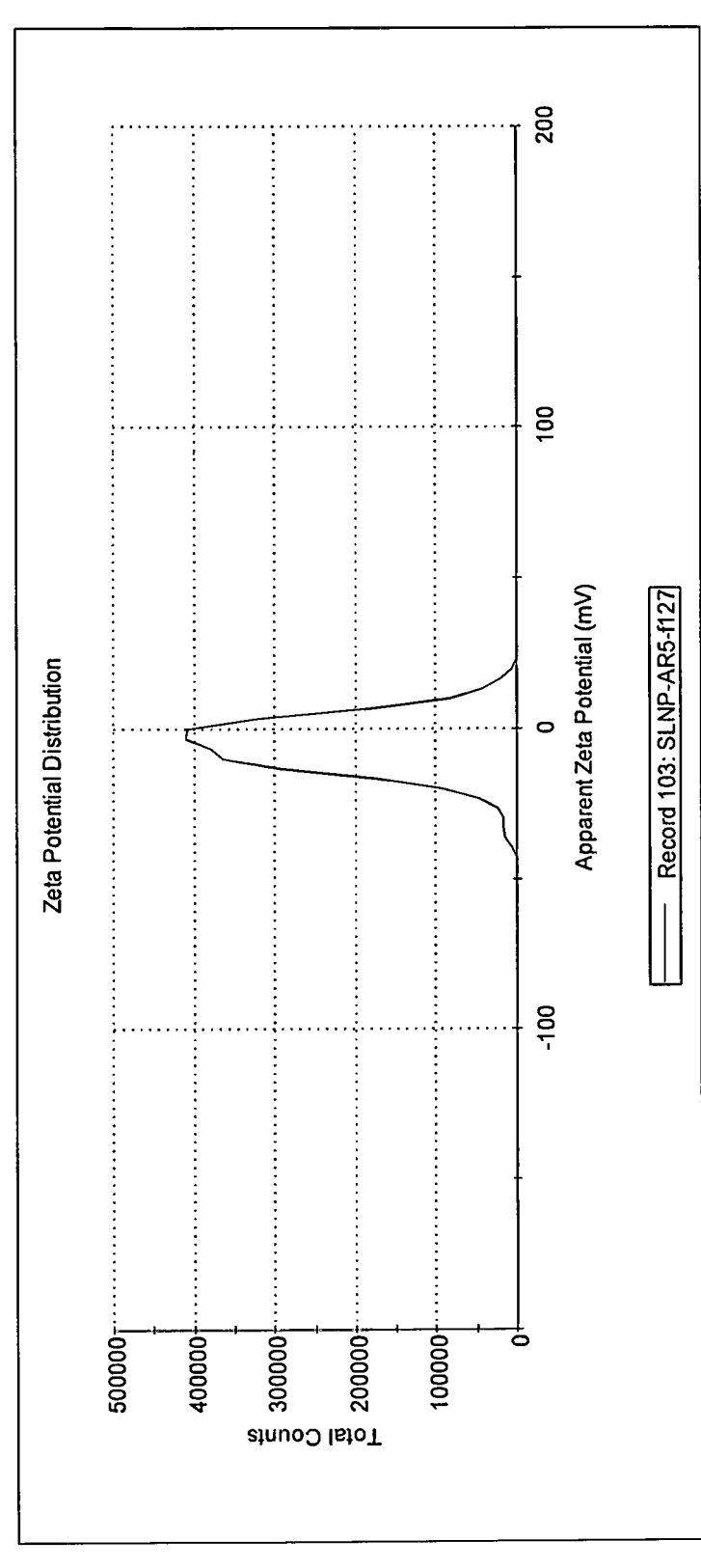
Figure 14. Characterization of SLNP-AR5 (Zeta Potential)

Figure 15. Characterization of SLNP-AR5-TR5 Solid-Lipid Nanocarrier
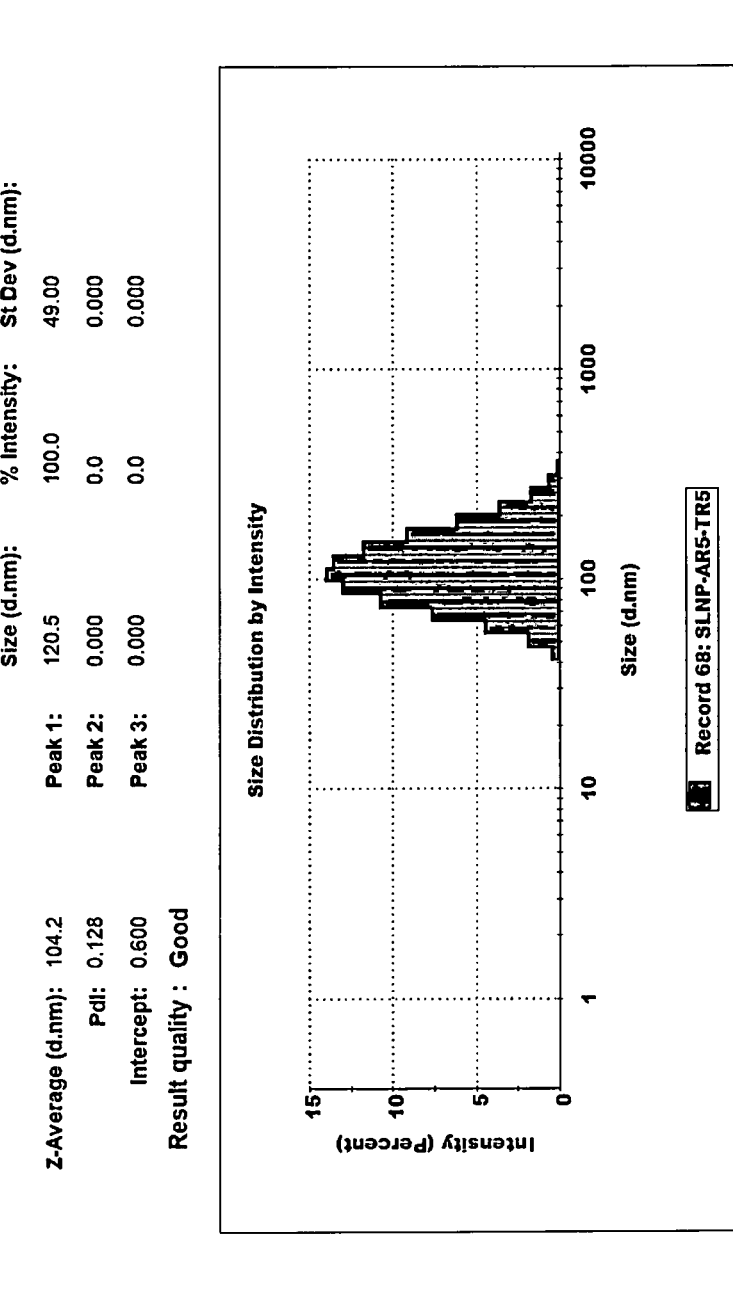
| | | Size (d.nm): | % Intensity: | St Dev (d.nm): |
|---|---|---|---|---|
| | Peak 1: | 120.5 | 100.0 | 49.00 |
| | Peak 2: | 0.000 | 0.0 | 0.000 |
| | Peak 3: | 0.000 | 0.0 | 0.000 |
Z-Average (d.nm): 104.2
Pdi: 0.128
Intercept: 0.600
Result quality : Good Figure 16. Characterization of SLNP-AR5-TR5 (Zeta Potential)
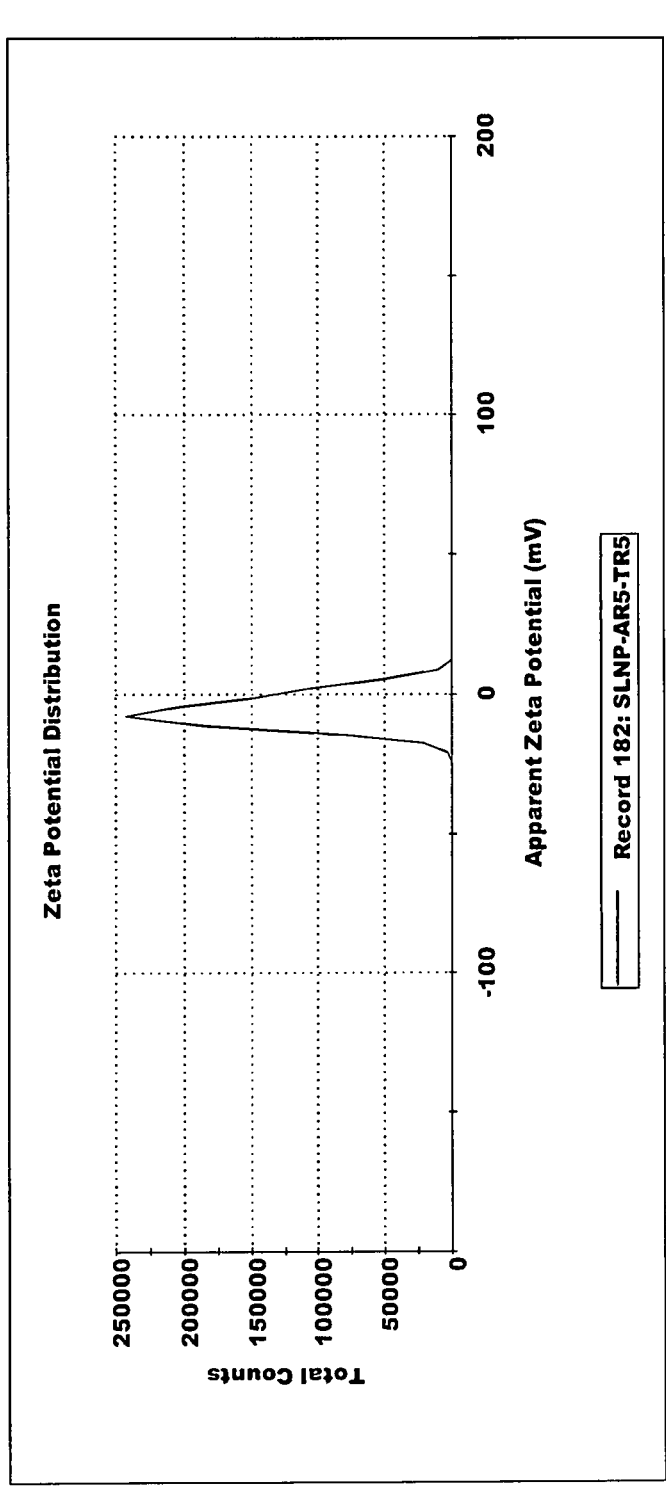

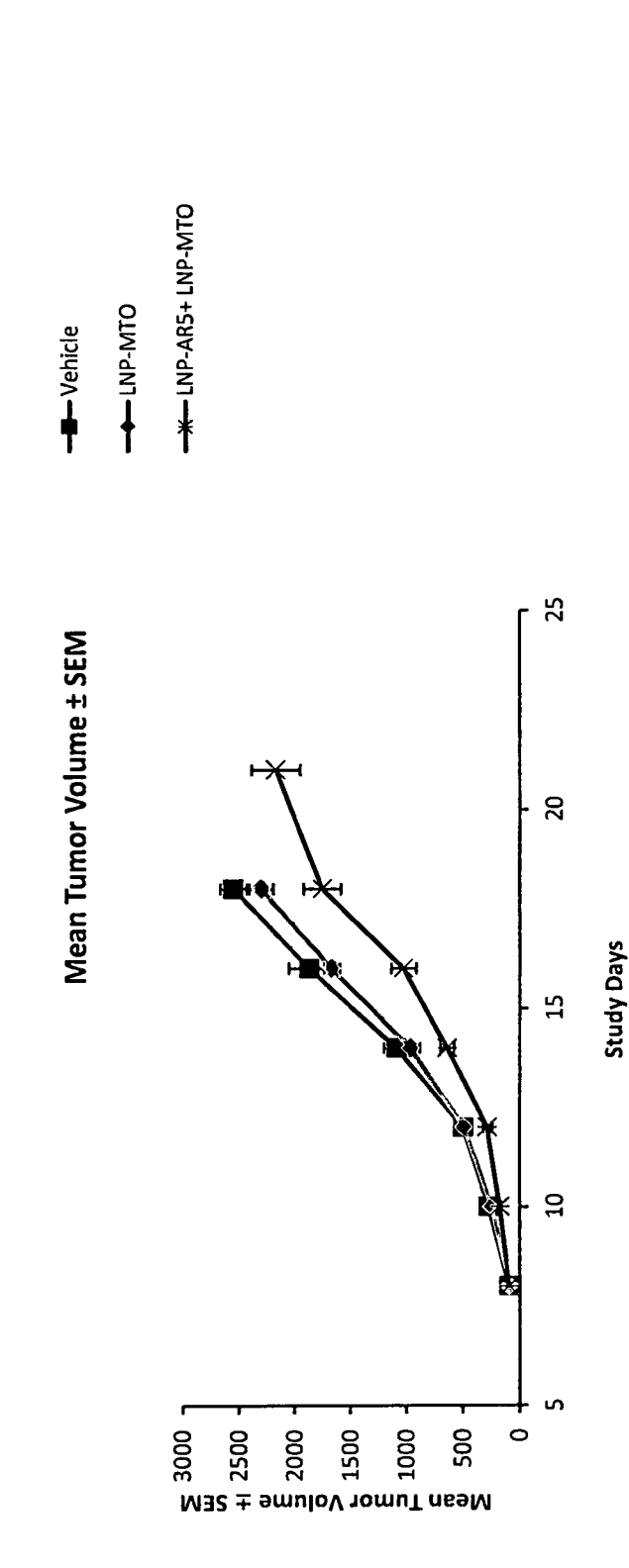
Figure 17. Tumor Inhibition of LNP-AR5 In Combination With LNP-MTO Using B16F10 Cells *In Vivo*

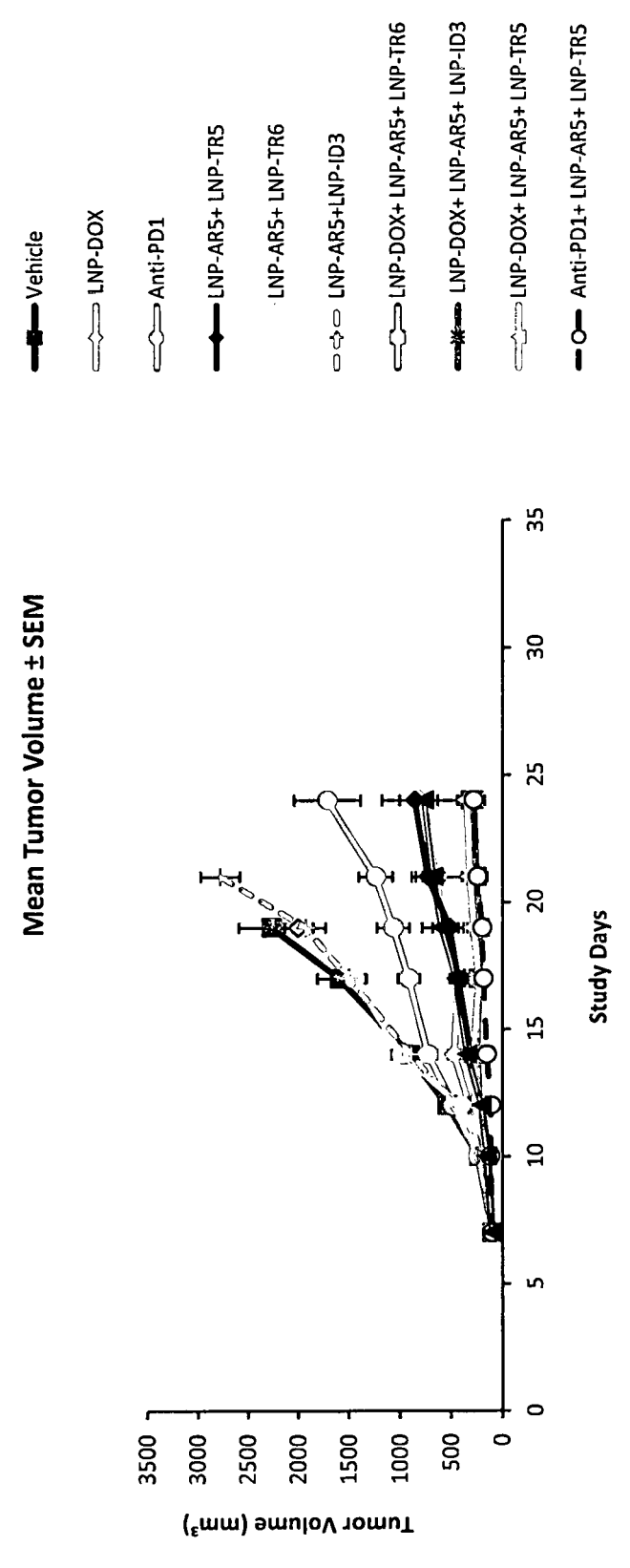
Figure 18. Tumor Inhibition of LNP-AR5 In Progressive Dosing with Multiple Combination(s) Using MC38 Cells *In Vivo*

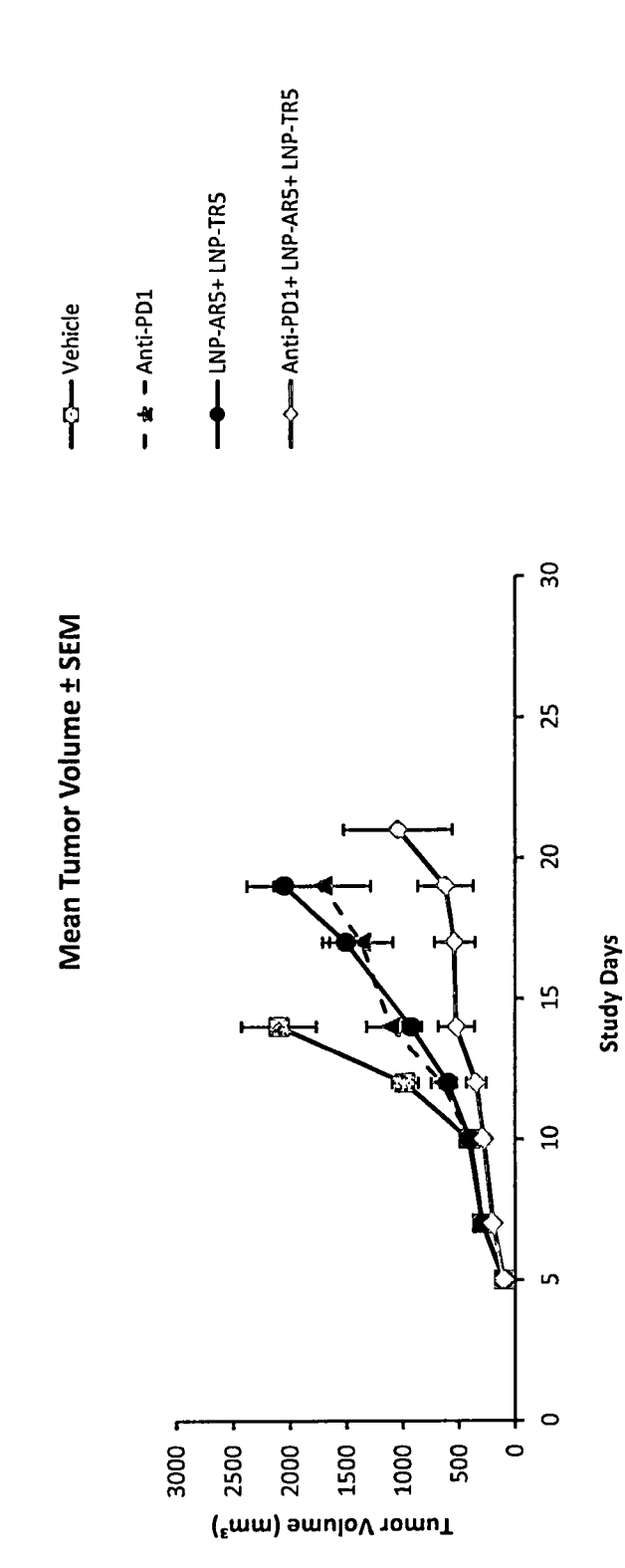
Figure 19. Tumor Inhibition of LNP-AR5 In Combination With LNP-TR5 and Anti-PD-1 Antibody Using H22 Cells *In Vivo*

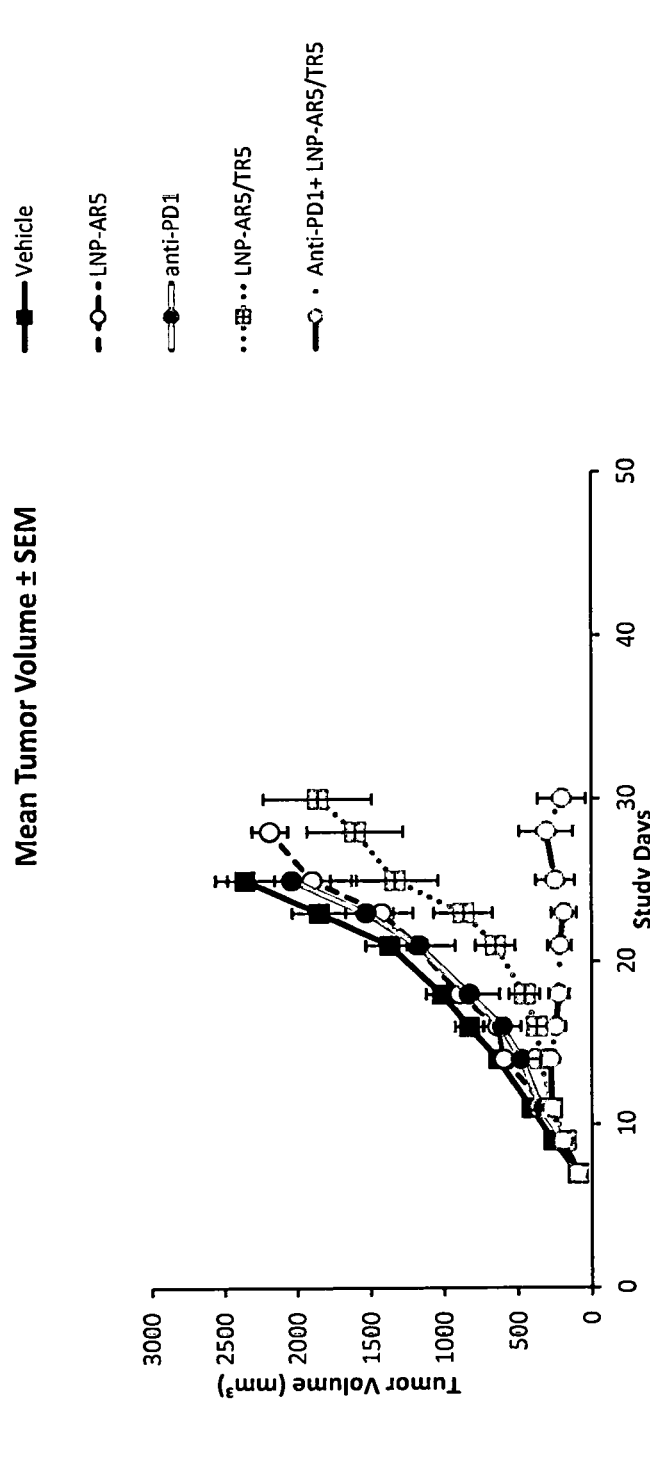
Figure 20. Tumor Inhibition of Co-Formulated LNP-AR5-TR5 In Combination With Anti-PD-1 Antibody Using EMT6 Cells *In Vivo*

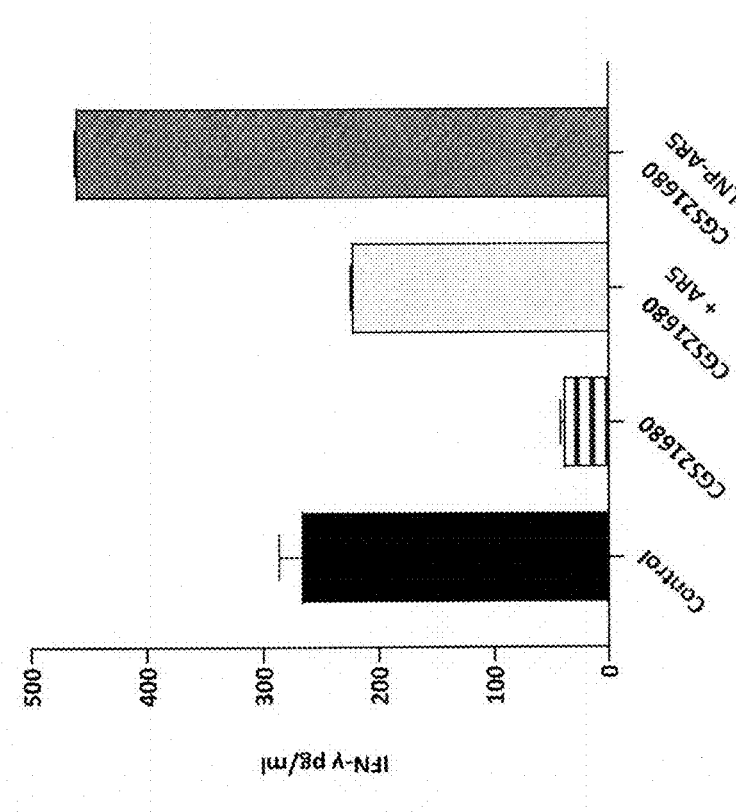
Figure 21. *Ex-vivo Validation of LNP-AR5 Mechanism of Action*

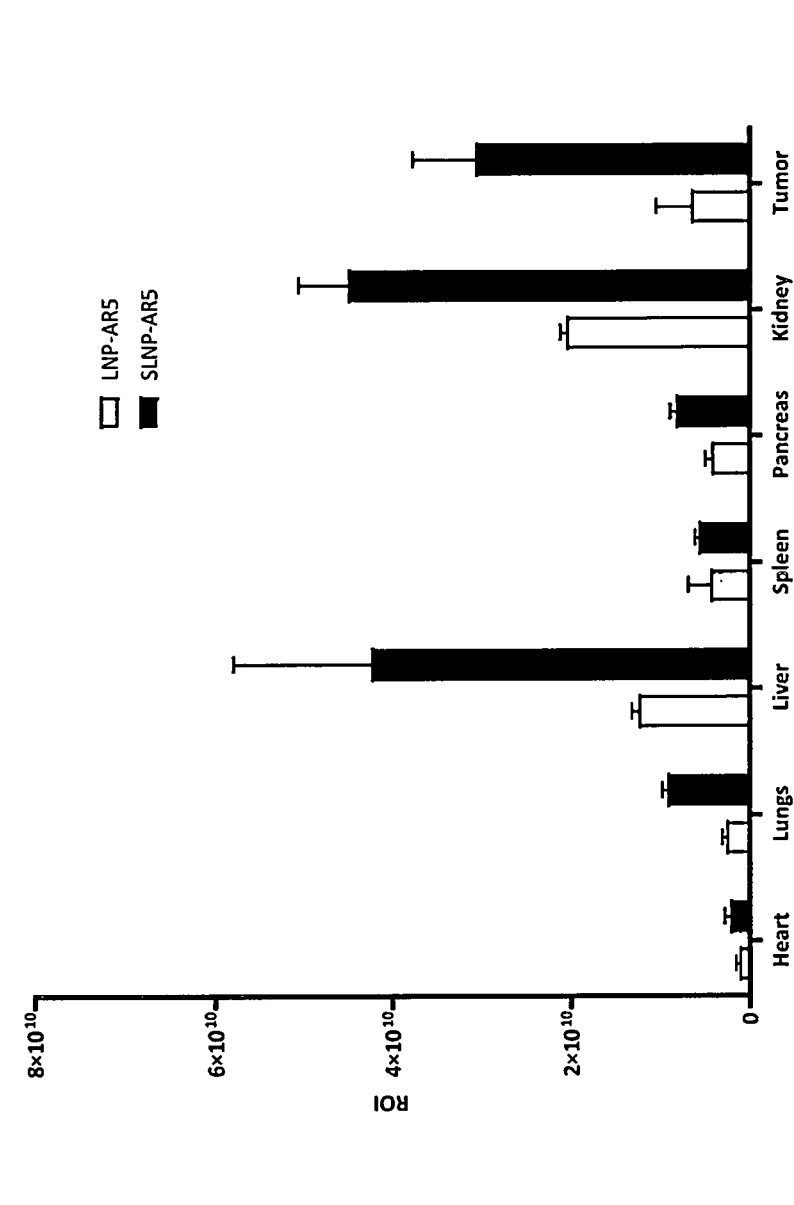
Figure 22. *Ex-vivo* Validation of LNP-AR5 and SLNP-AR5 Delivery to Tumor

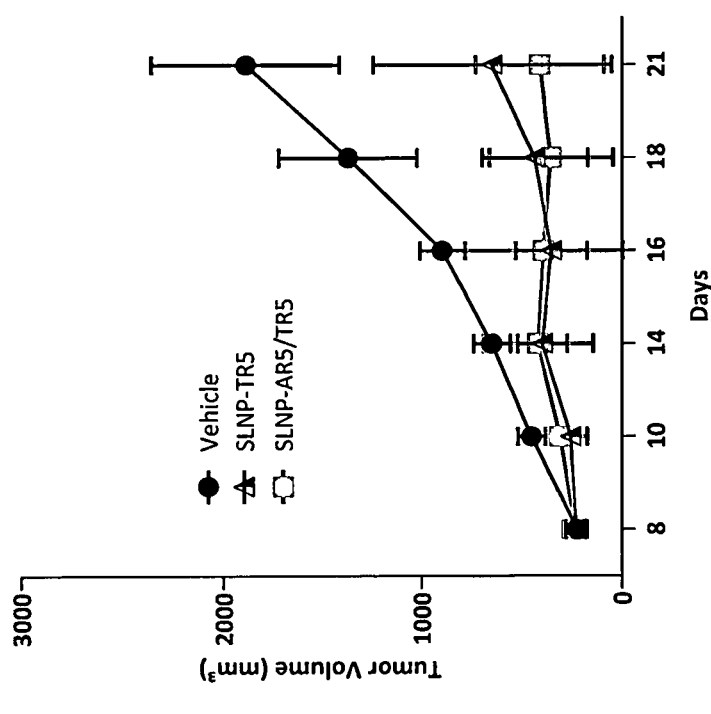
Figure 23. Tumor Inhibition of SLNP-AR5-TR5 In Combination with SLNP-TR5 Using EMT-6 Cells *In Vivo*.

Figure 24. Tumor Inhibition of Co-Formulated SLNP-AR5-ID3 and SLNP-AR5-DOX In Multiple Combinations with an Anti-PD-1 Antibody or Single Agent PD3 Using H22 Cells *In Vivo*.
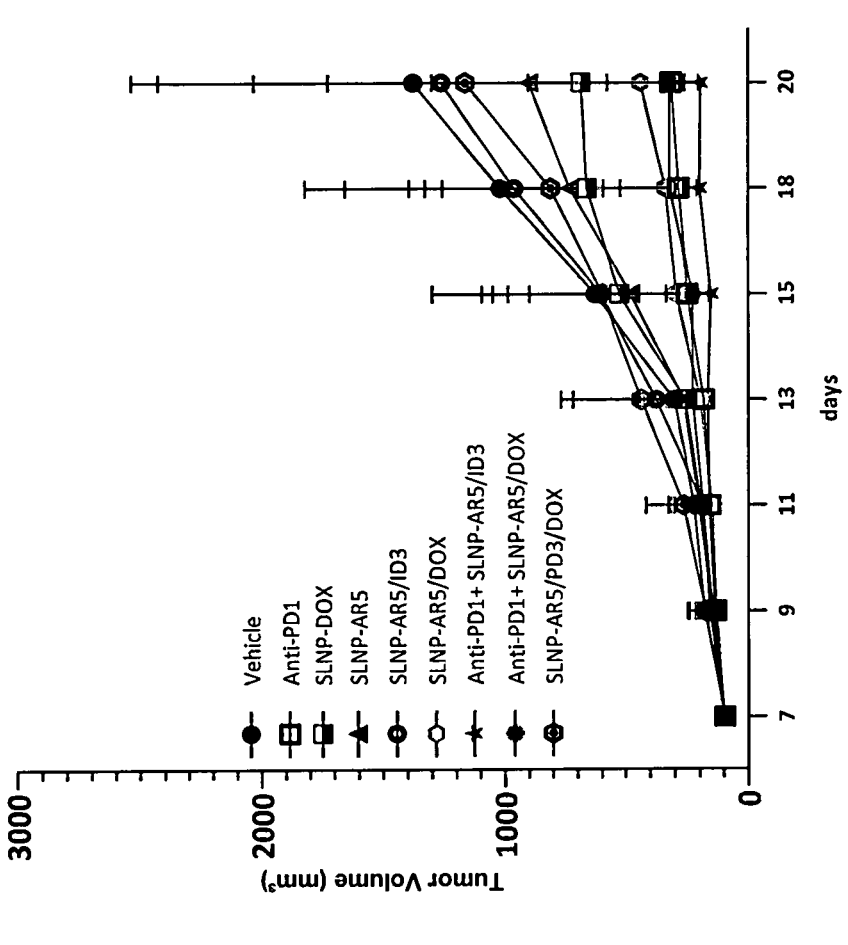

FORMULATED AND/OR CO-FORMULATED COMPOSITIONS CONTAINING A2aR ANTAGONIST PRODRUGS USEFUL IN THE TREATMENT OF CANCER AND METHODS THEREOF

CROSS-REFERENCE TO RELATED APPLICATIONS

This application claims priority to U.S. Provisional Patent Application No. 63/207,749 filed 18 Mar. 2021, the contents of which are fully incorporated by reference herein.

STATEMENT OF RIGHTS TO INVENTIONS MADE UNDER FEDERALLY SPONSORED RESEARCH

Not applicable.

FIELD OF THE INVENTION

The invention described herein relates to prodrug compositions that inhibit adenosine at the A2a receptor (A2aR) after release of the active inhibitor from the prodrug and nano-formulations comprising such prodrugs. Specifically, the invention relates to prodrug compositions which are formulated within a nanocarrier (e.g., a liposome) and used as a vehicle for cancer therapy in humans. The invention also relates to co-formulations of such prodrugs with other immune-modulating agents or prodrugs. The invention further relates to the treatment of cancers and other immunological disorders and diseases.

BACKGROUND OF THE INVENTION

Cancer is the second leading cause of death next to coronary disease worldwide. Millions of people die from cancer every year and in the United States alone cancer kills well over a half-million people annually, with 1,688,780 new cancer cases diagnosed in 2017 (American Cancer Society). While deaths from heart disease have been declining significantly, those resulting from cancer generally are on the rise. In the early part of the next century, cancer is predicted to become the leading cause of death unless medical developments change the current trend.

Several cancers stand out as having high rates of mortality. In particular, carcinomas of the lung (18.4% of all cancer deaths), breast (6.6% of all cancer deaths), colorectal (9.2% of all cancer deaths), liver (8.2% of all cancer deaths), and stomach (8.2% of all cancer deaths) represent major causes of cancer death for both sexes in all ages worldwide (GLOBOCAN 2018). These and virtually all other carcinomas share a common lethal feature in that they metastasis to sites distant from the primary tumor and with very few exceptions, metastatic disease fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients also experience physical debilitations following treatment. Furthermore, many cancer patients experience a recurrence of their disease.

Although cancer therapy has improved over the past decades and survival rates have increased, the heterogeneity of cancer still demands new therapeutic strategies utilizing a plurality of treatment modalities. This is especially true in treating solid tumors at anatomical crucial sites (e.g., glioblastoma, squamous carcinoma of the head and neck and lung adenocarcinoma) which are sometimes limited to standard radiotherapy and/or chemotherapy. Nonetheless, detrimental effects of these therapies are chemo- and radio resistance, which promote loco-regional recurrences, distant metastases and second primary tumors, in addition to severe side-effects that reduce the patients' quality of life.

The adenosine A2a receptor (A2aR) protein is a member of the G protein-coupled receptor (GPCR) family which possess seven transmembrane alpha helices, as well as an extracellular N-terminus and an intracellular C-terminus. Furthermore, located in the intracellular side close to the membrane is a small alpha helix, often referred to as helix 8 (H8). The crystallographic structure of the adenosine A2aR reveals a ligand binding pocket distinct from that of other structurally determined GPCRs (i.e., the beta-2 adrenergic receptor and rhodopsin). See, JAAKOLA, et. al., Science 322(5905): pp. 1211-1217 (November 2008). Below this primary (orthosteric) binding pocket lies a secondary (allosteric) binding pocket.

Adenosine initiates most of its physiological effects through the activation of four (4) G protein-coupled receptor (GPCR) subtypes; A1, A2A, A2B, and A3. These four receptor subtypes play a significant role in the regulation of a number of central nervous system functions, including pain, cerebral blood flow, basal ganglia operation, respiration, and sleep. The receptors primarily operate by coupling to the cyclic adenosine monophosphate (cAMP) second-messenger system, and the adenosine A2A receptor (A2AR) in particular is linked to $G_s$ and Golf proteins. Upon A2AR activation, the intracellular levels of cAMP are increased. See, JORG, et. al. Bioorg Med. Chem. Lett. (2013) 3427-3433. Generally, activation of A2aR or A2bR inhibits immune cells and thus adenosine acts as an immune checkpoint.

Various agents targeting A2aR are currently being evaluated as cancer therapies in over twenty (20) clinical trials. Generally, these trials intend to evaluate the safety associated with blockade of adenosine production (via CD73) or adenosine signaling (via A2aR) and the downstream effects on anti-tumor immunity. Several trials were designed to initially evaluate monotherapy, providing valuable insights into the single agent activity associated with adenosine blockade. Other trials moved directly into combination treatments along with anti-PD-L1, chemotherapy, and various targeted agents. See, WILLINGHAM, et. al. Curr. Opin. Pharmacology 53:126-133 (2020). The clinical teachings to date have led one of skill in the art to understand the following: (i) complete and prolonged inhibition of A2aR is well tolerated both as monotherapy and in combination with anti-PDL1 MAbs, (ii) A2aR antagonists have activity in multiple cancer indications, (iii) predictive biomarkers will identify patients most likely to benefit from adenosine pathway blockade.

Since adenosine signaling through A2aR serves as a negative regulator of the immune system, unique to this suppressive pathway is its ability to impact numerous stromal and immune cells. Teachings have highlighted the nature of negative regulators used in combination with other immune modulators, such as PD-L1, especially in patients who are refractory/resistant to prior anti-PD1/PDL1 therapy. See, HELMS, et. al, Curr. Opin. Pharmacology 53:77-83 (2020).

A prodrug is a medication or compound that, after administration, is metabolized (i.e., converted within the body) into a pharmacologically active drug. Instead of administering a drug directly, a corresponding prodrug is used instead to improve how a medicine is absorbed, distributed, metabolized, and/or excreted. Prodrugs are often designed to improve bioavailability when a drug itself is poorly absorbed from the gastrointestinal tract, for example. A prodrug may be used to improve how selectively the drug interacts with cells or processes that are not its intended target. This reduces adverse or unintended effects of a drug, especially important in treatments like chemotherapy, which can have severe unintended and undesirable side effects. Prodrugs can thus be viewed as drugs containing specialized non-toxic protective groups used in a transient manner to alter or to eliminate undesirable properties in the parent molecule.

Finally, a nanocarrier is a nanomaterial being used as a transport for another substance, such as a drug. There are many distinct types of nanocarriers. For example, nanocarriers include polymer conjugates, polymeric nanoparticles, lipid-based carriers, and dendrimers to name a few. Diverse types of nanomaterial(s) being used in nanocarriers allows for hydrophobic and hydrophilic drugs to be delivered throughout the body. Since the human body contains mostly water, the ability to deliver hydrophobic drugs effectively in humans is a major therapeutic benefit of nanocarriers. Nanocarriers show promise in the drug delivery process because they can deliver drugs to site-specific targets, allowing drugs to be delivered in certain organs or cells but not in others. Site-specificity is a major therapeutic benefit since it prevents drugs from being delivered to the wrong places. Additionally, nanocarriers show specific promise for use in chemotherapy because they can help decrease the adverse, broader-scale toxicity of chemotherapy on healthy, fast-growing cells around the body. Since chemotherapy drugs can be extremely toxic to human cells, it is important that they are delivered to the tumor without being released into other parts of the body.

From the aforementioned, it will be readily apparent to those skilled in the art that a new treatment paradigm is needed in the treatment of cancers and other immunological diseases. By using novel prodrugs in conjunction with modern nanocarrier modalities, a new disease treatment can be achieved with the overall goal of more effective treatment(s), reduced side effects, and greater therapeutic utility in the treatment of cancers, especially the treatment of cancers in solid tumors.

Given the current deficiencies associated with cancer treatment, it is an object of the present invention to provide new and improved methods of treating cancer(s), immunological disorders, and other diseases utilizing prodrugs encapsulated within a nanocarrier.

SUMMARY OF THE INVENTION

The invention provides for A2aR inhibitor prodrug ("AR Prodrug") compositions comprising an A2aR inhibitor agent, a lipid, and a biologically cleavable linker. In certain embodiments, nanocarriers comprising an AR Prodrug are formulated for use as a delivery modality to treat human diseases such as cancer, including solid tumor cancers as well as other immunological disorders. In certain embodiments, the nanocarriers comprise a lipid-bilayer capable of being incorporated into a drug delivery vehicle (i.e., a liposome). In a further embodiment, the nanocarrier comprises a solid-lipid nanoparticle ("SLNP"). In a further preferred embodiment, the liposome comprises cholesterol hemisuccinate ("CHEMS"). In a further preferred embodiment, the liposome of the invention comprises Stearic Acid.

In a further embodiment, an AR Prodrug of the disclosure comprises an AR5-Prodrug.

In a further embodiment, the invention comprises methods of delivering an A2aR inhibitor to a tumor comprising (i) synthesizing an AR Prodrug; (ii) formulating an AR Prodrug of the invention in a nanocarrier of the invention; and (iii) administering the nanocarrier to a patient.

In another embodiment, the invention comprises methods of delivering an A2aR inhibitor with one or more additional immune modulating agent to a tumor comprising (i) synthesizing an AR Prodrug; (ii) co-formulating an AR Prodrug of the invention in a nanocarrier with one or more additional immune modulating agents of the invention; and (iii) administering the nanocarrier to a patient.

In another embodiment, the immune modulating agents comprise immunogenic-cell death inducing chemotherapeutics, PD-1 antagonists, toll receptor agonists, STING agonists, IDO inhibitors, CTLA4 inhibitors, CD1D agonists, TGFβ inhibitors, and/or prodrugs thereof.

In another embodiment, the present disclosure teaches methods of synthesizing AR Prodrugs.

In another embodiment, the present disclosure teaches methods of synthesizing an AR5-Prodrug.

In another embodiment, the present disclosure teaches methods of formulating AR Prodrugs within nanocarriers, including but not limited to liposomes.

In another embodiment, the present disclosure teaches methods of formulating an AR5 Prodrug within nanocarriers, including but not limited to liposomes.

In another embodiment, the present disclosure teaches methods of formulating an AR5 Prodrug within nanocarriers, including but not limited to SLNPs.

In another embodiment, the present disclosure teaches methods of treating cancer(s), immunological disorders and other diseases in humans using nanocarriers of the present disclosure.

BRIEF DESCRIPTION OF THE FIGURES

FIG. 1. Chemical Synthesis for AR5-Prodrug.

FIG. 2. A2aR Inhibitor Prodrug Synthesis Schema with Carboxylic Acid Functionality.

FIG. 3. A2aR Inhibitor Prodrug Synthesis Schema with Alcohol Functionality.

FIG. 4. A2aR Inhibitor Prodrug Synthesis Schema with Secondary Amine, Amide, or Aniline Functionality.

FIG. 5. Characterization of LNP-AR5 Liposome.

FIG. 6. Characterization of LNP-AR5 Liposome (Zeta Potential).

FIG. 7. Characterization of LNP-AR5-TR5 Liposome.

FIG. 8. Characterization of LNP-AR5-TR5 Liposome (Zeta Potential).

FIG. 9. Characterization of LNP-AR5-ID3 Liposome.

FIG. 10. Characterization of LNP-AR5-ID3 Liposome (Zeta Potential).

FIG. 11. Characterization of LNP-AR5-TR5-ID3 Liposome.

FIG. 12. Characterization of LNP-AR5-TR5-ID3 Liposome (Zeta Potential).

FIG. 13. Characterization of SLNP-AR5 Solid-Lipid Nanocarrier.

FIG. 14. Characterization of SLNP-AR5 (Zeta Potential).

FIG. 15. Characterization of SLNP-AR5-TR5 Solid-Lipid Nanocarrier.

FIG. 16. Characterization of SLNP-AR5-TR5 (Zeta Potential).

FIG. 17. Tumor Inhibition of LNP-AR5 In Combination With LNP-MTO Using B16F10 Cells In Vivo.

FIG. 18. Tumor Inhibition of LNP-AR5 In Progressive Dosing with Multiple Combination(s) Using MC38 Cells In Vivo.

FIG. 19. Tumor Inhibition of LNP-AR5 In Combination With LNP-TR5 and Anti-PD-1 Antibody Using H22 Cells In Vivo.

FIG. 20. Tumor Inhibition of Co-Formulated LNP-AR5/ TR5 In Combination with Anti-PD-1 Antibody Using EMT6 Cells In Vivo.

FIG. 21. Ex Vivo Validation of LNP-AR5 Mechanism of Action.

FIG. 22. Ex Vivo Validation of LNP-AR5 and SLNP-AR5 Delivery to Tumor.

FIG. 23. Tumor Inhibition of SLNP-AR5-TR5 in Combination with SLNP-TR5 using EMT-6 Cells In Vivo.

FIG. 24. Tumor Inhibition of Co-Formulated SLNP-AR5-ID3 and SLNP-AR5-DOX In Multiple Combinations with an Anti-PD-1 Antibody or Single Agent PD3 Using H22 Cells In Vivo.

DETAILED DESCRIPTION OF THE INVENTION

Outline of Sections

I.) Definitions
II.) Prodrugs
II.) Chemical Compounds
IV.) Lipids
V.) Linkage Unit(s) ("LU")
VI.) Nanocarriers
VII.) Liposomes
VIII.) Pharmaceutical Formulation
IX.) Combination Therapy
X.) Methods of Delivering Liposomes Comprising Prodrugs to a Cell
XI.) Methods of Treating Cancer(s) and Other Immunological Disorder(s)
XII.) KITS/Articles of Manufacture

I.) Definitions

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art.

When a trade name is used herein, reference to the trade name also refers to the product formulation, the generic drug, and the active pharmaceutical ingredient(s) of the trade name product, unless otherwise indicated by context.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and sub combinations of A, B, C, and D.

Numerical ranges recited herein by endpoints include all numbers and fractions subsumed within that range (e.g., 1 to 5 includes, but is not limited to, 1, 1.5, 2, 2.75, 3, 3.90, 4, and 5).

As used herein, the phrase "consisting essentially of" limits the scope of a claim to the specified materials or steps, plus those that do not materially affect the basic and novel characteristic(s) of the claimed subject matter.

The terms "advanced cancer", "locally advanced cancer", "advanced disease" and "locally advanced disease" mean cancers that have extended through the relevant tissue capsule and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease and these patients have substantially less favorable outcomes compared to patients having clinically localized (organ-confined) cancer.

As used herein the term "alkyl" can refer to $C_1$-$C_{20}$ inclusive, linear (i.e., "straight-chain"), branched, or cyclic, saturated, or at least partially and in some cases unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl, or propyl, is attached to a linear alkyl chain. "Lower alkyl" refers to an alkyl group having 1 to about 8 carbon atoms (i.e., a $C_1$-$C_8$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_1$-$C_8$ straight-chain alkyls. In other embodiments, "alkyl" refers, in particular, to $C_{i-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered aromatic and heteroaromatic rings. The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl. Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc.) in the backbone of a ring structure. Nitrogen-containing heteroaryl moieties include, but are not limited to, pyridine, imidazole, benzimidazole, pyrazole, pyrazine, triazine, pyrimidine, and the like.

The terms "anticancer drug", "chemotherapeutic", and "anticancer prodrug" refer to drugs (i.e., chemical compounds) or prodrugs known to, or suspected of being able to treat a cancer (i.e., to kill cancer cells, prohibit proliferation of cancer cells, or treat a symptom related to cancer). In some embodiments, the term "chemotherapeutic" as used herein refers to a non-PS molecule that is used to treat cancer and/or that has cytotoxic ability. More traditional or conventional chemotherapeutic agents can be described by mechanism of action or by chemical compound class, and can include, but are not limited to, alkylating agents (e.g., melphalan), anthracyclines (e.g., doxorubicin), cytoskeletal disruptors (e.g., paclitaxel), epothilones, histone deacetylase inhibitors (e.g., vorinostat), inhibitors of topoisomerase I or II (e.g., irinotecan or etoposide), kinase inhibitors (e.g., bortezomib), nucleotide analogs or precursors thereof (e.g., methotrexate), peptide antibiotics (e.g., bleomycin), platinum based agents (e.g., cisplatin or oxaliplatin), retinoids (e.g., tretinoin), and vinka alkaloids (e.g., vinblastine).

"Aralkyl" refers to an -alkyl-aryl group, optionally wherein the alkyl and/or aryl moiety is substituted.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched, or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)3-); cyclohexylene (—C$_6$H$_{10}$—); —CH=CH—CH=CH—; —CH=CH—CH$_2$—; —(CH$_2$)$_q$—N(R)—(CH$_2$)—, wherein each of q is an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxy (—O—CH$_2$—

8

O—); and ethylenedioxy (—O—(CH$_2$)$_2$—O—). An alkylene group can have about 2 to about 3 carbon atoms and can further have 6-20 carbons.

The term "arylene" refers to a bivalent aromatic group, e.g., a bivalent phenyl or napthyl group. The arylene group can optionally be substituted with one or more aryl group substituents and/or include one or more heteroatoms.

The term "amino" refers to the group —N(R)$_2$ wherein each R is independently H, alkyl, substituted alkyl, aryl, substituted aryl, aralkyl, or substituted aralkyl. The terms "aminoalkyl" and "alkylamino" can refer to the group —N(R)$_2$ wherein each R is H, alkyl, or substituted alkyl, and wherein at least one R is alkyl or substituted alkyl. "Arylamine" and "aminoaryl" refer to the group —N(R)$_2$ wherein each R is H, aryl, or substituted aryl, and wherein at least one R is aryl or substituted aryl, e.g., aniline (i.e., —NHC$_6$H$_5$).

"Bulk" (a.k.a. Drug Substance) means the drug substance or the drug product which has not been filled into final containers for distribution. Final formulated bulk generally refers to drug product which is formulated and being stored or held prior to filling. Drug substance may be stored or held as "bulk" or "concentrated bulk" prior to formulation into drug product.

The terms "carboxylate" and "carboxylic acid" can refer to the groups —C(=O)O— and —C(=O)OH, respectively. The term "carboxyl" can also refer to the —C(=O)OH group.

The terms "conjugate" and "conjugated" as used herein can refer to the attachment (e.g., the covalent attachment) of two or more components (e.g., chemical compounds, polymers, biomolecule, particles, etc.) to one another. In some embodiments, a conjugate can comprise monovalent moieties derived from two different chemical compounds covalently linked via a bivalent linker moiety (e.g., an optionally substituted alkylene or arylene). In some embodiments, the linker can contain one or more biodegradable bond, such that one or more bonds in the linker can be broken when the prodrug is exposed to a particular physiological environment or enzyme (for example, esterases).

The term "compound" refers to and encompasses the chemical compound (e.g. a prodrug) itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and/or solvates; however, this reference is for emphasis only, and is not to be construed as excluding other of the above forms as identified above.

"Drug product" means a final formulation that contains an active drug ingredient (i.e., liposomes containing A2aR inhibitor prodrugs) generally, but not necessarily, in association with inactive ingredients. The term also includes a finished dosage form that does not contain an active ingredient but is intended to be used as a placebo.

The term "disulfide" can refer to the —S—S— group.

The term "empty vesicle" means an unloaded lipid vesicle by itself.

The term "ester" as used herein means a chemical compound derived from acid (organic or inorganic) in which at least one-OH hydroxyl group is replaced by an —O-alkyl (alkoxy) or O-Aryl (aryloxy) group.

The term "esterase" as used herein is a hydrolase enzyme that splits esters into an acid and an alcohol.

"Excipient" means an inactive substance used as a carrier for the active ingredients in a drug such as vaccines. Excipients are also sometimes used to bulk up formulations with very potent active ingredients, to allow for convenient and accurate dosage. Examples of excipients include but are not limited to, anti-adherents, binders, coatings, disintegrants, fillers, diluents, flavors, colors, lubricants, and preservatives.

The terms "halo", "halide", or "halogen" as used herein refer to fluoro, chloro, bromo, and iodo groups.

The terms "hydroxyl" and "hydroxy" refer to the —OH group.

The terms "inhibit" or "inhibition of" as used herein means to reduce by a measurable amount, or to prevent entirely.

The terms "individual" or "patient," as used in the context of this disclosure can be used interchangeably.

As used herein, the term "ligand" refers generally to a species, such as a molecule or ion, which interacts, e.g., binds, in some way with another species. See Martell, A. E., and Hancock, R. P., Metal Complexes in Aqueous Solutions, Plenum: New York (1996), which is incorporated herein by reference in its entirety.

The term "lipid" as used herein refers to a class of naturally occurring. (organic) compounds that are insoluble in polar solvents. In the context of the disclosure, a lipid refers to conventional lipids, phospholipids, cholesterol, chemically functionalized lipids for attachment of PEG and ligands, etc.

The term "lipid bilayer" or "LB" refers to any double layer of oriented amphipathic lipid molecules in which the hydrocarbon tails face inward to form a continuous nonpolar phase.

The term(s) "liposome" or "lipid vesicle" or "vesicle" are used interchangeably to refer to an aqueous compartment enclosed by a lipid bilayer, as being conventionally defined (see, STRYER (1981) Biochemistry, 2d Edition, W. H. Freeman & Co., p. 213).

The term "mammal" refers to any organism classified as a mammal, including mice, rats, rabbits, dogs, cats, cows, horses, and humans. In one embodiment of the invention, the mammal is a mouse. In another embodiment of the invention, the mammal is a human.

The terms "mercapto" or "thiol" refer to the —SH group.

The terms "metastatic cancer" and "metastatic disease" mean cancers that have spread to regional lymph nodes or to distant sites and are meant to include stage D disease under the AUA system and stage T×N×M+ under the TNM system.

The terms "nanocarrier," "nanoparticle, and "nanoparticle drug carrier" are used interchangeably and refer to a nano-structure having an aqueous, solid, or polymeric interior core. In certain embodiments the nanocarrier comprises a lipid bilayer encasing (or surrounding or enveloping) the porous particle core. In certain embodiments the nanocarrier is a liposome, lipid nanoparticle ("LNP") or a solid-lipid nanoparticle ("SLNP").

The terms "nanoscale particle," "nanomaterial," "nanocarrier," and "nanoparticle" refer to a structure having at least one region with a dimension (e.g., length, width, diameter, etc.) of less than about 1,000 nm. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm). In some embodiments, the dimension is between about 20 nm and about 250 nm (e.g., about 20, 30, 40, 50, 60, 70, 80, 90, 100, 110, 120, 130, 140, 150, 160, 170, 180, 190, 200, 210, 220, 230, 240, or 250 nm).

The term "nanovesicle" refers to a "lipid vesicle" having a diameter (or population of vesicles having a mean diameter) ranging from about 20 nm, or from about 30 nm, or from about 40 nm, or from about 50 nm up to about 500 nm, or up to about 400 nm, or up to about 300 nm, or up to about 200 nm, or up to about 150 nm, or up to about 100 nm, or up to about 80 nm. In certain embodiments a nanovesicle has a diameter ranging from about 40 nm up to about 80 nm, or from about 50 nm up to about 70 nm.

"Pharmaceutically acceptable" refers to a non-toxic, inert, and/or composition that is physiologically compatible with humans or other mammals.

"Pharmaceutical formulation" means the process in which different chemical substances are combined to a pure drug substance to produce a final drug product.

The term "phosphonate" refers to the —P($=$O)(OR)$_2$ group, wherein each R can be independently H, alkyl, aralkyl, aryl, or a negative charge (i.e., wherein effectively there is no R group present to bond to the oxygen atom, resulting in the presence of an unshared pair of electrons on the oxygen atom). Thus, stated another way, each R can be present or absent, and when present is selected from H, alkyl, aralkyl, or aryl.

The term "phosphate" refers to the —OP($=$O)(OR')$_2$ group, where R' is H or a negative charge.

The term "prodrug" means a medication or compound that, after administration, is metabolized into a pharmacologically active drug. For the purposes of this disclosure, a prodrug of the invention comprises three (3) components: (i) a drug moiety; (ii) a lipid moiety; and (iii) a linkage unit ("LU").

The term "AR Prodrug" means a prodrug of the inventions wherein the drug moiety comprises an A2aR inhibitor.

The term "pyrolipid" or "pyro lipid" refers to a conjugate of a lipid and a porphyrin, porphyrin derivative, or porphyrin analog. In some embodiments, the pyrolipid can comprise a lipid conjugate wherein a porphyrin or a derivative or analog thereof is covalently attached to a lipid side chain. See, for example U.S. Patent Application Publication No. 2014/0127763.

As used herein, the terms "specific," "specifically binds" and "binds specifically" refer to the selective binding of nanocarrier of the invention to the target A2aR or related family member.

The term "supported lipid bilayer" means a lipid bilayer enclosing a porous particle core. This definition as set forth in the disclosure is denoted because the lipid bilayer is located on the surface and supported by a porous particle core. In certain embodiments, the lipid bilayer can have a thickness ranging from about 6 nm to about 7 nm which includes a 3-4 nm thickness of the hydrophobic core, plus the hydrated hydrophilic head group layers (each about 0.9 nm) plus two partially hydrated regions of about 0.3 nm each. In various embodiments, the lipid bilayer surrounding the liposome comprises a continuous bilayer or substantially continuous bilayer that effectively envelops and seals the A2aR inhibitor.

The term "thioalkyl" can refer to the group-SR, wherein R is selected from H, alkyl, substituted alkyl, aralkyl, substituted aralkyl, aryl, and substituted aryl. Similarly, the terms "thioaralkyl" and "thioaryl" refer to —SR groups wherein R is aralkyl and aryl, respectively.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act.

The term "therapeutically effective amount" refers to the amount of active prodrug, nano-encapsulated prodrug, or pharmaceutical agent that elicits the biological or medicinal response in a tissue, system, animal, individual or human.

The term "unsupported lipid bilayer" means an uncoated lipid bilayer in a lipid vesicle or liposome.

II.) Prodrugs

As shown in the present disclosure and for the purposes of this invention, a suitable prodrug is formed by conjugating a drug moiety of the invention (See, section entitled Drug Moieties) to a lipid moiety of the invention (See, section entitled Lipids) via an LU (See, section entitled Linkage Units) of the present disclosure. For the purposes of this disclosure, formation of an AR Prodrug can utilize several strategies. (See, for example, FIG. 2, FIG. 3, and FIG. 4).

Accordingly, in some embodiments, the prodrug is a drug-lipid moiety comprising an A2aR inhibitor of the disclosure.

In one embodiment, the prodrug comprises the following chemical structure denoted Formula I:

FORMULA I

Wherein, in exemplary embodiments of FORMULA I:
X=O, NH; and

Thus, in one embodiment, the prodrug is a drug-lipid moiety comprising an A2aR Inhibitor of FORMULA I.

In one embodiment, the prodrug is a drug-lipid moiety comprising an A2aR inhibitor set forth in FIG. 2.

Figure 3:
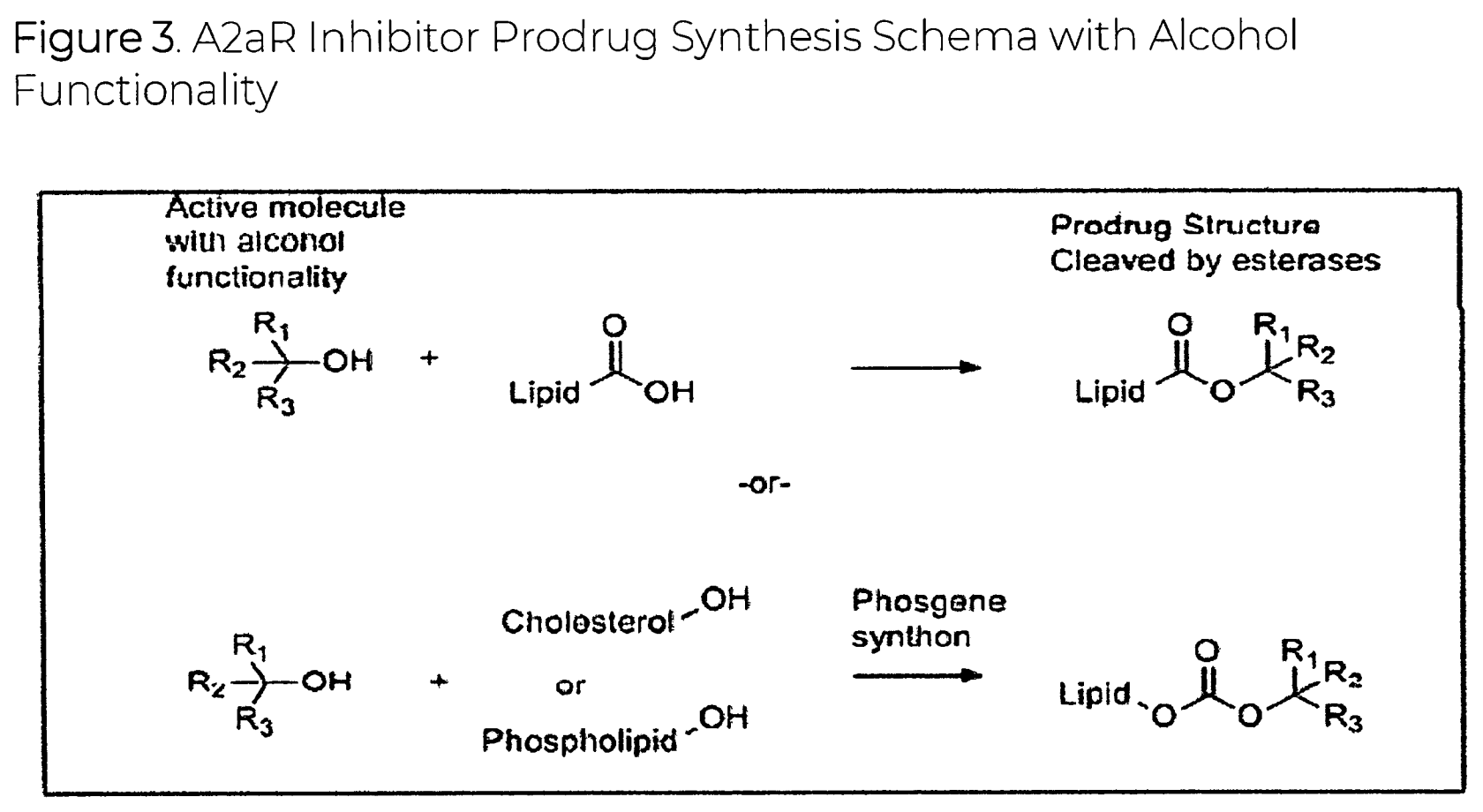

In one embodiment, the prodrug is a drug-lipid moiety comprising an A2aR Inhibitor set forth In FIG. 3.

Figure 4:
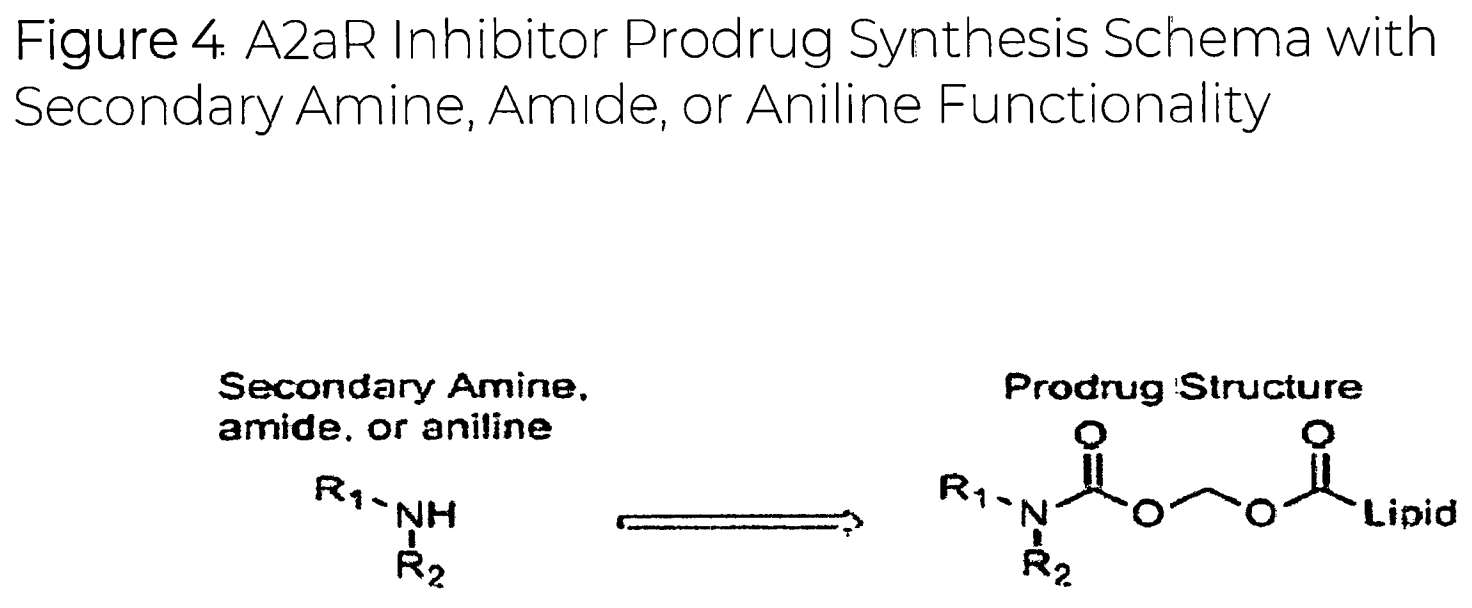

In one embodiment, the prodrug is a drug-lipid moiety comprising an A2aR inhibitor set forth in FIG. 4.

In a further embodiment, the AR Prodrug Is a drug-lipid moiety comprising a lipid of the disclosure.

In a further embodiment, the AR Prodrug is a drug-lipid moiety whereby the lipid is CHEMS.

In a further embodiment, the AR Prodrug is a drug-lipid moiety whereby the lipid is Stearic Acid.

In a further embodiment, the AR Prodrug is a drug-lipid moiety comprising a LU of the disclosure.

In a further embodiment, the AR Prodrug is a drug-lipid moiety whereby the LU is a hydromethylcarbamate linker.

In a further embodiment, the prodrug is a drug-lipid moiety comprising an A2aR inhibitor of the invention, wherein the A2aR inhibitor comprises the chemical composition(s) denoted AR5.

In a further embodiment, the prodrug is a drug-lipid moiety comprising an A2aR inhibitor of the invention, wherein the A2aR inhibitor comprises AR5 and has the following chemical structure:

In a further embodiment, the prodrug is a drug-lipid moiety comprising an A2aR inhibitor of the invention, wherein the A2aR inhibitor comprises AR5 and further comprises a lipid of the disclosure having the following chemical formula:

("AR5-Prodrug")

In a further embodiment, the prodrug is a drug-lipid moiety comprising an A2aR inhibitor of the invention, wherein the A2aR inhibitor comprises AR5 and further comprises CHEMS.

In a further embodiment, the prodrug is a drug-lipid moiety comprising an A2aR inhibitor of the invention, wherein the A2aR inhibitor comprises AR5 and further comprises Stearic Acid.

In a further embodiment, the prodrug is a drug-lipid moiety comprising an A2aR inhibitor of the invention, wherein the A2aR inhibitor comprises AR5 and further comprises CHEMS and whereby the LU is a hydromethyl-carbamate linker.

In a further embodiment, the prodrug is a drug-lipid moiety comprising an A2aR inhibitor of the invention, wherein the A2aR inhibitor comprises AR5 and further comprises Stearic Acid and whereby the LU is a hydromethylcarbamate linker.

In a further embodiment, the prodrug is a drug-lipid moiety comprising an A2aR inhibitor of the invention, wherein the A2aR inhibitor comprises AR5 and further comprises Stearic Acid having the following structure:

In additional embodiments of the disclosure the subject matter provides an A2aR inhibitor prodrug comprising a lipid-conjugated therapeutic agent parent drug. In some embodiments, the prodrug comprises: (a) a monovalent drug moiety, (b) a monovalent lipid moiety, and (c) a bivalent linker moiety comprising a linkage unit that will degrade in vivo, such as a disulfide bond, wherein the monovalent drug moiety and the monovalent lipid moiety are linked (e.g., covalently linked) through the linker. The monovalent drug moiety and the monovalent lipid moieties can be monovalent derivatives of a chemical compound and a lipid, respectively. For instance, the monovalent derivative can be a deprotonated derivative of a chemical compound or lipid that comprises a hydroxyl, thiol, amino, or carboxylic acid group.

In further embodiments of the disclosure the subject matter provides an A2aR inhibitor prodrug comprising a lipid-conjugated therapeutic agent parent drug. In some embodiments, the prodrug comprises: (a) a bivalent drug moiety, (b) a bivalent lipid moiety, and (c) a bivalent linker moiety comprising a linkage that will degrade in vivo, wherein the bivalent drug moiety and the bivalent lipid moiety are linked (e.g., covalently linked) through the linker. The bivalent drug moiety and the bivalent lipid moieties can be bivalent derivatives of a chemical compound and a lipid, respectively. For instance, the bivalent derivative can be a deprotonated derivative of a chemical compound or lipid that comprises a hydroxyl, thiol, amino, or carboxylic acid group.

One of ordinary skill in the art will appreciate and be enabled to make variations and modifications to the disclosed embodiment without altering the function and purpose of the invention disclosed herein. Such variations and modifications are intended within the scope of the present disclosure.

III.) Drug Moieties

Another aspect of the invention provides for novel AR Prodrug compound(s) comprising an A2aR inhibitor with the following formula(s) denoted AR5.

One of skill in the art will appreciate that a compound is useful as an A2aR signaling inhibitor (e.g., inhibits A2aR and other family members). By way of brief background, the adenosine A2a receptor, also known as ADORA2A, is an adenosine receptor. This protein is a member of the G protein-coupled receptor (GPCR) family which possess seven transmembrane alpha helices, as well as an extracellular N-terminus and an intracellular C-terminus. Furthermore, located in the intracellular side close to the membrane is a small alpha helix, often referred to as helix 8 (H8). The crystallographic structure of the adenosine $A_{2A}$ receptor reveals a ligand binding pocket distinct from that of other structurally determined GPCRs (i.e., the beta-2 adrenergic receptor and rhodopsin). The gene encodes a protein which is one of several receptor subtypes for adenosine. The activity of the encoded protein, a G protein-coupled receptor family member, is mediated by G proteins which activate adenylyl cyclase, which induce synthesis of intracellular cAMP. The $A_{2A}$ receptor binds with the $G_s$ protein at the intracellular site of the receptor. See, CARPENTER, et. al., Structure of the Adenosine A2a Receptor Bound to an Engineered G Protein, Nature 536(7614): pp. 104-107 (4 Aug. 2016). The encoded protein (the $A_{2A}$ receptor) is abundant in basal ganglia, vasculature, T lymphocytes, and platelets and it is a major target of caffeine, which is a competitive antagonist of this protein. Additionally, $A_1$ and $A_{2A}$ receptors are believed to regulate myocardial oxygen demand and to increase coronary circulation by vasodilation. In addition, $A_{2A}$ receptor can suppress immune cells, thereby protecting tissue from inflammation. See, OHTA, et. al., Role of G-protein-coupled adenosine receptors in down-regulation of inflammation and protection from tissue damage, Nature, vol. 414 20/27 (December 2001). The $A_{2A}$ receptor is also expressed in the brain, where it has important roles in the regulation of glutamate and dopamine release, making it a potential therapeutic target for the treatment of conditions such as insomnia, pain, depression, and Parkinson's disease. See, SCHIFFMANN, et. al., Adenosine A2a Receptors and Basal Ganglia Physiology, Prog. Neurobiol., 83(5): 277-292 (December 2007).

Based on the foregoing, the present disclosure describes a class of A2aR inhibitors.

In one embodiment, a drug moiety of the disclosure comprises a compound with the following chemical structure (denoted AR1):

AR1

In one embodiment, a drug moiety of the disclosure comprises a compound with the following chemical structure (denoted AR2):

AR2

In one embodiment, a drug moiety of the disclosure comprises a compound with the following chemical structure (denoted AR3):

AR3

In one embodiment, a drug moiety of the disclosure comprises a compound with the following chemical structure (denoted AR4):

AR4

In one embodiment, a drug moiety of the disclosure comprises a compound with the following chemical structure (denoted AR5):

AR5

One of ordinary skill in the art will appreciate and be enabled to make variations and modifications to the disclosed embodiment without altering the function and purpose of the invention disclosed herein. Such variations and modifications are intended within the scope of the present disclosure.

IV.) Lipids

Generally speaking, and for the purposes of this disclosure, the term "lipid" is used in its broadest sense and comprises several sub-categories of lipids, including but not limited to, phospholipids/fatty acids. As it is appreciated by one of skill in the art, a phospholipid represents a class of lipids that are a major component of all cell membranes. Phospholipids can form lipid bilayers because of their amphiphilic characteristic. The structure of the phospholipid molecule generally consists of two hydrophobic fatty acid "tails" and a hydrophilic "head" consisting of a phosphate group that can be modified with simple organic molecules such as choline, ethanolamine, or serine. These two components are usually joined together by a glycerol molecule. A representative list of phospholipids/fatty acid(s) of the invention are set forth in Table III.

By way of brief background, at the most fundamental level, the properties of a liposome depend upon the subtle physicochemical interactions among the various lipid species in its composition. Individual lipids can be combined to form a myriad of superstructures including bilayers, and bilayer properties can be tuned to modulate drug release and membrane stability. In a simplified bilayer model acyl chain length dictates bilayer thickness and phase transition temperature (Tm), acyl chain saturation controls bilayer fluidity, and headgroup interactions impact inter- and intra-lipid molecular forces. Liposome behavior can be adjusted by incorporating synthetic lipids such as lipid prodrugs, fusogenic lipids and functionalize-able lipids into the bilayer. See, KOHLI, et. al., J. Control Release, 0: pp. 274-287 (Sep. 28, 2014).

In one embodiment of the present disclosure, an AR Prodrug comprises a monovalent lipid moiety.

In one embodiment, an AR Prodrug comprises a bivalent lipid moiety.

In one embodiment, the lipid comprises a cholesterol with the following chemical structure:

In one embodiment, the lipid comprises a DPPG with the following chemical structure:

In one embodiment, the lipid comprises a DMPG with the following chemical structure:

In one embodiment, the lipid comprises a Lyso PC with the following chemical structure:

In one embodiment, the lipid comprises a (Δ9-Cis) PG with the following chemical structure:

In one embodiment, the lipid comprises a Soy Lyso PC with the following chemical structure:

In one embodiment, the lipid comprises a PG with the following chemical structure:

In one embodiment, the lipid comprises a C16 PEG2000 Ceramide with the following chemical structure:

In one embodiment, the lipid comprises a cholesterol hemisuccinate ("CHEMS") with the following chemical structure:

By way of reference, a complete list of the chemical formulas and abbreviation(s) of the lipids disclosed herein is set forth in Table I.

In an additional embodiment, the lipid comprises a phospholipid/fatty acid disclosed herein and set forth in Table III.

In a further embodiment, the lipid comprises a Stearic acid.

In addition, the AR Prodrugs and/or liposome(s) of the disclosure may comprise one or more helper lipids which are also referred to herein as "helper lipid components." The helper lipid components are preferably selected from the group comprising phospholipids and steroids. Phospholipids are preferably di- and monoester of the phosphoric acid.

Preferred members of the phospholipids are phosphoglycerides and sphingolipids. Steroids, as used herein, are naturally occurring and synthetic compounds based on the partially hydrogenated cyclopenta[a]phenanthrene. Preferably, the steroids contain 21 to 30 C atoms. A particularly preferred steroid is cholesterol.

It is to be noted that although not wishing to be bound by any theory, due to the particular mol percentages of the helper lipid(s) contained in the lipid compositions according to the present invention, which helper lipid can be either a PEG-free helper lipid or in particular a PEG-containing helper lipid, surprising effects can be realized, more particularly if the content of any of this kind of helper lipid is contained within the concentration range specified herein.

In a further aspect of the present invention, lipid compositions which are preferably present as lipoplexes or liposomes, preferably show a neutral or overall anionic charge. The anionic lipid is preferably any neutral or anionic lipid described herein. The lipid composition comprises in a preferred embodiment any helper lipid or helper lipid combination as well as any A2aR inhibitor as described herein (for example, AR1, AR2, AR3, AR4, and AR5). In a further embodiment the composition according to the present invention containing nucleic acid(s) forms lipoplexes. In a preferred embodiment the term lipoplexes as used herein refers to a composition composed of neutral or anionic lipid, neutral helper lipid and A2aR inhibitor of the invention. For reference into the usage of helper lipids in the art, see, by way of example, U.S. Patent Application Publication 2011/0178164; OJEDA, et. al., Int. J. of Pharmaceutics (March 2016); DABKOWSKA, et. al., J. R. Soc. Interface 9, pp. 548-561 (2012); and MOCHIZUKI, et. al., Biochimica et. Biophysica Acta, 1828, pp. 412-418 (2013).

In a preferred embodiment, the helper lipids of the invention comprise the helper lipids set forth in Table II.

In one embodiment, an AR Prodrug comprises a lipid of the invention, wherein the lipid is CHEMS and wherein the drug moiety is AR1.

In one embodiment, an AR Prodrug comprises a lipid of the invention, wherein the lipid is CHEMS and wherein the drug moiety is AR2.

In one embodiment, an AR Prodrug comprises a lipid of the invention, wherein the lipid is CHEMS and wherein the drug moiety is AR3.

In one embodiment, an AR Prodrug comprises a lipid of the invention, wherein the lipid is CHEMS and wherein the drug moiety is AR4.

In one embodiment, an AR Prodrug comprises a lipid of the invention, wherein the lipid is CHEMS and wherein the drug moiety is AR5.

In one embodiment, an AR Prodrug comprises a lipid of the invention, wherein the lipid is CHEMS and wherein the drug moiety is any of AR1, AR2, AR3, AR4, or AR5, further comprising a LU and wherein the LU is a hydromethylcarbamate linker.

In one embodiment, an AR Prodrug comprises a lipid of the invention, wherein the lipid is CHEMS and wherein the drug moiety is any of AR1, AR2, AR3, AR4, or AR5, further comprising a LU and wherein the LU is a hydromethylcarbamate linker, further comprising a helper lipid component, wherein the helper lipid component comprises a helper lipid of Table II.

In one embodiment, an AR Prodrug comprises a lipid of the invention, wherein the lipid is CHEMS and wherein the drug moiety is any of AR1, AR2, AR3, AR4, or AR5 and wherein the CHEMS is monovalent.

In one embodiment, an AR Prodrug comprises a lipid of the invention, wherein the lipid is Stearic Acid and wherein the drug moiety is any of AR1, AR2, AR3, AR4, or AR5.

In one embodiment, an AR Prodrug comprises a lipid of the invention, wherein the lipid is Stearic Acid and wherein the drug moiety is any of AR1, AR2, AR3, AR4, or AR5 and wherein the Stearic Acid is monovalent.

In one embodiment, an AR Prodrug comprises a lipid of the invention, wherein the lipid is Stearic Acid and wherein the drug moiety is any of AR1, AR2, AR3, AR4, or AR5, further comprising a LU and wherein the LU is a hydromethylcarbamate linker.

In one embodiment, an AR Prodrug comprises a lipid of the invention, wherein the lipid is Stearic Acid and wherein the chemical composition is any of AR1, AR2, AR3, AR4, or AR5, further comprising a LU and wherein the LU is a hydromethylcarbamate linker, further comprising a helper lipid component, wherein the helper lipid component comprises a helper lipid of Table II.

In one embodiment, an AR Prodrug comprises a lipid of the invention, wherein the lipid is Stearic Acid and wherein the drug moiety is any of AR5.

In one embodiment, an AR Prodrug comprises a lipid of the invention, wherein the lipid is Stearic Acid and wherein the drug moiety is any of AR5 and wherein the AR Prodrug is synthesized according to Example 1 described herein.

In one embodiment, an AR Prodrug comprises a lipid of the invention, wherein the lipid is Stearic Acid and wherein the drug moiety is any of AR5 having the following chemical structure:

One of ordinary skill in the art will appreciate and be enabled to make variations and modifications to the disclosed embodiment without altering the function and purpose of the invention disclosed herein. Such variations and modifications are intended within the scope of the present disclosure.

V.) Linkage Unit(s) ("LU")

In some embodiments, the presently disclosed subject matter provides prodrugs comprising drug-lipid conjugates that include biodegradable linkages, such as esters, thioesters, and other linkers known in the art.

Exemplary embodiments of ester chemistry are set forth herein:

In some embodiments, the prodrug is a drug-lipid conjugate, whereby the drug-lipid conjugate is cleaved by an esterase.

In one embodiment, a prodrug of the invention comprises a LU via a secondary amine, amide, or aniline using the following schema:

Secondary Amine, amide, or aniline

Prodrug Structure

An exemplary synthesis is as follows:

Synthesis

Cleavage of the prodrug structure comprising a secondary amine, amide, or aniline is obtained via esterase hydrolysis of the secondary amine, amide, or aniline prodrug under the following exemplary synthesis:

-continued

Hydrolytically Unstable $$CO_2 \quad + \quad H_2CO$$

Wherein:

$R_1$—NH—$R_2$ can be any molecule with a secondary amine, amide, or aniline.

In one embodiment, the secondary amide nitrogen of the AR1, AR2, AR3, AR4, or AR5 drug moiety is conjugated to CHEMS via a hydromethylcarbamate linker.

In some embodiments, a lipid ester formation is preferred. An exemplary synthesis is as follows:

In a preferred embodiment a reverse ester lipid formation is utilized. An exemplary synthesis is as follows:

As will be appreciated by one of skill in the art, for lipid ester prodrugs, if the Drug Moiety has an OH functionality, either an aliphatic or aromatic alcohol, then a lipid ester prodrug can be readily formed by coupling the drug moiety with a lipid that has a carboxylic acid or activated carboxylic acid functionality. Conversely, if the Drug Moiety has a carboxylic acid functionality, then a reverse ester lipid prodrug can be formed by coupling the drug molecule with a lipid-alcohol.

In a preferred embodiment, the Lipid can be any lipid of the disclosure (see, Section entitled "Lipids," supra, including any lipid set forth in Table I, Table II, and/or Table III.

In a preferred embodiment, the lipid is Stearic Acid.

In a further preferred embodiment, the lipid is cholesterol.

In a further preferred embodiment, the lipid is Stearic Acid, and the Drug Moiety is AR5.

One of ordinary skill in the art will appreciate and be enabled to make variations and modifications to the disclosed embodiment without altering the function and purpose of the invention disclosed herein. Such variations and modifications are intended within the scope of the present disclosure.

VI.) Nanocarrier(s)

Generally speaking, and for the purposes of this disclosure nanocarrier(s) are within the scope of the invention. A nanocarrier is nanomaterial being used as a transport module for another substance, such as a drug. Commonly used nanocarriers include micelles, polymers, carbon-based materials, liposomes, and other substances. Because of their small size, nanocarriers can deliver drugs to otherwise inaccessible sites around the body. Nanocarriers can include polymer conjugates, polymeric nanoparticles, lipid-based carriers, dendrimers, carbon nanotubes, and gold nanoparticles. Lipid-based carriers include both liposomes and micelles. In certain embodiments the nanocarrier is a liposome, lipid nanoparticle ("LNP") or a solid-lipid nanoparticle ("SLNP").

In addition, nanocarriers are useful in the drug delivery process because they can deliver drugs to site-specific targets, allowing drugs to be delivered in certain organs or cells but not in others. Site-specificity poses a major therapeutic benefit since it prevents drugs from being delivered to the wrong places. In addition. Nanocarriers show promise for use in chemotherapy because they can help decrease the adverse, broader-scale toxicity of chemotherapy on healthy, fast-growing cells around the body. Since chemotherapy drugs can be extremely toxic to human cells, it is important that they are delivered to the tumor without being released into other parts of the body.

Generally speaking, there are four (4) methods in which nanocarriers can deliver drugs and they include passive targeting, active targeting, pH specificity, and temperature specificity.

Passive targeting refers to a nanocarrier's ability to travel down a tumor's vascular system, become trapped, and accumulate in the tumor. This accumulation is caused by the enhanced permeability and retention effect. The leaky vasculature of a tumor is the network of blood vessels that form in a tumor, which contain many small pores. These pores allow nanocarriers in, but also contain many bends that allow the nanocarriers to become trapped. As more nanocarriers become trapped, the drug accumulates at the tumor site. This accumulation causes large doses of the drug to be delivered directly to the tumor site.

Active targeting involves the incorporation of targeting modules such as ligands or antibodies on the surface of nanocarriers that are specific to certain types of cells around the body. Generally, nanocarriers have a high surface-area to volume ratio allowing for multiple ligands to be incorporated on their surfaces.

Additionally, certain nanocarriers will only release the drugs they contain in specific pH ranges. pH specificity also allows nanocarriers to deliver drugs directly to a tumor site. This is due to the fact that tumors are generally more acidic than normal human cells, with a pH around 6.8. Normal tissue has a pH of around 7.4. Thus, nanocarriers that only release drugs at certain pH ranges can therefore be used to release the drug only within acidic tumor environments. High acidic environments cause the drug to be released due to the acidic environment degrading the structure of the nanocarrier. Generally, these nanocarriers will not release drugs in neutral or basic environments, effectively targeting the acidic environments of tumors while leaving normal body cells untouched. This pH sensitivity can also be induced in micelle systems by adding copolymer chains to micelles that have been determined to act in a pH independent manor. See, W U, et. al., Biomaterials, 34(4): 1213-1222 (2012). These micelle-polymer complexes also help to prevent cancer cells from developing multi-drug resistance. The low pH environment triggers a quick release of the micelle polymers, causing a majority of the drug to be released at once, rather than gradually like other drug treatments.

Additionally, some nanocarriers have also been shown to deliver drugs more effectively at certain temperatures. Since tumor temperatures are generally higher than temperatures throughout the rest of the body, around 40° C., this temperature gradient helps act as safeguard for tumor-specific site delivery. See, REZAEI, et. al., Polymer, 53(16): 3485-3497 (2012).

As disclosed herein, lipid-based nanocarriers, such as liposomes are within the scope of this invention. Lipid-based nanoparticles (LBNPs or LNPs) such as liposomes, solid lipid nanoparticles (SLN) and nanostructured lipid carriers (NLC) can transport hydrophobic and hydrophilic molecules, display minimal or no toxicity, and increase the time of drug action by means of a prolonged half-life and a controlled release of the drug. Lipid nanoparticles can include chemical modifications to avoid the detection by the immune system (gangliosides or polyethylene glycol (PEG)) or to improve the solubility of the drug. In addition, they can be prepared in formulations sensitive to the pH in order to promote drug release in an acid environment and can also be associated with small molecules or antibodies that recognize tumor cells or their receptors (such as folic acid (FoA). Nanodrugs can also be used in combination with other therapeutic strategies to improve the response of patients. See, GARCIA-PINEL, et. al., Nanomaterials 9(639) (2019).

In various embodiments silica some drug carriers described herein comprise a porous silica (or other material) nanoparticle (e.g., a silica body having a surface and defining a plurality of pores that are suitable to receive molecules therein) coated with a lipid bilayer. The fact that the nanoparticle is referred to as a silica nanoparticle does not preclude materials other than silica from also being incorporated within the silica nanoparticle. In some embodiments, the silica nanoparticle may be substantially spherical with a plurality of pore openings through the surface providing access to the pores. However, in various embodiments the silica nanoparticle can have shapes other than substantially spherical shapes. Thus, for example, in certain embodiments the silica nanoparticle can be substantially ovoid, rod-shaped, a substantially regular polygon, an irregular polygon, and the like.

Generally, the silica nanoparticle comprises a silica body that defines an outer surface between the pore openings, as well as side walls within the pores. The pores can extend through the silica body to another pore opening, or a pore can extend only partially through the silica body such that that it has a bottom surface of defined by the silica body.

In some embodiments, the silica body is mesoporous. In other embodiments, the silica body is microporous. As used herein, "mesoporous" means having pores with a diameter between about 2 nm and about 50 nm, while "microporous" means having pores with a diameter smaller than about 2 nm. In general, the pores may be of any size, but in typical embodiments are large enough to contain one or more therapeutic compounds therein. In such embodiments, the pores allow small molecules, for example, therapeutic compounds such as anticancer compounds to adhere or bind to the inside surface of the pores, and to be released from the silica body when used for therapeutic purposes. In some embodiments, the pores are substantially cylindrical.

In certain embodiments the nanoparticles comprise pores having pore diameters between about 1 nm and about 10 nm in diameter or between about 2 nm and about 8 nm. In certain embodiments the nanoparticles comprise pores having pore diameters between about 1 nm and about 6 nm, or between about 2 nm and about 5 nm. Other embodiments include particles having pore diameters less than 2.5 nm.

In other embodiments, the pore diameters are between 1.5 and 2.5 nm. Silica nanoparticles having other pore sizes may be prepared, for example, by using different surfactants or swelling agents during the preparation of the silica nanoparticles. In various embodiments the nanoparticles can include particles as large (e.g., average, or median diameter (or another characteristic dimension) as about 1000 nm. However, in various embodiments the nanoparticles are typically less than 500 nm or less than about 300 nm as, in general, particles larger than 300 nm may be less effective in entering living cells or blood vessel fenestrations. In certain embodiments the nanoparticles range in size from about 40 nm, or from about 50 nm, or from about 60 nm up to about 100 nm, or up to about 90 nm, or up to about 80 nm, or up to about 70 nm. In certain embodiments the nanoparticles range in size from about 60 nm to about 70 nm. Some embodiments include nanoparticles having an average maximum dimension between about 50 nm and about 1000 nm. Other embodiments include nanoparticles having an average maximum dimension between about 50 nm and about 500 nm. Other embodiments include nanoparticles having an average maximum dimension between about 50 nm and about 200 nm.

In some embodiments, the average maximum dimension is greater than about 20 nm, greater than about 30 nm, greater than about 40 nm, or greater than about 50 nm. Other embodiments include nanoparticles having an average maximum dimension less than about 500 nm, less than about 300 nm, less than about 200 nm, less than about 100 nm or less than about 75 nm. As used herein, the size of the nanoparticle refers to the average or median size of the primary particles, as measured by transmission electron microscopy (TEM) or similar visualization techniques known in the art. Further examples of mesoporous silica nanoparticles include, but are not limited to, MCM-41, MCM-48, and SBA-15. See, KATIYARE, et. al., J. Chromotog. 1122(1-2): 13-20 (2006).

Methods of making porous silica nanoparticles are well known to those of skill in the art. In certain embodiments mesoporous silica nanoparticle are synthesized by reacting tetraethyl orthosilicate (TEOS) with a template made of micellar rods. The result is a collection of nano-sized spheres or rods that are filled with a regular arrangement of pores. The template can then be removed by washing with a solvent adjusted to the proper pH (See, e.g., TREWYN et al. (2007) Chem. Eng. J. 137(1): 23-29).

In certain embodiments mesoporous particles can also be synthesized using a simple sol-gel method (See, e.g., NANDIYANTO, et al. (2009) Microporous and Mesoporous Mat. 120(3): 447-453). In certain embodiments tetraethyl orthosilicate can also be used with an additional polymer monomer as a template. In certain embodiments 3-mercaptopropyl) trimethoxysilane (MPTMS) is used instead of TEOS.

In certain embodiments the mesoporous silica nanoparticles are cores are synthesized by a modification of the sol/gel procedure described by MENG et. al. (2015) ACS Nemo, 9(4): 3540-3557.

While the methods described herein have been demonstrated with respect to porous silica nanoparticles (e.g., mesoporous silica), it will be recognized by those skilled in the art that similar methods can be used with other porous nanoparticles. Numerous other mesoporous materials that can be used in drug delivery nanoparticles are known to those of skill in the art. For example, in certain embodiments mesoporous carbon nanoparticles could be utilized.

Mesoporous carbon nanoparticles are well known to those of skill in the art (See, e.g., HUANG et. al. (2016) Carbon, 101:135-142; ZHU et. al. (2014) Asian J. Pharm. Sci., 9(2): 82-91; and the like).

Similarly, in certain embodiments, mesoporous polymeric particles can be utilized. The syntheses of highly ordered mesoporous polymers and carbon frameworks from organic-organic assembly of triblock copolymers with soluble, low-molecular-weight phenolic resin precursors (resols) by an evaporation induced self-assembly strategy have been reported by MENG, et. al. (2006) Chem. Mat. 6(18): 4447-4464.

The nanoparticles described herein are illustrative and non-limiting. Using the teachings provided herein numerous other lipid bilayer coated nanoparticles will be available to one of skill in the art.

In one embodiment, the invention teaches nanocarriers which comprise AR Prodrugs.

In one embodiment, the invention teaches a nanocarrier comprising a liposome, wherein the lipid comprises CHEMS.

In one embodiment, the invention teaches a nanocarrier comprising a liposome, wherein the lipid comprises Stearic Acid.

In one embodiment, the invention teaches a nanocarrier comprising a liposome, wherein the lipid comprises CHEMS and whereby the liposome further comprises an AR Prodrug.

In one embodiment, the invention teaches a nanocarrier comprising a liposome, wherein the lipid comprises CHEMS and whereby the liposome further comprises AR1.

In one embodiment, the invention teaches a nanocarrier comprising a liposome, wherein the lipid comprises CHEMS and whereby the liposome further comprises AR2.

In one embodiment, the invention teaches a nanocarrier comprising a liposome, wherein the lipid comprises CHEMS and whereby the liposome further comprises AR3.

In one embodiment, the invention teaches a nanocarrier comprising a liposome, wherein the lipid comprises CHEMS and whereby the liposome further comprises AR4.

In one embodiment, the invention teaches a nanocarrier comprising a liposome, wherein the lipid comprises CHEMS and whereby the liposome further comprises AR5.

In one embodiment, the invention teaches a nanocarrier comprising a liposome, wherein the lipid comprises Stearic Acid and whereby the liposome further comprises an A2aR inhibitor.

In one embodiment, the invention teaches a nanocarrier comprising a liposome, wherein the lipid comprises Stearic Acid and whereby the liposome further comprises AR1.

In one embodiment, the invention teaches a nanocarrier comprising a liposome, wherein the lipid comprises Stearic Acid and whereby the liposome further comprises AR2.

In one embodiment, the invention teaches a nanocarrier comprising a liposome, wherein the lipid comprises Stearic Acid and whereby the liposome further comprises AR3.

In one embodiment, the invention teaches a nanocarrier comprising a liposome, wherein the lipid comprises Stearic Acid and whereby the liposome further comprises AR4.

In one embodiment, the invention teaches a nanocarrier comprising a liposome, wherein the lipid comprises Stearic Acid and whereby the liposome further comprises AR5.

In one embodiment, the invention teaches a nanocarrier comprising a liposome, wherein the lipid comprises Stearic Acid and whereby the liposome further comprises AR5 (denoted LNP-AR5).

In a further embodiment, the invention teaches a nano-carrier comprising a liposome, wherein the lipid comprises Stearic Acid and whereby the liposome further comprises AR5 and whereby the liposome is co-formulated with a toll-like receptor agonist, wherein the toll-like receptor agonist comprises a toll-like receptor agonist denoted TR3, TR5, and TR6 (denoted LNP-AR5-TR3, LNP-AR5-TR5, and LNP-AR5-TR6, respectively).

In a further embodiment, the invention teaches a nano-carrier comprising a liposome, wherein the lipid comprises Stearic Acid and whereby the liposome further comprises AR5 and whereby the liposome is co-formulated with a TGFβ inhibitor, wherein the TGFβ inhibitor comprises a TGFβ inhibitor denoted TB4 (denoted LNP-AR5-TB4).

In a further embodiment, the invention teaches a nano-carrier comprising a liposome, wherein the lipid comprises Stearic Acid and whereby the liposome further comprises AR5 and whereby the liposome is co-formulated with a PD-1 antagonist, wherein the PD-1 antagonist comprises a PD-1 antagonist denoted PD3 (denoted LNP-AR5-PD3).

In a further embodiment, the invention teaches a nano-carrier comprising a liposome, wherein the lipid comprises Stearic Acid and whereby the liposome further comprises AR5 and whereby the liposome is co-formulated with an IDO inhibitor, wherein the IDO inhibitor comprises an IDO inhibitor denoted ID3 (denoted LNP-AR5-ID3).

In a preferred embodiment, the lipid particle comprises a solid-lipid nanoparticle (SLNP) comprising a liposome which comprises an AR Prodrug.

In a preferred embodiment, the lipid particle comprises a solid-lipid nanoparticle (SLNP) comprising a liposome which comprises an AR Prodrug, wherein the AR Prodrug comprises AR1.

In a preferred embodiment, the lipid particle comprises a solid-lipid nanoparticle (SLNP) comprising a liposome which comprises an AR Prodrug, wherein the AR Prodrug comprises AR2.

In a preferred embodiment, the lipid particle comprises a solid-lipid nanoparticle (SLNP) comprising a liposome which comprises an AR Prodrug, wherein the AR Prodrug comprises AR3.

In a preferred embodiment, the lipid particle comprises a solid-lipid nanoparticle (SLNP) comprising a liposome which comprises an AR Prodrug, wherein the AR Prodrug comprises AR4.

In a preferred embodiment, the lipid particle comprises a solid-lipid nanoparticle (SLNP) comprising a liposome which comprises an AR Prodrug, wherein the AR Prodrug comprises AR5.

In one embodiment, the invention teaches a nanocarrier comprising a solid-lipid nanoparticle ("SLNP"), wherein the solid-lipid nanoparticle comprises Stearic Acid and whereby the solid-lipid nanoparticle further comprises AR5 (denoted SLNP-AR5).

In a further embodiment, the invention teaches a nano-carrier comprising a SLNP, wherein the lipid comprises Stearic Acid and whereby the SLNP further comprises AR5 and whereby the SLNP is co-formulated with a toll-like receptor agonist, wherein the toll-like receptor agonist comprises a toll-like receptor agonist denoted TR3, TR5, and TR6 (denoted SLNP-AR5-TR3, SLNP-AR5-TR5, and SLNP-AR5-TR6, respectively).

In a further embodiment, the invention teaches a nano-carrier comprising a SLNP, wherein the lipid comprises Stearic Acid and whereby the SLNP further comprises AR5 and whereby the SLNP is co-formulated with a TGFβ inhibitor, wherein the TGFβ inhibitor comprises a TGFβ inhibitor denoted TB4 (denoted SLNP-AR5-TB4).

In a further embodiment, the invention teaches a nano-carrier comprising a SLNP, wherein the lipid comprises Stearic Acid and whereby the SLNP further comprises AR5 and whereby the SLNP is co-formulated with a PD-1 antagonist, wherein the PD-1 antagonist comprises a PD-1 antagonist denoted PD3 (denoted SLNP-AR5-PD3).

In a further embodiment, the invention teaches a nanocarrier comprising a SLNP, wherein the lipid comprises Stearic Acid and whereby the SLNP further comprises AR5 and whereby the SLNP is co-formulated with an IDO inhibitor, wherein the IDO inhibitor comprises an IDO inhibitor denoted ID3 (denoted SLNP-AR5-ID3).

In a further preferred embodiment, the solid-lipid nanoparticle of the invention comprises a composition having the following ratio(s):

| Constituent of the SLNP | Amount (% w/w) |
| --- | --- |
| Lipid 1 (lipid-prodrug) | 5-80 |
| Lipid 2 (lipid-prodrug) | 0-40 |
| Helper lipids | 0-80 |
| DSPE-PEG2000 | 0-10 |
| Stabilizer(s) | 0.5-20 |

In a further preferred embodiment, the solid-lipid nanoparticle of the invention comprises a composition having the following ratio(s):

| Constituent of the SLNP | Amount (% w/w) |
| --- | --- |
| Lipid 1 (lipid-prodrug) | 5-80 |
| Lipid 2 (lipid-prodrug) | 0-40 |
| Lipid 3 (Lipid-prodrug) | 0-30 |
| Helper lipids | 0-80 |
| DSPE-PEG2000 | 0-10 |
| Stabilizer(s) | 0.5-20 |

Whereby Lipid 1 comprises a AR5-Prodrug, wherein the lipid moiety comprises Stearic Acid and whereby the helper lipids are the helper lipids set forth in Table II and whereby the stabilizers are selected from the group consisting of polyvinyl alcohol (e.g., Moliwol 488), poloxamers (e.g., Pluronic F127), Tween 80, PEG400, and Kolliphor RH 40 and whereby Lipid 2 and Lipid 3 (lipid prodrug) comprises a lipid prodrug of the disclosure or a lipid prodrug selected from the group consisting of ID3, PD3, TR3, TB4 inhibitors (for examples ID3-STEA, ID3-CHEM, PD3-STEA, TR3-STEA, TB4-STEA, etc.), MPLA, and Telratolimod.

One of ordinary skill in the art will appreciate and be enabled to make variations and modifications to the disclosed embodiment without altering the function and purpose of the invention disclosed herein. Such variations and modifications are intended within the scope of the present disclosure.

The scope of the disclosure teaches three (3) possible treatment modalities using the formulated prodrugs of the invention. See, PCT Patent Publication No. WO2018/213631.

The first treatment modality involves combination of an AR Prodrug in combination with another therapeutic (e.g., another formulated prodrug which inhibits A2aR and other family members, a chemotherapy agent (such as an ICD-inducing chemotherapy), etc.) into a single liposome that allows systemic (or local) biodistribution and drug delivery to tumor sites. The dual-delivery approach achieves synergistic enhancement of adaptive and innate immunity, leading to a significant improvement in animal survival. In certain embodiments the nanocarrier comprises a vesicle (i.e., a lipid bilayer enclosing a fluid).

A second treatment modality involves local delivery to a tumor or peri-tumoral region, of an agent that inhibits A2aR and other family members in combination with a lipid (e.g., a liposome) that comprises an inhibitor of A2aR signaling.

A third treatment modality involves vaccination utilizing dying cancer cells (e.g., KPC cells) in which inhibition of A2aR is induced ex vivo. It is discovered that such vaccination can generate a systemic immune response that can interfere with tumor growth at a remote site as well as allowing adoptive transfer to non-immune animals. One of skill in the art will appreciate and be enabled to perform methods the treatment modalities provided herein.

VII.) Liposomes

In one aspect, the presently disclosed subject matter is based on an approach for providing an AR Prodrug of the disclosure (See, section entitled Prodrugs) suitable for incorporation into a nanocarrier comprising lipid coating layers to provide enhanced delivery of the corresponding prodrugs and for providing combination therapies including the prodrugs. The advantages for using prodrugs of the invention include the facilitation of controlled formulation into an LNP of the disclosure (e.g., a liposome). This allows the prodrug to be maintained in an inactive form during systemic circulation, which allows the liposome to release the active agent after engulfment by a cell, for example within a tumor.

In certain embodiments one or more AR Prodrugs (e.g., any one or more of the AR Prodrugs inhibitors taught in Formula I, and/or an AR1-Prodrug, AR2, Prodrug, AR3-Prodrug, AR4-Prodrug, or AR5-Prodrug) (See, section entitled prodrugs) are formulated a lipid moiety that forms a vesicle (e.g., a liposome) structure in aqueous solution or that can form a component of a lipid bilayer comprising a liposome. The liposomes can be used directly, provided as components in a combined formulation (e.g., in combination with another drug moiety or therapeutic modality as disclosed herein).

In certain embodiments, the liposome that is formulated with the AR Prodrug comprises a lipid, PHGP, vitamin E, cholesterol, and/or a fatty acid.

In one embodiment, the liposome comprises cholesterol.

In one embodiment, the liposome comprises DSPC.

In one embodiment, the liposome comprises HSPC.

In one embodiment, the liposome comprises DSPE-PEG2000.

In one embodiment, the liposome comprises DPPG.

In one embodiment, the liposome comprises DMPG.

In one embodiment, the liposome Lyso PC.

In one embodiment, the liposome (A9-Cis) PG.

In one embodiment, the liposome comprises Soy Lyso PC.

In one embodiment, the liposome comprises PG.

In one embodiment, the liposome comprises PA-PEG3-mannose.

In one embodiment, the liposome comprises C16 PEG2000 Ceramide.

In one embodiment, the liposome comprises MPLA.

In one embodiment, the liposome comprises CHEMS.

In one embodiment, the liposome comprises Stearic Acid.

In one embodiment, the liposome comprises a phospholipid set forth in Table III.

In one embodiment, the liposome comprises AR5 and further comprises CHEMS and further comprises a LU wherein said LU is a hydromethylcarbamate linker.

In one embodiment, the liposome comprises AR5 and further comprises Stearic Acid and further comprises a LU wherein said LU is a hydromethylcarbamate linker.

In one embodiment, the liposome comprises AR5 and further comprises CHEMS and further comprises a LU wherein said LU is a hydromethylcarbamate linker and further comprises a helper lipid set forth in Table II.

In one embodiment, the liposome comprises AR5 and further comprises a Stearic Acid and further comprises a LU wherein said LU is a hydromethylcarbamate linker and further comprises a helper lipid set forth in Table II.

In one embodiment, the liposome of the disclosure comprises an AR Prodrug co-formulated with one or more additional immune modulating agents, whereby the immune modulating agents includes, but is not limited to, immunogenic-cell death inducing chemotherapeutics, toll-like receptor agonists, sting agonists, IDO inhibitors, CTLA4 inhibitors, PD-1 inhibitors, and/or prodrugs thereof.

In a preferred embodiment, the liposome comprises an AR Prodrug co-formulated with an ICD-inducing Chemotherapeutic.

In a preferred embodiment, the liposome comprises an AR Prodrug co-formulated with an ICD-inducing Chemotherapeutic selected from the list: doxorubicin (DOX), mitoxantrone (MTO), Oxaliplatin (OXA), Cyclophosphamide (CP), Bortezomib, Carfilzomib, or Paclitaxel.

In a preferred embodiment, the liposome comprises an AR Prodrug co-formulated with a Toll-Like Receptor TLR agonist/Prodrug.

In a preferred embodiment, the liposome comprises an AR Prodrug co-formulated with Toll-Like Receptor (TLR) agonist/Prodrug selected from the list: TR3, Resiquimod (R848), Gardiquimod, 852A, DSR 6434, Telratolimod, CU-T12-9, monophosphoryl Lipid A (MPLA), 3D (6-acyl)-PHAD®, SMU127, Pam3CSK4, or 3D-PHAD® or prodrugs thereof In a preferred embodiment, the liposome comprises an AR Prodrug co-formulated with a PD-1 inhibitor/Prodrug.

In a preferred embodiment, the liposome comprises an AR Prodrug co-formulated with a PD-1 inhibitor/Prodrug, selected from the list: PD3, AUNP12, CA-170, or BMS-986189 or prodrugs thereof.

In a preferred embodiment, the liposome comprises an AR Prodrug co-formulated with an IDO-1 inhibitor/Prodrug.

In a preferred embodiment, the liposome comprises an AR Prodrug co-formulated with an IDO-1 inhibitor/Prodrug, selected from the list: ID3, epacadostat, L-1-methyl tryptophan (Indoximod), D-1-methyl tryptophan, Linrodostat mesylate (BMS 986205), MK-7162, LY-3381916, KHK-2455, HTI-1090, DN-1406131, or BGB-5777.

In a preferred embodiment, the liposome comprises an AR Prodrug co-formulated with doxorubicin (DOX).

In a preferred embodiment, the liposome comprises an AR Prodrug co-formulated with mitoxantrone (MTO).

In a preferred embodiment, the liposome comprises an AR Prodrug co-formulated with doxorubicin (DOX) and an PD-1 prodrug.

In a preferred embodiment, the liposome comprises an AR Prodrug co-formulated with mitoxantrone (MTO) and a PD-1 prodrug.

In a preferred embodiment, the liposome comprises an AR Prodrug co-formulated with doxorubicin (DOX) and an IDO-1 prodrug.

In a preferred embodiment, the liposome comprises an AR Prodrug co-formulated with mitoxantrone (MTO) and an IDO-1 prodrug.

In a preferred embodiment, the liposome comprises an AR Prodrug co-formulated with doxorubicin (DOX) and a TLR agonist/prodrug.

In a preferred embodiment, the liposome comprises an AR Prodrug co-formulated with mitoxantrone (MTO) and a TLR agonist/prodrug.

In a preferred embodiment, the liposome comprises an AR Prodrug co-formulated with doxorubicin (DOX) and a PD-1 prodrug and a TLR agonist/prodrug.

In a preferred embodiment, the liposome comprises an AR Prodrug co-formulated with mitoxantrone (MTO) and a PD-1 prodrug and a TLR agonist/prodrug.

In a preferred embodiment, the liposome comprises an AR Prodrug co-formulated with a TLR agonist/prodrug.

In a preferred embodiment, the liposome comprises an AR Prodrug co-formulated with a TGFβ inhibitor/prodrug.

In a preferred embodiment, the liposome comprises an AR Prodrug co-formulated with an IDO antagonist/prodrug.

In a preferred embodiment, the liposome comprises an AR Prodrug co-formulated with a CTLA4 agonist/prodrug.

In a preferred embodiment, the liposome comprises an AR Prodrug co-formulated with a TLR agonist/prodrug and a PD-1 prodrug.

In a preferred embodiment, the liposome comprises an AR Prodrug co-formulated with a TLR agonist/prodrug and an IDO-1 prodrug.

In a preferred embodiment, the liposome comprises AR5-Prodrug co-formulated with doxorubicin (DOX).

In a preferred embodiment, the liposome comprises AR5-Prodrug co-formulated with mitoxantrone (MTO).

In a preferred embodiment, the liposome comprises AR5-Prodrug co-formulated with doxorubicin (DOX) and/or and IDO prodrug and/or a TLR agonist/prodrug.

In a preferred embodiment, the liposome comprises AR5-Prodrug co-formulated with mitoxantrone (MTO) and/or and IDO prodrug and/or a TLR agonist/prodrug.

One of skill in the art will appreciate and understand that solubility is one of most common problems faced by the artisan in the drug development process. Chemical conjugation of a drug/anti-cancer agents via lipid molecules (i.e., lipid-based prodrugs) provides a platform to solve the problem of formulating the drugs in an aqueous suspension. The major advantages of delivering drug(s) with lipid conjugation (lipid-based prodrugs) lies on its ability to improve pharmacokinetics/half-life and targeted delivery.

With suitable selection of lipid molecules, lipid-based prodrug(s) can be integrated/formulated in a liposomal formulation using techniques known in the art, which has many more advantages over conventional drug delivery system. (KOHLI, et. al., J. Control Release, 0: pp 274-287 (Sep. 28, 2014); and GARCIA-PINEL, et. al., Nanomaterials 9:638 (2019). The advantage of combining lipid-prodrug with liposomes is twofold: (i) liposomes containing lipid-prodrug not only increase the solubility of the drug/prodrug itself, but (ii) also have the ability to encapsulate multiple drugs (both hydrophilic and lipophilic) (see, section entitled nanocarriers).

For the purposes of this disclosure, the major advantage of liposome formulations are as follows:

i) biocompatibility/biodegradability and no general toxicity of the liposome's formulations;

ii) flexibility and manipulation of size and surface charge depending on the required purpose. Liposome formulation(s), for the purposes of this disclosure, can have a size range of 40-150 nm in diameter and a surface charge in the range of −40 to +40 mV; and iii) Liposomes of the invention have either a single or multiple lipid-prodrugs as the constituent lipid portion of the liposome(s). Additionally, multiple drugs (e.g., that work in different mechanism of action) and with different solubility profile (hydrophilic or lipophilic) can be formulated (either in the lipid bilayers or in the hydrophilic core) in these liposomes.

As one of ordinary skill in the art will appreciate, all methods of making liposomes involve four (4) basic stages:
(i) Drying down lipids from organic solvent;
(ii) Dispersing the lipid in aqueous solution;
(iii) Purifying the resultant liposome; and
(iv) Analyzing the final product.

See, AKBARZADEH, et. al., Nanoscale Research Letters, 8:102 (2013).

Another aspect of the invention discloses liposomal encapsulation technology (LET) which is a delivery technique used to transmit drugs. LET is a method of generating sub-microscopic foams called liposomes, which encapsulate numerous materials. These 'liposomes' form a barrier around their contents, which is resistant to enzymes in the mouth and stomach, alkaline solutions, digestive juices, bile salts, and intestinal flora that are generated in the human body, as well as free radicals. The contents of the liposomes are, therefore, protected from oxidation and degradation. This protective phospholipid shield or barrier remains undamaged until the contents of the liposome are delivered to the exact target gland, organ, or system where the contents will be utilized (See, section entitled nanocarriers).

In one embodiment, liposome(s) of the disclosure are synthesized using a plurality of different ratios of AR Prodrugs, lipids, and/or lipid-prodrugs. As disclosed herein, the AR Prodrugs may comprise helper lipids as disclosed herein (See, for example Table II).

In one embodiment, liposome(s) of the disclosure are synthesized using a plurality of different ratios of AR Prodrugs, lipids, and/or lipid-prodrugs. As disclosed herein, the AR Prodrugs may further comprise DSPE-PEGs.

In a preferred embodiment, the liposomes of the invention comprise a composition having the following ratio(s):

| Constituent of the Liposome | Amount (% w/w) |
| --- | --- |
| Lipid 1 (lipid-prodrug) | 10-40 |
| Lipid 2 (lipid-prodrug) | 0-40 |
| Helper lipids | 50-80 |
| DSPE-PEG 2000 | 2-5 |

In a further preferred embodiment, the liposomes of the invention comprise a composition having the following ratio(s):

| Constituent of the Liposome | Amount (% w/w) |
| --- | --- |
| Lipid 1 (lipid-prodrug) | 10-40 |
| Helper lipids | 50-80 |
| DSPEG-PEG 2000 | 2-5 |

In a further preferred embodiment, the liposomes of the invention comprise a composition having the following ratio(s):

| Constituent of the Liposome | Amount (% w/w) |
| --- | --- |
| Lipid 1 (lipid-prodrug) | 10-40 |
| Helper lipids | 50-80 |
| DSPEG-PEG 2000 | 2-5 |

Whereby Lipid 1 comprises a AR5-Prodrug, wherein the lipid moiety comprises CHEMS.

In a further preferred embodiment, the liposomes of the invention comprise a composition having the following ratio(s):

| Constituent of the Liposome | Amount (% w/w) |
| --- | --- |
| Lipid 1 (lipid-prodrug) | 10-40 |
| Helper lipids | 50-80 |
| DSPEG-PEG 2000 | 2-5 |

Whereby Lipid 1 comprises a AR5-Prodrug, wherein the lipid moiety comprises Stearic Acid.

In a further preferred embodiment, the liposomes of the invention comprise a composition having the following ratio(s):

| Constituent of the Liposome | Amount (% w/w) |
| --- | --- |
| Lipid 1 (lipid-prodrug) | 10-40 |
| Lipid 2 (lipid-prodrug) | 0-40 |
| Lipid 3 (lipid-prodrug) | 0-30 |
| Helper lipids | 50-80 |
| DSPEG-PEG 2000 | 2-5 |

Whereby Lipid 1 comprises a AR5-Prodrug, wherein the lipid moiety comprises Stearic Acid and whereby Lipid 2 and Lipid 3 (lipid prodrug) comprises a lipid prodrug of the disclosure or a lipid prodrug selected from the group consisting of ID3, PD3, TR3, TB4 inhibitors (for examples ID3-STEA, ID3-CHEM, PD3-STEA, TR3-STEA, TB4-STEA, etc.), MPLA, and Telratolimod.

One of ordinary skill in the art will appreciate and be enabled to make variations and modifications to the disclosed embodiment without altering the function and purpose of the invention disclosed herein. Such variations and modifications are intended within the scope of the present disclosure.

VIII.) Pharmaceutical Formulation

As used herein, the term "drug" is synonymous with "pharmaceutical." In certain embodiments, the liposome of the disclosure is fabricated to an encapsulated dosage form to and given to a patient for the treatment of disease.

Generally speaking, pharmaceutical formulation is the process in which different chemical substances are combined to a pure drug substance to produce a final drug product. Formulation studies involve developing a preparation of the drug which is both stable and acceptable to the patient. For orally taken drugs, this usually involves incorporating the drug into a tablet or a capsule. It is important to appreciate that a dosage form contains a variety of other substances apart from the drug itself, and studies have to be carried out to ensure that the drug is compatible with these other substances.

An excipient is an inactive substance used as a carrier for the active ingredients of a drug product, in this case a liposome comprising an AR Prodrug. In addition, excipients can be used to aid the process by which a drug product is manufactured. The active substance is then dissolved or mixed with an excipient. Excipients are also sometimes used to bulk up formulations with very potent active ingredients, to allow for convenient and accurate dosage. Once the active ingredient has been purified, it cannot stay in purified form for an extended period of time. In many cases it will denature, fall out of solution, or stick to the sides of the container.

To stabilize the active ingredient, excipients are added to ensure that the active ingredient stays active and is stable for a long enough period of time that the shelf-life of the product makes it competitive with other products and safe for the end-user. Examples of excipients include but are not limited to, anti-adherents, binders, coatings, disintegrants, fillers, diluents, flavors, colors, lubricants, and preservatives. The final formulation comprises and active ingredient and excipients which are then enclosed in the pharmaceutical dosage form.

Pre-formulation involves the characterization of a drug's physical, chemical, and mechanical properties in order to choose what other ingredients should be used in the preparation. Formulation studies then consider such factors as stability, particle size, polymorphism, pH, and solubility, as all of these can influence bioavailability and hence the activity of a drug. The drug must be combined with inactive additives by a method which ensures that the quantity of drug present is consistent in each dosage unit (e.g., each vial). The dosage should have a uniform appearance.

It is unlikely that these studies will be complete by the time clinical trials commence. This means that simple preparations are developed initially for use in phase I clinical trials. These typically consist of vials, hand-filled capsules containing a small amount of the drug, and a diluent. Proof of the long-term stability of these formulations is not required, as they will be used (tested) in a matter of days. However, long-term stability is critical in supply chain management since the time the final formulation is packaged until it reaches the patient can be several months or years. Consideration has to be given to what is called the drug load (i.e., the ratio of the active drug to the total contents of the dose). A low drug load may cause homogeneity problems. A high drug load may pose flow problems or require large capsules if the compound has a low bulk density. By the time phase III clinical trials are reached, the formulation of the drug should have been developed to be close to the preparation that will ultimately be used in the market.

A knowledge of stability is essential by this stage, and conditions must have been developed to ensure that the drug is stable in the preparation. If the drug proves unstable, it will invalidate the results from clinical trials since it would be impossible to know what the administered dose actually was. Stability studies are carried out to test whether temperature, humidity, oxidation, or photolysis (ultraviolet light or visible light) have any effect, and the preparation is analyzed to see if any degradation products have been formed. It is also important to check whether there are any unwanted interactions between the preparation and the container. If a plastic container is used, tests are carried out to see whether any of the ingredients become adsorbed on to the plastic, and whether any plasticizers, lubricants, pigments, or stabilizers leach out of the plastic into the preparation. Even the adhesives for the container label need to be tested, to ensure they do not leach through the plastic container into the preparation. The way a drug is formulated can avoid some of the problems associated with oral administration. Drugs are normally taken orally as tablets or capsules. The drug (active substance) itself needs to be soluble in aqueous solution at a controlled rate. Such factors as particle size and crystal form can significantly affect dissolution. Fast dissolution is not always ideal. For example, slow dissolution rates can prolong the duration of action or avoid initial high plasma levels.

In some embodiments, the nanocarrier (e.g., a liposome comprising an AR prodrug) and/or the liposome comprising an AR prodrug and co-formulated with an immune modulating agent are administered alone or in a mixture with a physiologically acceptable carrier (such as physiological saline or phosphate buffer) selected in accordance with the route of administration and standard pharmaceutical practice. For example, when used as an injectable, the nanocarriers can be formulated as a sterile suspension, dispersion, or emulsion with a pharmaceutically acceptable carrier. In certain embodiments normal saline can be employed as the pharmaceutically acceptable carrier. Other suitable carriers include, e.g., water, buffered water, 0.4% saline, 0.3% glycine, 5% glucose and the like, including glycoproteins for enhanced stability, such as albumin, lipoprotein, globulin, etc. In compositions comprising saline or other salt-containing carriers, the carrier is preferably added following nanocarrier formation. Thus, after the nanocarrier is formed and loaded with suitable drug(s), the nanocarrier can be diluted into pharmaceutically acceptable carriers such as normal saline. Similarly, the AR prodrug liposomes can be introduced into carriers that facilitate suspension of the nanomaterials (e.g., emulsions, dilutions, etc.).

The pharmaceutical compositions may be sterilized by conventional, well-known sterilization techniques. The resulting aqueous solutions, suspensions, dispersions, emulsions, etc., may be packaged for use or filtered under aseptic conditions. In certain embodiments the drug delivery nanocarriers (e.g., LNP or SLNP-coated nanoparticles) are lyophilized, the lyophilized preparation being combined with a sterile aqueous solution prior to administration. The compositions may also contain pharmaceutically acceptable auxiliary substances as required to approximate physiological conditions, such as pH-adjusting and buffering agents, tonicity adjusting agents and the like, for example, sodium acetate, sodium lactate, sodium chloride, potassium chloride, calcium chloride, etc.

Additionally, in certain embodiments, the pharmaceutical formulation may include lipid-protective agents that protect lipids against free-radical and lipid-peroxidative damage on storage. Lipophilic free-radical quenchers, such as alpha-tocopherol and water-soluble iron-specific chelators, such as ferrioxamine, are suitable and contemplated herein. The concentration of nanocarrier (e.g., SLNP or liposome comprising AR prodrugs) in the pharmaceutical formulations can vary widely, e.g., from less than approximately 0.05%, usually at least approximately 2 to 5% to as much as 10 to 50%, or to 40%, or to 30% by weight and are selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, nanocarriers composed of irritating lipids may be diluted to low concentrations to lessen inflammation at the site of administration. The amount of nanocarriers administered will depend upon the particular drug used, the disease state being treated and the judgment of the clinician but will generally be between approximately 0.01 and approximately 50 mg per kilogram of body weight, preferably between approximately 0.1 and approximately 5 mg per kg of body weight.

One of skill in the art will appreciate that exact dosages will vary depending upon such factors as the particular AR prodrugs and any co-formulated immune modulating agents and the desirable medical effect, as well as patient factors such as age, sex, general condition, and the like. Those of skill in the art can readily take these factors into account and use them to establish effective therapeutic concentrations without resort to undue experimentation.

For administration to humans (or to non-human mammals) in the curative, remissive, retardive, or prophylactic treatment of diseases described herein the prescribing physician will ultimately determine the appropriate dosage of the drug for a given human (or non-human) subject, and this can be expected to vary according to the age, weight, and response of the individual as well as the nature and severity of the patient's disease. In certain embodiments the dosage of the drug provided by the nanocarrier(s) can be approximately equal to that employed for the free drug. However as noted above, the nanocarriers described herein can significantly reduce the toxicity of the drug(s) administered thereby and significantly increase a therapeutic window. Accordingly, in some cases dosages in excess of those prescribed for the free drug(s) will be utilized.

One of ordinary skill in the art will appreciate and be enabled to make variations and modifications to the disclosed embodiment without altering the function and purpose of the invention disclosed herein. Such variations and modifications are intended within the scope of the present disclosure.

IX.) Combination Therapy

As the skilled artisan will appreciate and understand, cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

Thus, the liposomes or SLNPs comprising AR Prodrugs of the present disclosure can be used in combination with one or more other enzyme/protein/receptor inhibitors or one or more therapies for the treatment of diseases, such as cancer or infections. Examples of diseases and indications treatable with combination therapies include those set forth in the present disclosure. Examples of cancers include, but are not limited to, solid tumors and liquid tumors, such as blood cancers. Examples of infections include viral infections, bacterial infections, fungus infections or parasite infections.

For example, the liposomes or SLNPs comprising AR Prodrugs of the present disclosure can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, PI3K (alpha, beta, gamma, delta), CSFIR, KIT, FLK-II, KDR/FLK-1, FLK-4, flt-1, FGFR1, FGFR2, FGFR3, FGFR4, c-Met, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf.

In further embodiments, the liposomes or SLNPs comprising AR Prodrugs of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib, or INCB39110), an IDO inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer), an adenosine receptor antagonist (e.g., A2a/A2b receptor antagonist), an HPK1 inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), a poly ADP ribose polymerase (PARP) inhibitor such as rucaparib, laparib, niraparib, veliparib, or talazoparib, an arginase inhibitor (INCB01158), TGFβ inhibitor, a PD-1 inhibitor, a PD-1/L-1 inhibitor, a PD-1/L-2 inhibitor, a CTLA-4 antagonist, and an adenosine receptor antagonist or combinations thereof.

Additionally, the liposomes or SLNPs comprising AR Prodrugs of the present disclosure can further be used in combination with other methods of treating cancers, for example by chemotherapy, irradiation therapy, tumor-targeted therapy, adjuvant therapy, immunotherapy, or surgery.

Examples of immunotherapy include cytokine treatment (e.g., interferons, GM-CSF, G-CSF, IL-2), CRS-207 immunotherapy, cancer vaccine, monoclonal antibody, adoptive T cell transfer, Toll-like receptor agonists, STING agonists, oncolytic virotherapy and immunomodulating small molecules, including thalidomide or JAK1/2 inhibitor and the like.

The liposomes or SLNPs comprising AR Prodrugs can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, laparib b, bevacizumab, bexarotene, baricitinib, bleomycin, laparib b, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, laparib, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib and zoledronate.

Other anti-cancer agent(s) include antibody therapeutics such as trastuzumab (Herceptin), antibodies to costimulatory molecules such as CTLA-4 (e.g., ipilimumab), 4-1BB (e.g., urelumab, utomilumab), antibodies to PD-1 and PD-L1/L2, or antibodies to cytokines (IL-10, TGF-beta, etc.).

Examples of antibodies to PD-1 and/or PD-L1/L2 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

In addition, liposomes or SLNPs comprising AR Prodrugs of the present disclosure can be used in combination with one or more immune checkpoint inhibitors for the treatment of diseases, such as cancer or infections. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2.

In some embodiments, the immune checkpoint molecule is a stimulatory checkpoint molecule selected from CD27, CD28, CD40, ICOS, OX40, GITR and CD137. In further embodiments, the immune checkpoint molecule is an inhibitory checkpoint molecule selected from A2aR, B7-H3, B7-H4, BTLA, CTLA-4, IDO, KIR, LAG3, PD-1, TIM3, and VISTA. In further embodiments, the liposomes or SLNPs comprising AR Prodrugs provided herein can be used in combination with one or more agents selected from KIR inhibitors, TIGIT inhibitors, LAIR1 inhibitors, CD160 inhibitors, 2B4 inhibitors and TGF beta ("TGFβ") inhibitors.

X.) Methods of Delivering Nanocarriers Comprising AR Prodrugs to a Cell Expressing A2aR As it is known in the art, a wide variety of compositions and methods for using prodrugs and/or nanocarriers to kill tumor cells are known in the art. In the context of cancers, typical methods entail administering to a mammal having a tumor, a biologically effective amount of an AR prodrug of the disclosure, and/or a nanocarrier of the disclosure comprising an AR prodrug.

A typical embodiment is a method of delivering a therapeutic agent to a cell expressing A2aR, comprising forming an AR prodrug by conjugating a drug moiety of the disclosure with a lipid of the disclosure via a Linkage Unit, and exposing the cell to the AR prodrug.

In one embodiment, the AR prodrug comprises a drug moiety of Formula I and CHEMS conjugated via a LU comprising a hydromethylcarbamate linker.

In one embodiment, the AR prodrug comprises a drug moiety of Formula I and Stearic Acid conjugated via a LU comprising a hydromethylcarbamate linker.

In one embodiment, the AR prodrug comprises an AR5-Prodrug, whereby the lipid moiety comprises CHEMS conjugated via a LU comprising a hydromethylcarbamate linker.

In one embodiment, the AR prodrug comprises an AR5-Prodrug, whereby the lipid moiety comprises Stearic Acid conjugated via a LU comprising a hydromethylcarbamate linker.

Another illustrative embodiment is a method of treating an individual suspected of suffering from metastasized cancer, comprising a step of administering parenterally to said individual a pharmaceutical composition comprising a therapeutically effective amount of an AR prodrug produced by conjugating a drug moiety with a lipid of the disclosure via a Linkage Unit, and exposing the cell to the AR prodrug.

In one embodiment, the AR prodrug comprises a drug moiety of Formula I and CHEMS conjugated via a LU comprising a hydromethylcarbamate linker.

In one embodiment, the AR prodrug comprises a drug moiety of Formula I and Stearic Acid conjugated via a LU comprising a hydromethylcarbamate linker.

In one embodiment, the AR prodrug comprises an AR5-Prodrug, whereby the lipid moiety comprises CHEMS conjugated via a LU comprising a hydromethylcarbamate linker.

In one embodiment, the AR prodrug comprises an AR5-Prodrug, whereby the lipid moiety comprises Stearic Acid conjugated via a LU comprising a hydromethylcarbamate linker.

AR Prodrugs, SLNPs, liposomes, co-formulated liposomes, and co-formulated SLNPs of the present disclosure inhibit the activity of A2aR protein/protein interaction and, thus, are useful in treating diseases and disorders associated with activity of A2aR and the diseases and disorders associated with kinase inhibition. In further embodiments of the disclosure, the AR Prodrugs, liposomes, SLNPs, or pharmaceutically acceptable salts or stereoisomers thereof, are useful for therapeutic administration to enhance, stimulate and/or increase immunity in cancer, chronic infection, or sepsis, including enhancement of response to vaccination.

In further embodiments, the present disclosure provides a method for inhibiting the A2aR T-cell function. The method includes administering to an individual or a patient an AR prodrug, liposomes, SLNPs, and/or of any of the formulas as described herein (e.g., AR1, AR2, AR3, AR4, AR5, and/or an AR5-Prodrug), or of an AR prodrug, liposomes, SLNP, and nano-encapsulated A2aR inhibitor prodrugs as recited in any of the claims and described herein, or a pharmaceutically acceptable salt or a stereoisomer thereof. The AR prodrug, liposomes, SLNPs, and nano encapsulated A2aR inhibitor prodrugs of the present disclosure can be used alone, in combination with other agents or therapies or as an adjuvant or neoadjuvant for the treatment of diseases or disorders, including cancer and other diseases. For the uses and methods described herein, any of the AR Prodrugs, liposomes, SLNPs, and nano-encapsulated AR Prodrugs of the disclosure, including any of the embodiments thereof, may be used.

In addition, The AR Prodrugs, liposomes, SLNPs, and nano-encapsulated AR Prodrugs of the present disclosure inhibit A2aR and/or T-cell function, resulting in an A2aR pathway blockade.

In further embodiments, the present disclosure provides treatment of an individual or a patient in vivo using AR Prodrugs, liposomes, SLNPs, and nano-encapsulated AR Prodrug or a salt or stereoisomer thereof such that growth of cancerous tumors is inhibited.

AR Prodrugs, liposomes, SLNPs, and nano-encapsulated AR Prodrugs, or of any of the formulas as described herein (e.g., AR5-Prodrug), or AR Prodrugs, liposomes, SLNPs, and nano-encapsulated AR Prodrugs as recited in any of the claims and described herein, or a salt or stereoisomer thereof, can be used to inhibit the growth of cancerous tumors.

In the alternative, AR Prodrugs, liposomes, SLNPs, and nano-encapsulated AR Prodrugs of the disclosure, or of any of the formulas as described herein, or a compound as recited in any of the claims and described herein (e.g., AR5-Prodrug), or a salt or stereoisomer thereof, can be used in conjunction with other agents or standard cancer treatments, as described in this disclosure.

In a further embodiment, the present disclosure provides a method for inhibiting growth of tumor cells in vitro. The method includes contacting the tumor cells in vitro with AR Prodrugs, liposomes, SLNPs, and nano-encapsulated AR Prodrugs of the disclosure, or of any of the formulas as described herein (e.g., AR5-Prodrug), or of an AR prodrug, liposomes, SLNPs, and nano-encapsulated AR Prodrugs as recited in any of the claims and described herein, or of a salt or stereoisomer thereof.

In a further embodiment, the present disclosure provides a method for inhibiting growth of tumor cells in a patient. The method includes contacting the tumor cells with AR Prodrugs, liposomes, SLNPs, and nano-encapsulated AR Prodrugs of the disclosure, or of any of the formulas as described herein (e.g., AR5-Prodrug), or of an AR prodrug, liposomes, SLNPs, and nano-encapsulated AR Prodrugs as recited in any of the claims and described herein, or of a salt or stereoisomer thereof.

XII.) Methods of Treating Cancer(s) and Other Immunological Disorder(s)

Another embodiment of the present disclosure is a method for treating cancer. The method comprises administering to a patient, a therapeutically effective amount of a nanocarrier comprising an AR Prodrug (i.e., AR5-Prodrug) herein, a compound as recited in any of the claims and described herein, or a salt thereof. Examples of cancers include those whose growth may be inhibited using A2aR inhibitors of the disclosure and AR Prodrugs of the disclosure and cancers typically responsive to immunotherapy.

In some embodiments, the present disclosure provides a method of enhancing, stimulating and/or increasing the immune response in a patient. The method includes administering to the patient a therapeutically effective amount of an AR prodrug and/or a liposome or SLNP comprising the same (i.e., AR5-Prodrug), a compound or composition as recited in any of the claims and described herein, or a salt thereof.

Non-limiting examples of cancers that are treatable using the nanocarriers comprising AR Prodrugs, AR Prodrugs and co-formulated liposomes or SLNPs of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers, especially metastatic cancers that express A2aR.

In some embodiments, cancers treatable with liposomes, SLNPs, or AR Prodrugs of the present disclosure include melanoma (e.g., metastatic malignant melanoma), renal cancer (e.g. clear cell carcinoma), prostate cancer (e.g. hormone refractory prostate adenocarcinoma), breast cancer, colon cancer, lung cancer (e.g. non-small cell lung cancer and small cell lung cancer), squamous cell head and neck cancer, urothelial cancer (e.g. bladder) and cancers with high microsatellite instability (MSI$^{high}$). Additionally, the disclosure includes refractory or recurrent malignancies whose growth may be inhibited using the liposomes, SLNPs, or AR Prodrugs or co-formulated liposomes or SLNPs of the disclosure.

In additional embodiments, cancers that are treatable using the formulated and/or co-formulated liposomes or SLNPs, or AR Prodrugs of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In further embodiments, cancers that are treatable using the formulated and/or co-formulated liposomes, SLNPs, or AR Prodrugs of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In addition, in some embodiments, the formulated and/or co-formulated liposomes, SLNPs, or AR Prodrugs of the present disclosure can be used to treat sickle cell disease and sickle cell anemia.

Furthermore, in some embodiments, diseases and indications that are treatable using the formulated and/or co-formulated liposomes, SLNPs, or AR Prodrugs of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, hamartoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors.

Exemplary nervous system cancers include cancers of the skull (osteoma, hemangioma, granuloma, xanthoma, osteitis deformans), meninges (meningioma, meningiosarcoma, gliomatosis), brain (astrocytoma, neuroblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Additionally, A2aR, and/or kinase pathway blockade with formulated and/or co-formulated liposomes, SLNPs, or AR Prodrugs of the present disclosure can also be used for treating infections such as viral, bacteria, fungus, and parasite infections.

The present disclosure provides a method for treating infections such as viral infections. The method includes administering to a patient, a therapeutically effective amount of a formulated and/or co-formulated liposome, SLNP, or AR Prodrugs or any of the formulas as described herein (i.e., AR5-Prodrug) as recited in any of the claims and described herein, a salt thereof.

Examples of viruses causing infections treatable by methods of the present disclosure include, but are not limit to, human immunodeficiency virus, human papillomavirus, influenza, hepatitis A, B, C or D viruses, adenovirus, poxvirus, herpes simplex viruses, human cytomegalovirus, severe acute respiratory syndrome virus, Ebola virus, and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

In addition, the present disclosure provides a method for treating bacterial infections. The method includes administering to a patient, a therapeutically effective amount of a formulated and/or co-formulated liposome, SLNP, or AR Prodrugs, or any of the formulas as described herein (i.e., AR5-Prodrug) as recited in any of the claims and described herein, or a salt thereof.

Examples of pathogenic bacteria causing infections treatable by methods of the disclosure, include but are not limited to, chlamydia, rickettsia bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

In addition, the present disclosure provides a method for treating fungus infections. The method includes administering to a patient, a therapeutically effective amount of a formulated and/or co-formulated liposome, SLNP, or AR Prodrugs, or any of the formulas as described herein (i.e., AR5-Prodrug) as recited in any of the claims and described herein, or a salt thereof.

Examples of pathogenic fungi causing infections treatable by methods of the disclosure include, but are not limited to, Candida (albicans, krusei, glabrata, tropicalis, etc.), *Cryptococcus neoformans*, Aspergillus (fumigatus, Niger, etc.), Genus Mucorales (Mucor, absidia, rhizophus), *Sporothrix schenkii, Blastomyces dermatitidis, Paracoccidioides brasiliensis, Coccidioides immitis* and *Histoplasma capsulatum.*

Additionally, the present disclosure provides a method for treating parasite infections. The method includes administering to a patient, a therapeutically effective amount of a formulated and/or co-formulated liposome, SLNP, or AR Prodrugs, or any of the formulas as described herein (i.e., AR5-Prodrug) as recited in any of the claims and described herein, or a salt thereof.

Examples of pathogenic parasites causing infections treatable by methods of the disclosure include, but are not limited to, *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi,* and *Nippostrongylus brasiliensis.*

In a further set of embodiments that are within the scope of this disclosure, the formulated and/or co-formulated liposomes, nanocarrier, SLNP, or AR Prodrugs, or any of the formulas as described herein (i.e. AR5-Prodrug) are useful in preventing or reducing the risk of developing any of the diseases referred to in this disclosure; e.g., preventing or reducing the risk of developing a disease, condition or disorder in an individual who may be predisposed to the disease, condition or disorder but does not yet experience or display the pathology or symptomatology of the disease.

In one embodiment, the methods described herein comprise LNP-AR5 and/or a therapeutically effective amount of LNP-AR5.

In one embodiment, the methods described herein comprise SLNP-AR5 and/or a therapeutically effective amount of SLNP-AR5.

XIII.) Kits/Articles of Manufacture

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise a formulated and/or co-formulated liposome that is or can be detectably labeled and/or is loaded with an AR prodrug of the disclosure. Kits can comprise a container comprising a drug unit. The kit can include all or part of the formulated and/or co-formulated nanocarriers, liposomes, SLNPs, and/or an AR prodrug.

The kit of the invention will typically comprise the container described above, and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a cancer or other immunological disorder.

The terms "kit" and "article of manufacture" can be used as synonyms.

In another embodiment of the invention, an article(s) of manufacture containing compositions, such as formulated and/or co-formulated nanocarriers, liposomes, SLNPs, and/or AR Prodrugs are within the scope of this disclosure. The article of manufacture typically comprises at least one container and at least one label. Suitable containers include, for example, bottles, vials, syringes, and test tubes. The containers can be formed from a variety of materials such as glass, metal, or plastic. The container can hold formulated and/or co-formulated liposomes loaded with AR Prodrugs.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be formulated and/or co-formulated nanocarriers, liposomes, or SLNPs loaded with AR Prodrugs and/or AR Prodrugs as disclosed herein.

The article of manufacture can further comprise a second container comprising a pharmaceutically acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

In one embodiment, the kit or article of manufacture comprises LNP-AR5 and/or a therapeutically effective amount of LNP-AR5.

In one embodiment, the kit or article of manufacture comprises SLNP-AR5 and/or a therapeutically effective amount of SLNP-AR5.

EXEMPLARY EMBODIMENTS

1) An AR prodrug composition comprising,
   (i) a drug moiety;
   (ii) a lipid moiety; and
   (iii) a linkage unit ("LU"),
   whereby the drug moiety comprises an A2aR antagonist and whereby the LU conjugates the drug moiety with the lipid moiety.
2) The AR prodrug of claim 1, further comprising the chemical structure set forth in FORMULA I.
3) The AR prodrug of claim 1, wherein the drug moiety comprises the chemical structure set forth as AR5.
4) The AR prodrug of claim 1, wherein the LU is a hydromethylcarbamate linker.
5) The AR prodrug of claim 1, wherein the lipid moiety comprises a lipid set forth in Table I.
6) The AR prodrug of claim 1, wherein the lipid moiety comprises a lipid set forth in Table III.
7) The AR prodrug of claim 1, wherein the lipid moiety comprises CHEMS.
8) The AR prodrug of claim 1, wherein the lipid moiety comprises Stearic Acid.
9) The AR prodrug of claim 1, wherein the drug moiety comprises the chemical structure set forth as AR5 and wherein the lipid moiety comprises Stearic acid and wherein the compound has the following chemical structure:

10) An AR prodrug composition comprising,
    (i) a drug moiety, whereby the drug moiety comprises AR5;
    (ii) a lipid moiety, whereby the lipid moiety comprises CHEMS; and
    (iii) LU, whereby the LU comprises a hydromethylcarbamate linker.

11) An AR prodrug composition comprising,
    (i) a drug moiety, whereby the drug moiety comprises AR5;
    (ii) a lipid moiety, whereby the lipid moiety comprises Stearic Acid; and
    (iii) a LU, whereby the LU comprises a hydromethyl-carbamate linker.

12) An AR prodrug composition of claim 11, having the following chemical structure:

13) A nanocarrier comprising, an AR prodrug whereby the nanocarrier releases an active A2aR inhibitor after cleavage of a LU.

14) The nanocarrier of claim 13, wherein the LU is a hydromethylcarbamate linker.

15) The nanocarrier of claim 13, further comprising a helper lipid, whereby the helper lipid is set forth in Table II.

16) The nanocarrier of claim 13, wherein the AR prodrug comprises AR5.

17) The nanocarrier of claim 13, wherein the nanocarrier is a liposome.

18) The liposome of claim 17, wherein the AR prodrug comprises AR5 and is denoted LNP-AR5.

19) The liposome of claim 18, whereby the liposome is further co-formulated with one or more immune modulating agent or a lipid-prodrug thereof, wherein the immune modulating agent is selected from the group consisting of immunogenic-cell death inducing chemotherapeutics, toll-like receptor agonists, STING agonists, CTLA-4 inhibitors, IDO inhibitors, PD-1/PD-L1 inhibitors, CD1D agonists and/or prodrugs thereof.

20) The liposome of claim 18, whereby the liposome is further co-formulated with an ICD-inducing chemotherapeutic, wherein the ICD-inducing chemotherapeutic is selected from the group consisting of DOX, MTO, OXA, CP, Bortezomib, Carfilzimib, or Paclitaxel.

21) The liposome of claim 18, further comprising DOX.

22) The liposome of claim 18, further comprising MTO.

23) The liposome of claim 20, further comprising DOX.

24) The liposome of claim 20, further comprising MTO.

25) The liposome of claim 18, whereby the liposome is further co-formulated with a toll-receptor agonist or a lipid-prodrug thereof, wherein the toll-receptor agonist is selected from the group consisting of Resiquimod (R848), Gardiquimod, 852A, DSR 6434, Telratolimod, CU-T12-9, monophosphoryl Lipid A (MPLA), 3D (6-acyl)-PHAD®, SMU127, Pam3CSK4, TR5, TR6, TR3, or 3D-PHAD®.

26) The liposome of claim 18, whereby the liposome is further co-formulated with a PD-1/PD-L1 antagonist or a lipid-prodrug thereof, wherein the PD-1/PD-L1 antagonist is selected from the group consisting of AUNP12, CA-170, PD3, or BMS-986189.

27) The liposome of claim 18, whereby the liposome is further co-formulated with a TGFβ antagonist, wherein the TGFb antagonist is selected from the group consisting of TB4.

28) The liposome of claim 18, whereby the liposome is further co-formulated with an IDO inhibitor, wherein the IDO inhibitor is selected from the group consisting of ID3.

29) A kit comprising a nanocarrier of any one of claims 13-17.

30) A kit comprising a liposome of any one of claims 18-28.

31) The nanocarrier of claim 13, wherein the nanocarrier is a solid-lipid nanoparticle (SLNP).

32) The nanocarrier of claim 16, wherein the nanocarrier is a solid-lipid nanoparticle (SLNP).

33) The SLNP of claim 31, wherein the AR prodrug comprises AR5 and is denoted SLNP-AR5.

34) The nanocarrier of claim 32, denoted SLNP-AR5.

35) The SLNP of claim 31, whereby the SLNP is further co-formulated with one or more immune modulating agent or a lipid-prodrug thereof, wherein the immune modulating agent is selected from the group consisting of immunogenic-cell death inducing chemotherapeutics, toll-receptor agonists, STING agonists, CTLA-4 inhibitors, IDO inhibitors, PD-1/PD-L1 inhibitors, CD1D agonists and/or prodrugs thereof.

36) The SLNP of claim 31, whereby the SLNP is further co-formulated with an ICD-inducing chemotherapeutic, wherein the ICD-inducing chemotherapeutic is selected from the group consisting of DOX, MTO, OXA, CP, Bortezomib, Carfilzimib, or Paclitaxel.

37) The SLNP of claim 31, further comprising DOX.

38) The SLNP of claim 31, further comprising MTO.

39) The SLNP of claim 33, further comprising DOX.

40) The SLNP of claim 33, further comprising MTO.

41) The SLNP of claim 31, whereby the liposome is further co-formulated with a toll-receptor agonist or a lipid-prodrug thereof, wherein the toll-receptor agonist is selected from the group consisting of Resiquimod (R848), Gardiquimod, 852A, DSR 6434, Telratolimod, CU-T12-9, monophosphoryl Lipid A (MPLA), 3D (6-acyl)-PHAD®, SMU127, Pam3CSK4, or 3D-PHAD®.

42) The SLNP of claim 31, whereby the liposome is further co-formulated with a PD-1/PD-L1 antagonist or a lipid-prodrug thereof, wherein the PD-1/PD-L1 antagonist is selected from the group consisting of AUNP12, CA-170, or BMS-986189.

43) The SLNP of claim 31, whereby the SLNP is further co-formulated with a PD-1/PD-L1 antagonist or a lipid-prodrug thereof, wherein the PD-1/PD-L1 antagonist is selected from the group consisting of AUNP12, CA-170, PD3, or BMS-986189.

44) The SLNP of claim 31, whereby the SLNP is further co-formulated with a TGFβ antagonist, wherein the TGFβ antagonist is selected from the group consisting of TB4.

45) The SLNP of claim 31, whereby the SLNP is further co-formulated with an IDO inhibitor, wherein the IDO inhibitor is selected from the group consisting of ID3.

46) A kit comprising a SLNP of any one of claims 31-45.

47) A method of treating a subject suffering or diagnosed with cancer comprising,
    (i) administering to a subject in need of such treatment an effective amount of a nanocarrier, wherein the nanocarrier comprises an AR prodrug; and
    (ii) a pharmaceutically acceptable salt thereof.

48) The method of claim 47, wherein the AR prodrug comprises an AR5-Prodrug.

49) The method of claim 47, wherein the nanocarrier comprises an AR5-Prodrug further co-formulated with and ICD-inducing chemotherapeutic.

50) The method of claim 47, wherein the nanocarrier comprises an AR5-Prodrug further co-formulated with an immune modulating agent.

51) The method of claim 47, wherein the nanocarrier is a liposome.

52) The method of claim 47, wherein the liposome is LNP-AR5.

53) The method of claim 47, wherein the nanocarrier is a solid-lipid nanoparticle.

54) The method of claim 53, wherein the SLNP is SLNP-AR5.

55) The method of claim 52, wherein LNP-AR5 is used in combination with a PD-1 antibody, a CTLA4 antibody, or an immunogenic cell death inducing chemotherapy drug (e.g., DOX or MTO).

56) The method of claim 54, wherein SLNP-AR5 is used in combination with a PD-1 antibody, a CTLA4 antibody, or an immunogenic cell death inducing chemotherapy drug (e.g., DOX or MTO).

57) A method of treating a subject suffering or diagnosed with cancer comprising,
    (i) administering to a subject in need of such treatment an effective amount of a nanocarrier, wherein the nanocarrier comprises an AR prodrug; and
    (ii) a pharmaceutically acceptable salt thereof.

58) The method of claim 57, wherein the AR prodrug comprises an AR5-Prodrug.

59) The method of claim 57, wherein the nanocarrier comprises an AR5-Prodrug further co-formulated with and ICD-inducing chemotherapeutic.

60) The method of claim 57, wherein the nanocarrier comprises an AR5-Prodrug further co-formulated with an immune modulating agent.

61) The method of claim 57, wherein the nanocarrier is a solid-lipid nanoparticle ("SLNP").

62) The method of claim 61, wherein the SLNP is SLNP-AR5.

63) The method of claim 57, wherein the nanocarrier is a liposome.

64) The method of claim 63, wherein the liposome is LNP-AR5.

65) A AR5 Prodrug having the following chemical structure:

66) A liposome comprising the AR5 Prodrug of claim 65.

67) A liposome comprising the AR5 Prodrug of claim 65, further comprising a helper lipid.

68) A liposome of claim 67, wherein the helper lipid is set forth in Table II.

69) A solid-lipid nanoparticle (SLNP) comprising the AR5 Prodrug of claim 65.

70) A liposome of claim 65, denoted LNP-AR5.

71) The SLNP of claim 69, denoted SLNP-AR5.

72) The liposome of claim 70 co-formulated with TR5.

73) The liposome of claim 70 co-formulated with TR6.

74) The liposome of claim 70 co-formulated with ID3.

75) The liposome of claim 70 co-formulated with PD3.

76) The liposome of claim 70 co-formulated with MTO.

77) The liposome of claim 70 co-formulated with MTO and ID3.

78) The liposome of claim 70 co-formulated with MTO and TR5.

79) The SLNP of claim 71 co-formulated with TR5.

80) The SLNP of claim 71 co-formulated with TR6.

81) The SLNP of claim 71 co-formulated with ID3.

82) The SLNP of claim 71 co-formulated with PD3.

83) The SLNP of claim 71 co-formulated with MTO and ID3.

84) The SLNP of claim 71 co-formulated with MTO and PD3.

85) A composition comprising a liposome wherein the liposome further comprises AR5 co-formulated with TR3 (denoted LNP-AR5-TR3).

86) A composition comprising a liposome wherein the liposome further comprises AR5 co-formulated with TR5 (denoted LNP-AR5-TR5).

87) A composition comprising a liposome wherein the liposome further comprises AR5 co-formulated with ID3 (denoted LNP-AR5-ID3).

88) A composition comprising a liposome wherein the liposome further comprises AR5 co-formulated with TB4 (denoted LNP-AR5-TB4).

89) A composition comprising a liposome wherein the liposome further comprises AR5 co-formulated with PD3 (denoted LNP-AR5-PD3).

90) A composition comprising a solid-lipid nanoparticle (SLNP) wherein the SLNP further comprises AR5 co-formulated with TR3 (denoted SLNP-AR5-TR3).

91) A composition comprising a solid-lipid nanoparticle (SLNP) wherein the SLNP further comprises AR5 co-formulated with TR5 (denoted SLNP-AR5-TR5).

92) A composition comprising a solid-lipid nanoparticle (SLNP) wherein the SLNP further comprises AR5 co-formulated with ID3 (denoted SLNP-AR5-ID3).

93) A composition comprising a solid-lipid nanoparticle (SLNP) wherein the SLNP further comprises AR5 co-formulated with TB4 (denoted SLNP-AR5-TB4).

94) A composition comprising a solid-lipid nanoparticle (SLNP) wherein the SLNP further comprises AR5 co-formulated with PD3 (denoted SLNP-AR5-PD3).

EXAMPLES

Various aspects of the invention are further described and illustrated by way of the several examples that follow, none of which is intended to limit the scope of the invention.

Example 1: Chemical Synthesis of AR5 Prodrug Comprising Stearic Acid

Figure 1:
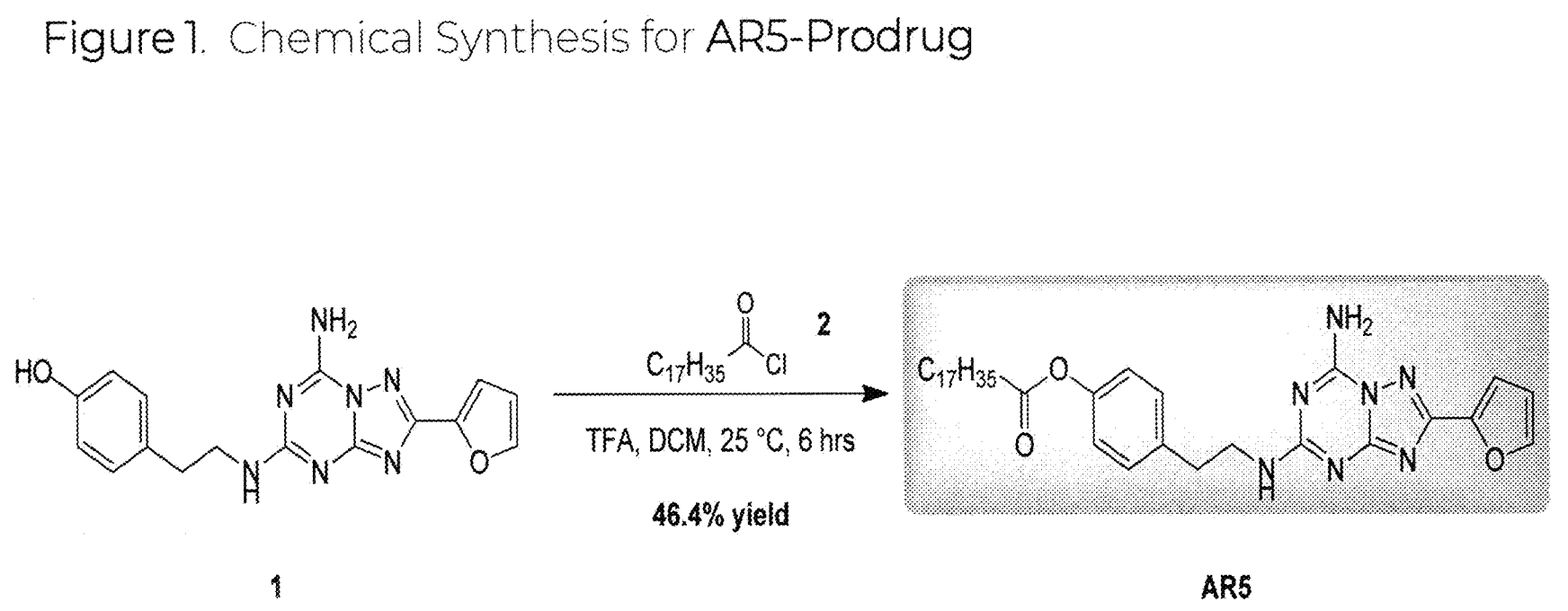

Chemical synthesis of an AR5 prodrug comprising Stearic Acid was synthesized using the protocol. Briefly, to a solution of Compound 1 (2.75 g, 8.15 mmol, 1.00 eq) and TFA (12.0 g, 105 mmol, 7.85 mL, 13.0 eq) in DCM (150 mL) was added slowly to Compound 2 (7.41 g, 24.5 mmol, 3.00 eq) at 25° C. The mixture was stirred at 25° C. for six (6) hrs. LCMS showed that the Compound 1 was consumed and 92.3% the desired mass (RT=1.371 mins) was detected. The reaction mixture was concentrated under vacuum at 25° C. to get the crude product. The solid was diluted with DCM (1.00 L) and was adjusted with saturated aqueous NaHCO$_3$ until pH=8 and the aqueous layer was extracted with dichloromethane (500 mL*1). The combined organic layer was washed with brine (500 mL), dried over Na$_2$SO$_4$, concentrated under vacuum. The residue was purified by column chromatography (SiO$_2$, Petroleum ether/Ethyl acetate=5/1 to 1/1) and column chromatography (SiO$_2$, Dichloromethane: Methanol=I/O to 5/1) to give the crude product. The crude product was triturated with ethyl acetate (120 mL) 15° C. for 0.5 hr (R$_f$=0.50). The product (600 mg) was combined for analysis and delivery. Finally, 3.24 g product was noted and delivered as a distinct batch number. Compound AR5 (3.24 g, 5.15 mmol, 46.4% yield, 95.9% purity) was obtained as a white solid and confirmed by LCMS, $^1$H NMR, F NMR, NOE, and MS. (FIG. 1). The synthesis set forth in this example yields a AR5-Prodrug comprising Stearic Acid with the following chemical structure:

Example 2: Synthesis and Characterization of LNP-AR5 Liposome

In another experiment, a liposome comprising the AR5 prodrug (denoted LNP-AR5) was synthesized in the following manner. Briefly, in the first step, using a molar ratio of 52:30:14:4 of HSPC:CHOL:AR5:DSPE-PEG, we synthesized an LNP-AR5. The optimized ratio of the lipid mixture at the molar ratio of 52:30:14:4 was preheated at 55 degree(s) centigrade using the heating block attachment in the microfluidizer. The final concentration of the lipid mixture was 2.5 mg/ml. The aqueous phase containing 1 mM PBS buffer was also preheated at 55 degrees centigrade before passing through the microfluidics cartridge at the flow rate of 3:1 (aqueous: organic phase, lipid mixture). The solvent was removed using dialysis membrane of cut off 12 Kda size (Sigma Aldrich) against DI water for at least twenty-four (24) hrs. The dialysis water was changed at least five (5) times during a twenty-four (24) hr. period to maximize the removal of the solvent. After the removal of the solvent, the LNP-AR5 was concentrated according to the need using an Amicon centrifugal filtration device (cut off size 10 Kda, at 3000 g).

Characterization of the LNP-AR5 liposome was determined using a Malvern Zetasizer (Malvern Instrumentation Co., Westborough, MA, USA). Briefly, two (2) ml of LNP-AR5 liposomes (concentration of the liposome was of 0.5-1 mg/ml) was placed in a 4-sided, clear, plastic cuvette and analyzed directly at 25° C. The results shown in FIG. 5 show the Zav size of the nanoparticles were approximately 87.29 nm with a PDI of approximately 0.272.

Additionally, Zeta potential of the LNP-AR5 liposomes in aqueous dispersion was determined using a Malvern zeta seizer Instrument (Malvern Instrumentation Co, Westborough, MA, USA). Briefly, approximately one (1) ml of the liposome (concentration approximately 2 mg/ml in 20 mM NaCl) was placed in a disposable capillary zeta potential cell available for the Zetasizer. The measurement was done at 25° C. The results show the Zeta potential determination of LNP-AR5 was approximately-18.6 mV (FIG. 6).

Example 3: Synthesis and Characterization of LNP-AR5-TR5 Liposome

In another experiment, a liposome comprising the AR5 prodrug co-formulated with a TR5 prodrug (denoted LNP-AR5-TR5) was synthesized in the following manner. Briefly, in the first step, a lipid stock solution of HSPC, CHOL, DSPE-PEG, AR5 prodrug, and TR5 were prepared in ethanol (20 mg/ml) separately. A lipid mixture of HSPC, CHOL, AR5, TR5 and DSPE-PEG at a molar ratio of 52:31:9:3:5 was prepared by mixing the lipid stock solutions and was then diluted with ethanol (to get a lipid concentration of 2.5 mg/ml). This lipid mixture was heated at 55-60 degree centigrade using the heating block attachment in the microfluidizer. The aqueous phase containing 1 mM PBS buffer was also preheated at 55-60 degree centigrade before passing through the microfluidics cartridge at the flow rate of 4.5:1 (aqueous: organic phase, lipid mixture). The solvent was removed using dialysis membrane of cut off 12 Kda size (Sigma Aldrich) against DI water for at least 24 hrs. The dialysis water was changed at least five (5) times during the period of 24 hrs. to maximize the removal of the solvent. After the removal of the solvent, the LNP-AR5-TR5 was concentrated according to the need using Amicon centrifugal filtration device (cut off size 10 Kda, at 3000 g).

Characterization of the LNP-AR5-TR5 liposome was determined using a Malvem Zetasizer (Malvern Instrumentation Co., Westborough, MA, USA). Briefly, two (2) ml of LNP-AR5-TR5 liposomes (concentration of the liposome was of 0.5-1 mg/ml) was placed in a 4-sided, clear, plastic cuvette and analyzed directly at 25° C. The results shown in FIG. 7 show the Zav size of the nanoparticles were approximately 81.26 nm with a PDI of approximately 0.165.

Additionally, Zeta potential of the LNP-AR5-TR5 liposomes in aqueous dispersion was determined using a Malvern zeta seizer Instrument (Malvern Instrumentation Co, Westborough, MA, USA). Briefly, approximately one (1) ml of the liposome (concentration approximately 2 mg/ml in 20 mM NaCl) was placed in a disposable capillary zeta potential cell available for the Zetasizer. The measurement was done at 25° C. The results show the Zeta potential determination of LNP-AR5-TR5 was approximately-13.2 mV (FIG. 8).

Example 4: Synthesis and Characterization of LNP-AR5-ID3 Liposome

In another experiment, a liposome comprising the AR5 prodrug co-formulated with an ID3 prodrug (denoted LNP-AR5-ID3) was synthesized in the following manner. Briefly, in the first step, a lipid stock solution of HSPC, CHOL, DSPE-PEG, AR5 prodrug, and ID3 were prepared in ethanol (20 mg/ml) separately. A lipid mixture of HSPC, CHOL, AR5, ID3 and DSPE-PEG at a molar ratio of 52:23:8:8:5 was prepared by mixing the lipid stock solutions and was then diluted with ethanol (to get a lipid concentration of 2.5 mg/ml). This lipid mixture was heated at 55-60 degree centigrade using the heating block attachment in the microfluidizer. The aqueous phase containing 1 mM PBS buffer was also preheated at 55-60 degree centigrade before passing through the microfluidics cartridge at the flow rate of 3.5:1 (aqueous: organic phase, lipid mixture). The solvent was removed using dialysis membrane of cut off 12 Kda size (Sigma Aldrich) against DI water for at least 24 hrs. The dialysis water was changed at least five (5) times during the period of 24 hrs. to maximize the removal of the solvent. After the removal of the solvent, the LNP-AR5-ID3 was concentrated according to the need using Amicon centrifugal filtration device (cut off size 10 Kda, at 3000 g).

Characterization of the LNP-AR5-ID3 liposome was determined using a Malvern Zetasizer (Malvern Instrumentation Co., Westborough, MA, USA). Briefly, two (2) ml of LNP-AR5-ID3 liposomes (concentration of the liposome was of 0.5-1 mg/ml) was placed in a 4-sided, clear, plastic cuvette and analyzed directly at 25° C. The results shown in FIG. 9 show the Zav size of the nanoparticles were approximately 91.00 nm with a PDI of approximately 0.212.

Additionally, Zeta potential of the LNP-AR5-ID3 liposomes in aqueous dispersion was determined using a Malvern zeta seizer Instrument (Malvern Instrumentation Co, Westborough, MA, USA). Briefly, approximately one (1) ml of the liposome (concentration approximately 2 mg/ml in 20 mM NaCl) was placed in a disposable capillary zeta potential cell available for the Zetasizer. The measurement was done at 25° C. The results show the Zeta potential determination of LNP-AR5-ID3 was approximately-14.1 mV (FIG. 10).

Example 5: Synthesis and Characterization of LNP-AR5-TR5-ID3 Liposome

In another experiment, a liposome comprising the AR5 prodrug co-formulated with an ID3 prodrug and further co-formulated with a TR5 prodrug (denoted LNP-AR5-TR5-ID3) was synthesized in the following manner. Briefly, in the first step, a lipid stock solution of HSPC, CHOL, DSPE-PEG, AR5 prodrug, and TR5 were prepared in ethanol (20 mg/ml) separately. The ID3 prodrug stock solution was prepared in acetonitrile (20 mg/ml). A lipid mixture of HSPC, CHOL, AR5, ID3, TR5, and DSPE-PEG at a molar ratio of 51.6:27:7:2.4:7:5 was prepared by mixing the lipid stock solutions and was then diluted with ethanol (to get a lipid concentration of 2.5 mg/ml). This lipid mixture was heated at 55-60 degree centigrade using the heating block attachment in the microfluidizer. The aqueous phase containing 1 mM PBS buffer was also preheated at 55-60 degree centigrade before passing through the microfluidics cartridge at the flow rate of 4.5:1 (aqueous: organic phase, lipid mixture). The solvent was removed using dialysis membrane of cut off 12 Kda size (Sigma Aldrich) against DI water for at least 24 hrs. The dialysis water was changed at least five (5) times during the period of 24 hrs. to maximize the removal of the solvent. After the removal of the solvent, the LNP-AR5-TR5-ID3 was concentrated according to the need using Amicon centrifugal filtration device (cut off size 10 Kda, at 3000 g).

Characterization of the LNP-AR5-AR5-ID3 liposome was determined using a Malvern Zetasizer (Malvern Instrumentation Co., Westborough, MA, USA). Briefly, two (2) ml of LNP-AR5-TR5-ID3 liposomes (concentration of the liposome was of 0.5-1 mg/ml) was placed in a 4-sided, clear, plastic cuvette and analyzed directly at 25° C. The results shown in FIG. 11 show the Zav size of the nanoparticles were approximately 96.00 nm with a PDI of approximately 0.117.

Additionally, Zeta potential of the LNP-AR5-TR5-ID3 liposomes in aqueous dispersion was determined using a Malvern zeta seizer Instrument (Malvern Instrumentation Co, Westborough, MA, USA). Briefly, approximately one (1) ml of the liposome (concentration approximately 2 mg/ml in 20 mM NaCl) was placed in a disposable capillary zeta potential cell available for the Zetasizer. The measurement was done at 25° C. The results show the Zeta potential determination of LNP-AR5-TR5-ID3 was approximately-20.5 mV (FIG. 12).

Example 6: Synthesis and Characterization of SLNP-AR5 Solid-Lipid Nanoparticle In another experiment, a solid-lipid nanoparticle comprising the AR5 (denoted SLNP-AR5) was synthesized by solvent diffusion using several types of stabilizers (e.g., Polyvinyl alcohol (e.g., Moliwol 488), poloxamers (e.g., Pluronic F-68, Pluronic F-127), Tween 80 & 20, and Kolliphor RH40, etc.) may be used a stabilizer. in the following manner. Briefly, in the first step, a lipid stock solution of DSPC, CHOL, DSPE-PEG, was prepared in ethanol (20 mg/ml). Separately, an AR5 prodrug stock solution was prepared in DMSO (20 mg/ml). A lipid mixture was obtained by mixing DSPC, CHOL, AR5 and DSPE-PEG at a molar ratio of 20:34:41:5 (with a lipid concentration of 20 mg/ml). This lipid mixture was then heated at 55-60 degree centigrade. Similarly, the aqueous phase containing the appropriate stabilizer (e.g., 5% w/v Pluronic F127) was heated using a magnetic hot plate stirrer with constant magnetic stirring (at 300-400 rpm). The lipid mixture was slowly mixed with this aqueous phase under constant stirring. Once the mixing was completed the entire mixture was sonicate using a water sonicate bath for about five (5) minutes and then again kept in the magnetic stirrer plate with constant stirring for about another 1 hour. Finally, the solvent was removed using dialysis membrane of cut off 12 Kda size (Sigma Aldrich) against DI water for at least 4-6 hrs. The dialysis water was changed at least three (3) times during this time period The. SLNP-AR5 was concentrated according to the need using Amicon centrifugal filtration device (cut off size 10 Kda, at 3000 g).

Characterization of the SLNP-AR5 was determined using a Malvern Zetasizer (Malvern Instrumentation Co., Westborough, MA, USA). Briefly, two (2) ml of SLNP-AR5 (concentration of the liposome was of 0.5-1 mg/ml) was placed in a 4-sided, clear, plastic cuvette and analyzed directly at 25° C. The results shown in FIG. 13 show the Zav size of the nanoparticles were approximately 99.06 nm with a PDI of approximately 0.174.

Additionally, Zeta potential of the SLNP-AR5 solid-lipid nanoparticle in aqueous dispersion was determined using a Malvern zeta seizer Instrument (Malvern Instrumentation Co, Westborough, MA, USA). Briefly, approximately one (1) ml of the SLNP (concentration approximately 3 mg/ml in DI water) was placed in a disposable capillary zeta potential cell available for the Zetasizer. The measurement was done at 25° C. The results show the Zeta potential determination of SLNP-AR5 was approximately −7.8 mV (FIG. 14).

Example 7: Synthesis and Characterization of SLNP-AR5-TR5 Solid-Lipid Nanoparticle In another experiment, a solid-lipid nanoparticle comprising the AR5 co-formulated with TR5 (denoted SLNP-AR5-TR5) was synthesized by solvent diffusion using various types of stabilizers (e.g., Polyvinyl alcohol (e.g., Moliwol 488), poloxamers (e.g., Pluronic F-68, Pluronic F-127), Tween 80 & 20, and Kolliphor RH40, etc.)) may be used a stabilizer. in the following manner. Briefly, in the first step, a lipid stock solution of DSPC, CHOL, DSPE-PEG, was prepared in ethanol (20 mg/ml). Separately, an AR5 prodrug stock solution was prepared in DMSO (20 mg/ml). A lipid mixture was obtained by mixing DSPC, CHOL, AR5, TR5, and DSPE-PEG at a molar ratio of 20:33:36:6:5 (with a lipid concentration of 20 mg/ml). This lipid mixture was then heated at 55-60 degree centigrade. Similarly, the aqueous phase containing the appropriate stabilizer (e.g., 5% w/v Pluronic F127) was heated using a magnetic hot plate stirrer with constant magnetic stirring (at 300-400 rpm). The lipid mixture was slowly mixed with this aqueous phase under constant stirring. Once the mixing was completed the entire mixture was sonicate using a water sonicate bath for about five (5) minutes and then again kept in the magnetic stirrer plate with constant stirring for about another 1 hour. Finally, the solvent was removed using dialysis membrane of cut off 12 Kda size (Sigma Aldrich) against DI water for at least 4-6 hrs. The dialysis water was changed at least three (3) times during this time period The. SLNP-AR5-TR5 was concentrated according to the need using Amicon centrifugal filtration device (cut off size 10 Kda, at 3000 g).

Characterization of the SLNP-AR5-TR5 was determined using a Malvern Zetasizer (Malvern Instrumentation Co., Westborough, MA, USA). Briefly, two (2) ml of SLNP-AR5-TR5 (concentration of the liposome was of 0.5-1 mg/ml) was placed in a 4-sided, clear, plastic cuvette and analyzed directly at 25° C. The results shown in FIG. 15 show the Zav size of the nanoparticles were approximately 104 nm with a PDI of approximately 0.128.

Additionally, Zeta potential of the SLNP-AR5-TR5 solid-lipid nanoparticle in aqueous dispersion was determined using a Malvern zeta seizer Instrument (Malvern Instrumentation Co, Westborough, MA, USA). Briefly, approximately one (1) ml of the SLNP (concentration approximately 3 mg/ml in DI water) was placed in a disposable capillary zeta potential cell available for the Zetasizer. The measurement was done at 25° C. The results show the Zeta potential determination of SLNP-AR5-TR5 was approximately-6.5 mV (FIG. 16).

Example 8: Tumor Inhibition of LNP-AR5 in Combination with LNP-MTO Using B16F10 Cells In Vivo In this experiment, evaluation of LNP-AR5 was performed using the following protocols. Briefly, murine mela-noma cancer B16F10 cells (cells ($0.2 \times 10^6$) were inoculated subcutaneously in the right rear flank region of C57BL/6 mice. Animals were treated with vehicle control, LNP-MTO (Mitoxantrone dihydrochloride in liposome form) at 2 mg/kg, and combination of LNP-MTO and LNP-AR5 (AR5 in liposome form) at 3 mg/kg two (2) times weekly through iv injection. Tumor volumes were measured three (3) times in two dimensions using a caliper, and the volume was calculated using the formula: $V=(L \times W \times W) \times 0.5$, where V is tumor volume, L is tumor length (the longest tumor dimension), and W is tumor width (the longest tumor dimension perpendicular to L). The tumor growth inhibition (TGI) was calculated based on the tumor size at day eighteen (18).

The results show, the combination treatment of LNP-AR5+LNP-MTO demonstrated minor anti-tumor activity. The TGI was calculated at 31.27% (p<0.05). In addition, treatment with a single agent LNP-MTO demonstrated de minimus anti-tumor activity. The TGI was calculated at 9.75% (p>0.05). (FIG. 17).

Example 9: Tumor Inhibition of LNP-AR5 in Progressive Dosing with Multiple Combination(s) Using MC38 Cells In Vivo In this experiment, evaluation of LNP-AR5 in multiple combinations using progressive dosing was performed using the following protocols. Briefly, Colorectal cancer cells ($1 \times 10^6$) were inoculated subcutaneously in the right rear flank region of C57BL/6 mice. Animals were treated with (i) vehicle control, (ii) LNP-DOX at 4 mg/kg, (iii) anti-PD1 antibody at 10 mg/kg, (iv) a combination of LNP-AR5 (AR5 in liposome form) at 4 mg/kg+LNP-TR5 (TR5 in liposome form) at 4 mg/kg for the first two (2) doses and then at two (2) mg/kg for the remainder of the study, (v) combination of LNP-AR5+LNP-TR6 (TR6 in liposome form) at 4 mg/kg, (vi) a combination of LNP-AR5+LNP-ID3 (ID3 in liposome form) at 4 mg/kg, (vii) a combination of LNP-DOX+LNP-AR5+LNP-TR6 at 4 mg/kg, (viii) a combination of LNP-DOX+LNP-AR5+LNP-ID3 at 4 mg/kg, (ix) a combination of LNP-DOX+LNP-AR5 at 4 mg/kg+LNP-TR5 at four (4) mg/kg for the first two (2) doses and 2 mg/kg for the remainder of the study, (x) combination of anti-PD1 antibody at 10 mg/kg+LNP-AR5 at 4 mg/kg+LNP-TR5 at 4 mg/kg for the first 2 doses and 2 mg/kg for the rest of the study, and (xi) a combination of LNP-ID3+LNP-AR5 at 3 mg/kg for first two doses and 3.5 mg/kg for the remainder of the study+LNP-TR5 at 3 mg/kg for the first two (2) doses and 2 mg/kg for the remainder of the study through iv injection.

In the groups that received LNP-DOX, the initial dose(s) only included LNP-DOX and subsequently the animals were dosed with other compounds. Tumor volumes were measured three (3) times in two dimensions using a caliper, and the volume was calculated using the formula: $V=(L \times W \times W) \times 0.5$, where V is tumor volume, L is tumor length (the longest tumor dimension), and W is tumor width (the longest tumor dimension perpendicular to L). The tumor growth inhibition (TGI) was calculated based on the tumor size data of day nineteen (19).

The results show treatment of LNP-DOX alone at 4 mg/kg can produce significant anti-tumor activity, The TGI was calculated at 74.39% (p<0.05). In addition, combination treatment of LNP-AR5+LNP-TR5+LNP-DOX followed by LNP-AR5+LNP-TR6+LNP-DOX followed by LNP-AR5+LNP-ID3+LNP-DOX followed by LNP-AR5+LNP-TR5+Anti-PD-1+LNP-AR5+LNP-TR5 and LNP-ID3+LNP-AR5+LNP-TR5 produces significant anti-tumor activity.

The TGI was calculated at 77.35%, 90.31%, 90.41%, 87.67%, 91.33% and 73.77%, respectively (all $p<0.05$). Finally, the MC38 model showed minor response(s) to the treatment(s) of LNP-TR6+LNP-AR5 and LNP-ID3+LNP-AR5. The TGI was calculated below twenty percent (20%). (FIG. 18).

Example 10: Tumor Inhibition of LNP-AR5 in Combination with LNP-TR5 and Anti-PD1 Antibody Using H22 Cells In Vivo In this experiment, evaluation of LNP-AR5 in combination with TR5 and an anti-PD1 antibody was performed using the following protocols. Briefly, hepatocellular carcinoma H22 cells ($1\times10^6$) were inoculated subcutaneously in the right rear flank region of Balb/c mice. Animals were treated with (i) vehicle control, (ii) anti-PD1 antibody at 10 mg/kg, (iii) a combination of LNP-AR5 (AR5 in liposome form) at 4 mg/kg+LNP-TR5 (TR5 in liposome form) at 4 mg/kg for the first two (2) doses and 2 mg/kg for the remainder of the study, and (iv) a combination of anti-PD1 antibody at 10 mg/kg+LNP-AR5 at 4 mg/kg+LNP-TR5 at 4 mg/kg for the first 2 doses and 2 mg/kg for the remainder of the study through iv injection. Tumor volumes were measured three (3) times in two dimensions using a caliper. The volume was calculated using the formula: $V=(L\times W\times W)\times 0.5$, where V is tumor volume, L is tumor length (the longest tumor dimension), and W is tumor width (the longest tumor dimension perpendicular to L). The tumor growth inhibition (TGI) was calculated based on the tumor size data at day fourteen (14).

The results show that a combination treatment with Anti-PD-1+LNP-AR5+LNP-TR5 produces significant anti-tumor activities. The TGI was calculated 74.98% (all $p<0.05$). (FIG. 19).

Example 11: Tumor Inhibition of Co-Formulated LNP-AR5/TR5 in Combination with Anti-PD1 Antibody Using EMT6 Cells In Vivo In this experiment, evaluation of a co-formulated LNP-AR5/TR5 in combination an anti-PD1 antibody was performed using the following protocols. Briefly, murine breast cancer EMT6 cells (cells ($0.5\times10^6$) were inoculated subcutaneously in the right rear flank region of Balb/c mice. Animals were treated with (i) vehicle control, (ii) LNP-AR5 (AR5 in liposome form) at 6 mg/kg, (iii) anti-PD1 antibody at 10 mg/kg, (iv) co-formulated LNP-AR5/TR5 (co-formulation of AR5 and TR5 in liposome form) at 6 mg/kg and 2 mg/kg, respectively, and (v) a combination of anti-PD1 antibody at 10 mg/kg+LNP-AR5/TR5 at 6 mg/kg and 2 mg/kg through iv injection. Tumor volumes were measured three (3) times in two dimensions using a caliper. The volume was calculated using the formula: $V=(L\times W\times W)\times 0.5$, where V is tumor volume, L is tumor length (the longest tumor dimension), and W is tumor width (the longest tumor dimension perpendicular to L). The tumor growth inhibition (TGI) was calculated based on the tumor size data of day twenty-one (21).

The results show, the combination of anti-PD1 with co-formulated LNP-AR5/TR5 produces significant anti-tumor activity. TGI was calculated at 89.54% respectively when compared to the vehicle control group ($p<0.01$). (FIG. 20).

Example 12: Ex Vivo Validation of LNP-AR5 Mechanism of Action

In this experiment, evaluation of the LNP-AR5 mechanism of action was performed in vitro using the following protocols. Briefly, C57BL/6 mouse splenocytes were activated with CD3/28 beads at bead-to-cell ratio of 1:1. Cells were treated with 5 uM CGS21680 (specific adenosine A2A receptor agonist) in presence or absence of 5 uM AR5 (free-drug) or LNP-AR5 (AR5 in liposome form). After twenty-four (24) hours the supernatant was collected, and IFN-gamma was measured by ELISA using standard methods. The results show, the AR5 and LNP-AR5 were able to reserve the inhibitory effect of CGS21680 in INF-gamma secretion showing the A2AR antagonist mechanism of action of AR5 in liposome form. (FIG. 21).

Example 12: Synthesis of Fluorescently Labelled SLNP-AR5 and LNP-AR5

In this experiment, both the LNP-AR5 and SLNP-AR5 can be fluorescently labeled using the same (respective) method(s) mentioned in the method of synthesis sections (See, Example 2 and Example 6). The fluorescent labeling was done using DSPE-PEG-Cy5.5 by replacing 0.5% DSPE-PEG with 0.5% of DSPE-PEG-Cy5.5 (in both cases SLNP-AR5 and LNP-AR5). These fluorescently labeled SLNP-AR5-Cy5.5 & LNP-Cy5.5 were used to track the nanoparticles in in vivo and ex vivo experiments. See, for example, FIG. 22 disclosed herein. The size and characterization of the Cy-5.5 labeled LNP-AR5 and SLNP-AR5 are shown in the following table:

| Sample | Size (in nm) | Zeta potential | Stabilizer |
|---|---|---|---|
| LNP-AR5-Cy5.5 | 85.6 | −12.6 mV | none |
| SLNP-AR5-Cy5.5 | 96.8 | −9.1 mV | Pluronic F 127 |

Example 13: Ex Vivo Validation of LNP-AR5 and SLNP-AR5 Delivery to Tumor

In this experiment, evaluation of the LNP-AR5 and SLNP-AR5 distribution to a tumor was performed in vitro using the following protocols. Briefly, EMT6 cells (cells $0.5\times10^6$) were inoculated subcutaneously in the right rear flank region of Balb/c mice. Animals were treated with 0.6 mg/kg of LNP-AR5 or SLNP-AR5 conjugated with Cy5.5 dye through iv injections. Seventy-two (72) hours post injections animals were euthanized and the tissues were harvested and evaluated. The level of Radiance efficiency (ROI) in each tissue was measured using IVIS imaging system using standard protocols.

The results show that the pro-drugs in liposome form (LNP-AR5) and solid-lipid nanoparticle form (SLNP-AR5) deliver drug(s) to tumors at higher levels than to more of the normal tissues. In addition, the pro-drug in solid-lipid nanoparticle format (SLNP-AR5) was bio-distributed better than the liposome format (LNP-AR5), especially in tumor area. (FIG. 22).

Example 14: Tumor Inhibition of SLNP-AR5-TR5 In Combination With SLNP-TR5 Using EMT-6 Cells In Vivo In this experiment, evaluation of SLNP-AR5-TR5 was performed using the following protocols. Briefly, EMT-6 Breast cancer cells ($0.5\times10^6$) were inoculated subcutaneously in the right rear flank region of Balb/c mice. Animals were treated with vehicle control, SLNP-TR5 at 1 mg/kg, and SLNP-AR5-TR5 1/5 mg/kg, bi-weekly for six (6) doses through iv injection. Tumor volumes were measured three (3) times in two dimensions using a caliper. The volume was calculated using the formula: $V=(L \times W \times W) \times 0.5$, where V is tumor volume, L is tumor length (the longest tumor dimension), and W is tumor width (the longest tumor dimension perpendicular to L).

The results show that treatment with SLNP-TR5 in combination with SLNP-AR5-TR5 produces significant anti-tumor activities. (FIG. 23).

Example 15: Tumor Inhibition of Co-Formulated SLNP-AR5-ID3 and SLNP-AR5-DOX In Multiple Combinations with an Anti-PD-1 Antibody or Single Agent PD3 Using H22 Cells In Vivo In this experiment, evaluation of SLNP-AR5 co-formulated with SLNP-ID3 (BMS986205-Stearic acid), DOX (Doxorubicin-HCL), PD3 (BMS-1166-Cholestrol) and an anti-PD1 antibody was performed using the following protocols. Briefly, hepatocellular carcinoma H22 cells ($1 \times 10^6$) were inoculated subcutaneously in the right rear flank region of Balb/c mice. Animals were treated with vehicle control, anti-PD1 antibody at 10 mg/kg, SLNP-AR5 at 15 mg/kg, SLNP-DOX at 1 mg/kg, SLP-AR5-ID3 at 15/15 mg/kg, SLNP-AR5-DOX at 15/1 mg/kg, a combination of anti-PD1 and SLNP-AR5-ID3, a combination of anti-PD1 and SLNP-AR5-DOX, and SLNP-AR5-ID3-DOX at 15/15/1 mg/kg bi-weekly for total of six (6) doses through iv injection.

Tumor volumes were measured three (3) times in two dimensions using a caliper. The volume was calculated using the formula: $V=(L \times W \times W) \times 0.5$, where V is tumor volume, L is tumor length (the longest tumor dimension), and W is tumor width (the longest tumor dimension perpendicular to L). The tumor growth inhibition (TGI) was calculated based on the tumor size data at day twenty (20).

The results show, treatment of Anti-PD-1 alone at 10 mg/kg (Group 2) produces minor anti-tumor activity. The TGI was calculated at 97.84% (p<0.05) when compared with vehicle treated group. In addition, monotherapy with SLNP-AR5-ID3 at 15 mg/kg did not generate obvious anti-tumor activity (TGI<5%, p>0.05) in this model. In addition, improved anti-tumor activity was observed after combining the anti-PD-1 with SLNP-AR5-ID3 at 15 mg/kg (Group 7). The TGI was 99.45% (p<0.05). Furthermore, treatments with SLNP-DOX or SLNP-AR5 generate mild to moderate anti-tumor activity. TGIs were calculated at 55.16% and 35.11% (p>0.05). It is noted that after SLNP-DOX and/or SLNP-AR5 were combined with Anti-PD-1 improved anti-tumor activity was observed. The TGI was 85.71% (p>0.05). Finally, combination treatment of SLNP-AR5-PD3-DOX produces anti-tumor activity. TGI was 68.7% (p>0.05). (FIG. 24).

Example 16: Human Clinical Trials for the Treatment of Human Carcinomas Through the Use of Formulated and/or Co-Formulated Nanocarriers Comprising AR Prodrugs Formulated and/or co-formulated nanocarriers (liposomes or SLNPs) containing AR Prodrugs are used in accordance with the present invention which specifically accumulate in a tumor cell and are used in the treatment of certain tumors and other immunological disorders and/or other diseases. In connection with each of these indications, two clinical approaches are successfully pursued.

I.) Adjunctive therapy: In adjunctive therapy, patients are treated with formulated and/or co-formulated nanocarriers (liposomes or SLNPs) containing AR Prodrugs in combination with a chemotherapeutic or pharmaceutical or biopharmaceutical agent or a combination thereof. Primary cancer targets are treated under standard protocols by the addition of formulated and/or co-formulated nanocarriers (liposomes or SLNPs) containing AR Prodrugs. Protocol designs address effectiveness as assessed by the following examples, including but not limited to, reduction in tumor mass of primary or metastatic lesions, increased progression free survival, overall survival, improvement of patient's health, disease stabilization, as well as the ability to reduce usual doses of standard chemotherapy and other biologic agents. These dosage reductions allow additional and/or prolonged therapy by reducing dose-related toxicity of the chemotherapeutic or biologic agent.

II.) Monotherapy: In connection with the use of the formulated and/or co-formulated nanocarriers (liposomes or SLNPs) containing AR Prodrugs in monotherapy of tumors, the formulated and/or co-formulated nanocarriers (liposomes or SLNPs) containing AR Prodrugs are administered to patients without a chemotherapeutic or pharmaceutical or biological agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patient's health, disease stabilization, as well as the ability to reduce usual doses of standard chemotherapy and other biologic agents.

Dosage

Dosage regimens may be adjusted to provide the optimum desired response. For example, a single formulated and/or co-formulated nanocarriers (liposomes or SLNPs) containing AR Prodrugs may be administered, several divided doses may be administered over time, or the dose may be proportionally reduced or increased as indicated by the exigencies of the therapeutic situation. "Dosage Unit Form" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention is dictated by and directly dependent on (a) the unique characteristics of the formulated and/or co-formulated nanocarriers (liposomes or SLNPs) containing AR Prodrugs, (b) the individual mechanics of the combination compound, if any, (c) the particular therapeutic or prophylactic effect to be achieved, and (d) the limitations inherent in the art of compounding such a compound for the treatment of sensitivity in individuals.

Clinical Development Plan (CDP)

The CDP follows and develops treatments of using formulated and/or co-formulated nanocarriers (liposomes or SLNPs) containing AR Prodrugs in connection with adjunctive therapy or monotherapy. Trials initially demonstrate safety and thereafter confirm efficacy in repeat doses. Trials are open label comparing standard chemotherapy and/or the current standard of therapy plus formulated and/or co-formulated nanocarriers (liposomes or SLNPs) containing AR Prodrugs. As will be appreciated, one non-limiting criteria that can be utilized in connection with enrollment of patients is expression of A2aR in a tumor as determined by standard detection methods known in the art.

It is believed that formulated and/or co-formulated nano-carriers (liposomes or SLNPs), or any of the embodiments disclosed herein, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The present invention is not to be limited in scope by the embodiments disclosed herein, which are intended as single illustrations of individual aspects of the invention, and any that are functionally equivalent are within the scope of the invention. Various modifications to the models, methods, and life cycle methodology of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE I

Examples of Lipids.

| No. | Abbreviation | Name/Chemical Formula |
| --- | --- | --- |
| 1 | CHOL | Cholesterol |
| 2 | DPPG•Na | 1,2-dipalmitoyl-sn-glycero-3-phospho-(1'-rac-glycerol) (sodium salt) |
| 3 | DMPG•Na | 1,2-dimyristoyl-sn-glycero-3-phospho-(1'-rac-glycerol) (sodium salt) |
| 4 | Lyso PC | 1-decanoyl-2-hydroxy-sn-glycero-3-phosphocholine |
| 5 | (Δ9-Cis) PG | 1,2-dioleoyl-sn-glycero-3-phospho-(1'-rac-glycerol) (sodium salt) |
| 6 | Soy Lyso PC | L-α-lysophosphatidylcholine (Soy) |
| 7 | PG | 1,2-dilauroyl-sn-glycero-3-phospho-(1'-rac-glycerol) (sodium salt) |
| 8 | PA-PEG3-mannose | 1,2-dipalmitoyl-sn-glycero-3-phospho((ethyl-1',2',3'-triazole)triethyleneglycolmannose) (ammonium salt) |
| 9 | C16 PEG2000 Ceramide | N-palmitoyl-sphingosine-1-{succinyl [methoxy(polyethylene glycol)2000]} |
| 10 | MPLA | Monophosphoryl Lipid A |

TABLE II

Examples of Helper Lipids.

| No. | Abbreviation | Name |
| --- | --- | --- |
| 1 | DOTAP | 1,2-dioleoyl-3-trimethylammonium-propane (chloride salt) |
| 2 | DODMA | 1,2-dioleyloxy-3-dimethylaminopropane |
| 3 | DLinDMA | 1,2-dilinoleyloxy-3-dimethylaminopropane |
| 4 | DLin-KC2-DMA | 2,2-dilinoleyl-4-dimethylaminoethyl-[1,3]-dioxolane |
| 5 | Δ9-Cis PE (DOPE) | 1,2-Dioleoyl-sn-glycero-3-phosphoethanolamine |
| 6 | DOPC | 1,2-dioleoyl-sn-glycero-3-phosphocholine |
| 7 | CHOL | Cholesterol |
| 8 | PEG-C-DMA | N-[(methoxy poly(ethylene glycol)2000) carbamyl]-1,2-dimyristyloxlpropyl-3-amine |
| 9 | CHEMS | cholesteryl hemisuccinate |
| 10 | DPPC | 1,2-dipalmitoyl-sn-glycero-3-phosphocholine |
| 11 | DSPC | 1,2-distearoyl-sn-glycero-3-phosphocholine |
| 12 | MO-CHOL | 4-(2-aminoethyl)-morpholino-cholesterolhemisuccinate |
| 13 | DSPE-PEG(2000) Carboxylic Acid | (1,2-distearoyl-sn-glycero-3-phosphoethanolamine-N-[carboxy(polyethylene glycol) |

TABLE II-continued

Examples of Helper Lipids.

| No. | Abbreviation | Name |
| --- | --- | --- |
| 14 | Hydro Soy PC ("HSPC") | L-α-phosphatidylcholine, hydrogenated (Soy) powder |

TABLE III

Examples of Phospholipids/Fatty Acids.

| No. | Name |
| --- | --- |
| 1 | Oleic acid |
| 2 | linolenic acid |
| 3 | arachidonic acid |
| 4 | docosahexaenoic (DHA) |
| 5 | Palmitic acid |
| 6 | Palmitoleic acid |
| 7 | Stearic acid |
| 8 | Eicosapentaenoic acid (EPA) |
| 9 | DSPE-PEG(2000) Carboxylic Acid (1,2-distearoyl-sn-glycero-3-phosphoethanolamine-N-[carboxy(polyethylene glycol) |
| 10 | DOPE-PEG(2000) Carboxylic acid (1,2-dioleoyl-sn-glycero-3-phosphoethanolamine-N-[carboxy (polyethylene glycol)-2000] (sodium salt) |

The invention claimed is:

1. A nanocarrier comprising, an AR prodrug whereby the nanocarrier releases an active A2aR inhibitor and wherein the AR prodrug has the following chemical structure:

and wherein the nanocarrier is a liposome and wherein the liposome has a Zav size of 87.29 nm and a Zeta potential of −18.6 m V.

2. The nanocarrier of claim 1, further comprising a helper lipid, whereby the helper lipid is selected from the group consisting of 1,2-dioleoyl-3-trimethylammonium-propane (chloride salt), 1,2-dioleyloxy-3-dimethylaminopropane, 1,2-dilinoleyloxy-3-dimethylaminopropane, 2,2-dilinoleyl-4-dimethylaminoethyl-[1,3]-dioxolane, 1,2-Dioleoyl-sn-glycero-3-phosphoethanolamine, 1,2-dioleoyl-sn-glycero-3-phosphocholine, cholesterol, N-[(methoxy poly(ethylene glycol) 2000) carbamyl]-1,2-dimyristyloxlpropyl-3-amine, cholesteryl hemisuccinate, 1,2-dipalmitoyl-sn-glycero-3-phosphocholine, 1,2-distearoyl-sn-glycero-3-phosphocho-line, 4-(2-aminoethyl)-morpholino-cholesterolhemisucci-nate, (1,2-distearoyl-sn-glycero-3-phosphoethanolamine-N-[carboxy(polyethylene glycol), L-α-phosphatidylcholine, and hydrogenated (Soy) powder.

3. The nanocarrier of claim 1, whereby the liposome is further co-formulated with one or more immune modulating agents or a lipid-prodrug thereof, wherein the immune modulating agent is selected from the group consisting of immunogenic-cell death (ICD) inducing chemotherapeutics, toll-like receptor (TLR) agonists, Stimulator of Interferon Gene (STING) agonists, Cytotoxic T-Lymphocyte-Associ-ated Protein 4 (CTLA-4) inhibitors, indoleamine 2,3-dioxy-genase (IDO) inhibitors, programmed cell death 1 (PD-1)/ programmed cell death ligand 1 (PD-L1) inhibitors, and cluster of differentiation 1 (CDID) agonists and/or prodrugs thereof.

4. The nanocarrier of claim 1, whereby the liposome is further co-formulated with an ICD-inducing chemotherapeutic, wherein the ICD-inducing chemotherapeutic is selected from the group consisting of doxorubicin (DOX), mitoxanthrone (MTO), oxaliplatin (OXA), cyclophosphamide (CP), Bortezomib, Carfilzomib, or Paclitaxel.

5. A kit comprising the nanocarrier of claim 1.

6. A kit comprising the nanocarrier of claim 3.

7. A kit comprising the nanocarrier of claim 4.

*   *   *   *   *